(12) United States Patent
Kaul et al.

(10) Patent No.: US 9,243,020 B2
(45) Date of Patent: Jan. 26, 2016

(54) SELECTIVE GLYCOSIDASE INHIBITORS AND USES THEREOF

(75) Inventors: Ramesh Kaul, Burnaby (CA); Ernest J. McEachern, Burnaby (CA); Harold G. Selnick, West Point, PA (US); David J. Vocadlo, Burnaby (CA); Yuanxi Zhou, Burnaby (CA); Yongbao Zhu, Burnaby (CA)

(73) Assignees: Alectos Therapeutics Inc., Burnaby (CA); Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 13/997,484

(22) PCT Filed: Dec. 21, 2011

(86) PCT No.: PCT/CA2011/001397
§ 371 (c)(1),
(2), (4) Date: Oct. 4, 2013

(87) PCT Pub. No.: WO2012/083435
PCT Pub. Date: Jun. 28, 2012

(65) Prior Publication Data
US 2014/0018309 A1    Jan. 16, 2014

Related U.S. Application Data

(63) Continuation-in-part of application No. PCT/CN2011/074569, filed on May 24, 2011.

(60) Provisional application No. 61/426,773, filed on Dec. 23, 2010, provisional application No. 61/507,684, filed on Jul. 14, 2011.

(30) Foreign Application Priority Data

May 24, 2011  (WO) ............... PCT/CN2011/074569

(51) Int. Cl.
| | | |
|---|---|---|
| C08B 37/00 | (2006.01) |
| C07D 487/02 | (2006.01) |
| A61K 31/70 | (2006.01) |
| A61K 31/425 | (2006.01) |
| C07H 17/00 | (2006.01) |
| C07D 513/04 | (2006.01) |
| C07H 9/06 | (2006.01) |
| C12Q 1/34 | (2006.01) |

(52) U.S. Cl.
CPC ............. *C07H 17/00* (2013.01); *C07D 513/04* (2013.01); *C07H 9/06* (2013.01); *C12Q 1/34* (2013.01)

(58) Field of Classification Search
None
See application file for complete search history.

(56) References Cited

U.S. PATENT DOCUMENTS

| | | | |
|---|---|---|---|
| 8,334,310 B2 * | 12/2012 | Vocadlo et al. ............... 514/367 |
| 8,541,441 B2 | 9/2013 | Vocadlo et al. |
| 2008/0287375 A1 | 11/2008 | Vocadlo et al. |
| 2010/0016386 A1 | 1/2010 | Vocadlo et al. |
| 2011/0237631 A1 | 9/2011 | Vocadlo et al. |
| 2011/0301217 A1 | 12/2011 | Vocadlo et al. |
| 2012/0316207 A1 | 12/2012 | Vocadlo et al. |
| 2013/0131044 A1 | 5/2013 | Li et al. |
| 2014/0005191 A1 | 1/2014 | Coburn et al. |
| 2014/0051719 A1 | 2/2014 | Vocadlo et al. |
| 2014/0088028 A1 | 3/2014 | Kaul et al. |
| 2014/0107044 A1 | 4/2014 | McEachern et al. |
| 2014/0275022 A1 | 9/2014 | Li et al. |
| 2014/0296205 A1 | 10/2014 | Li et al. |

FOREIGN PATENT DOCUMENTS

| | | |
|---|---|---|
| CA | 2599843 A1 | 9/2006 |
| CA | 2661582 A1 | 3/2008 |
| CN | 101595111 A | 12/2009 |
| JP | 01-180894 A | 7/1989 |
| JP | 07-316178 A | 12/1995 |
| JP | 09-132585 A | 5/1997 |
| JP | 2002-338532 A | 11/2002 |
| JP | 2003-12683 A | 1/2003 |
| WO | WO-2006/016904 A2 | 2/2006 |
| WO | WO2006/092049 * | 8/2006 |
| WO | WO-2008/025170 A1 | 3/2008 |
| WO | WO-2010/012106 A1 | 2/2010 |
| WO | WO-2010/012107 A1 | 2/2010 |
| WO | WO-2010/037207 A1 | 4/2010 |
| WO | WO-2011/140640 A1 | 11/2011 |
| WO | WO-2012/061927 A1 | 5/2012 |
| WO | WO-2012/061971 A1 | 5/2012 |
| WO | WO-2012/061972 A1 | 5/2012 |
| WO | WO-2012/064680 A1 | 5/2012 |
| WO | WO-2012/126091 A1 | 9/2012 |

(Continued)

OTHER PUBLICATIONS

Arias et al., "Prolonged incubation in PUGNAc results in increased protein O-Linked glycosylation and insulin resistance in rat skeletal muscle," Diabetes 53(4):921-30 (2004).
Bennett et al., "Alkylation of DNA in rat tissues following administration of streptozotocin," Cancer Res. 41(7):2786-90 (1981).
Bertram et al., "Evidence for genetic linkage of Alzheimer's disease to chromosome 10q," Science 290(5500):2302-3 (2000).
Bounelis et al., "Glucosamine provides protection from ischemia/reperfusion injury and calcium overload in isolated hearts and leads to an increase in O-linked glycosylation," Shock 21:58, Abstract 170 (2004).
Braidman et al., "Separation and properties of human brain hexosaminidase C," Biochem J. 143(2):295-301 (1974).
Brickley et al., "GRIF-1 and OIP106, members of a novel gene family of coiled-coil domain proteins: association in vivo and in vitro with kinesin," J Biol Chem. 280(15):14723-32 (2005).

(Continued)

*Primary Examiner* — Traviss C McIntosh, III
(74) *Attorney, Agent, or Firm* — Clark & Elbing LLP

(57) ABSTRACT

The invention provides compounds with enhanced permeability for selectively inhibiting glycosidases, prodrugs of the compounds, and pharmaceutical compositions including the compounds or prodrugs of the compounds. The invention also provides methods of treating diseases and disorders related to deficiency or overexpression of O-GlcNAcase, accumulation or deficiency of O-GlcNAc.

45 Claims, No Drawings

(56) References Cited

FOREIGN PATENT DOCUMENTS

| WO | WO-2012/129651 A1 | 10/2012 |
|---|---|---|
| WO | WO-2012/129802 A1 | 10/2012 |
| WO | WO-2013/000084 A1 | 1/2013 |
| WO | WO-2013/000085 A1 | 1/2013 |
| WO | WO-2013/000086 A1 | 1/2013 |
| WO | WO-2013/025452 A1 | 2/2013 |
| WO | WO-2013/028715 A1 | 2/2013 |
| WO | WO-2013/169576 A1 | 11/2013 |
| WO | WO-2014/032184 A1 | 3/2014 |
| WO | WO-2014/032185 A1 | 3/2014 |
| WO | WO-2014/032187 A1 | 3/2014 |
| WO | WO-2014/032188 A1 | 3/2014 |
| WO | WO-2014/067003 A1 | 5/2014 |
| WO | WO-2014/105662 A1 | 7/2014 |

OTHER PUBLICATIONS

Burkart et al., "Mice lacking the poly(ADP-ribose) polymerase gene are resistant to pancreatic beta-cell destruction and diabetes development induced by streptozocin," Nat Med. 5(3):314-9 (1999).
Champattanachai et al., "Glucosamine protects neonatal cardiomyocytes from ischemia-reperfusion injury via increased protein O—GlcNAc and increased mitochondrial Bcl-2," Am J Physiol Cell Physiol. 294(6):C1509-20 (2008).
Champattanachai et al., "Glucosamine protects neonatal cardiomyocytes from ischemia-reperfusion injury via increased protein-associated O—GlcNAc," Am J Physiol Cell Physiol 292(1):C178-87 (2007).
Cheng et al., "Alternative O-glycosylation/O-phosphorylation of serine-16 in murine estrogen receptor beta: post-translational regulation of turnover and transactivation activity," J Biol Chem. 276(13):10570-5 (2001).
Cheng et al., "Alternative O-glycosylation/O-phosphorylation of the murine estrogen receptor beta," Biochemistry 39(38):11609-20 (2000).
Chou et al., "c-Myc is glycosylated at threonine 58, a known phosphorylation site and a mutational hot spot in lymphomas," J Biol Chem. 270(32):18961-5 (1995).
Chou et al., "O-linked N-acetylglucosamine and cancer: messages from the glycosylation of c-Myc," Adv Exp Med Biol. 491:413-8 (2001).
Cole et al., "Glycosylation sites flank phosphorylation sites on synapsin I: O-linked N-acetylglucosamine residues are localized within domains mediating synapsin I interactions," J Neurochem. 73(1):418-28 (1999).
de la Monte et al., "Review of insulin and insulin-like growth factor expression, signaling, and malfunction in the central nervous system: relevance to Alzheimer's disease," J Alzheimers Dis. 7(1):45-61 (2005).
de la Torre, "Alzheimer's disease is a vasocognopathy: a new term to describe its nature," Neurol Res. 26(5):517-24 (2004).
Deng et al., "Regulation between O—GlcNAcylation and phosphorylation of neurofilament-M and their dysregulation in Alzheimer disease," FASEB J. 22(1):138-45 (2008).
Dong et al., "Purification and characterization of an O—GlcNAc selective N-acetyl-beta-D-glucosaminidase from rat spleen cytosol," J Biol Chem. 269(30):19321-30 (1994).
English translation of Office Action for Chinese Application No. 201180066766.4, dated Jul. 1, 2014 (8 pages).
Examination Report for New Zealand Application No. 612703, mailed Mar. 20, 2014 (2 pages).
Extended European Search Report for European Application No. 11850773.0, mailed May 20, 2014 (6 pages).
Friedhoff et al., "Rapid assembly of Alzheimer-like paired helical filaments from microtubule-associated protein tau monitored by fluorescence in solution," Biochemistry 37(28):10223-30 (1998).
Frölich et al., "Brain insulin and insulin receptors in aging and sporadic Alzheimer's disease," J Neural Transm. 105(4-5):423-38 (1998).

Fulop et al., "Diabetes, the hexosamine biosynthesis pathway and protein O-glycsoylation in the heart," Journal of Molecular and Cellular Cardiology 37:286-7 Abstract C86 (2004) (3 pages).
Fulop et al., "Effects of glucosamine on the isolated rat heart," FASEB J 19:A689-90 Abstract 386.6 (2005) (2 pages).
Fulop et al., "Glucosamine-induced cardioprotection mediated by the hexosamine biosynthesis pathway and increased levels of O-linked N-acetylglucosamine on nucleocytoplasmic proteins," Circ Res. 97:e28 Abstract 104 (2005).
Fulop et al., "Role of protein O-linked N-acetyl-glucosamine in mediating cell function and survival in the cardiovascular system," Cardiovasc Res. 73(2): 17 pages (2007).
Gao et al., "Dynamic O-glycosylation of nuclear and cytosolic proteins: cloning and characterization of a neutral, cytosolic beta-N-acetylglucosaminidase from human brain," J Biol Chem. 276(13):9838-45 (2001).
Gao et al., "Streptozotocin-induced beta-cell death is independent of its inhibition of O—GlcNAcase in pancreatic Min6 cells," Arch Biochem Biophys. 383(2):296-302 (2000).
Gloster et al., "Mechanism, Structure, and Inhibition of O—GlcNAc Processing Enzymes," Curr Signal Transduct Ther. 5(1): 33 pages (2010).
Goedert et al., "Multiple isoforms of human microtubule-associated protein tau: sequences and localization in neurofibrillary tangles of Alzheimer's disease," Neuron 3(4):519-26 (1989).
Goedert et al., "Tau proteins of Alzheimer paired helical filaments: abnormal phosphorylation of all six brain isoforms," Neuron 8(1):159-68 (1992).
Gong et al., "Impaired brain glucose metabolism leads to Alzheimer neurofibrillary degeneration through a decrease in tau O—GlcNAcylation," J Alzheimers Dis. 9(1):1-12 (2006).
Gong et al., "Post-translational modifications of tau protein in Alzheimer's disease," J Neural Transm. 112(6):813-38 (2005).
Griffith et al., "O-linked N-acetylglucosamine is upregulated in Alzheimer brains," Biochem Biophys Res Commun. 213(2):424-31 (1995).
Griffith et al., "O-linked N-acetylglucosamine levels in cerebellar neurons respond reciprocally to pertubations of phosphorylation," Eur J Biochem. 262(3):824-31 (1999).
Haltiwanger et al., "Enzymatic addition of O—GlcNAc to nuclear and cytoplasmic proteins. Identification of a uridine diphospho-N-acetylglucosamine:peptide beta-N-acetylglucosaminyltransferase," J Biol Chem. 265(5):2563-8 (1990).
Haltiwanger et al., "Modulation of O-linked N-acetylglucosamine levels on nuclear and cytoplasmic proteins in vivo using the peptide O—GlcNAc-beta-N-acetylglucosaminidase inhibitor O-(2-acetamido-2-deoxy-D-glucopyranosylidene)amino-N-phenylcarbamate," J Biol Chem. 273(6):3611-7 (1998).
Hanover et al., "Elevated O-linked N-acetylglucosamine metabolism in pancreatic beta-cells," Arch Biochem Biophys. 362(1):38-45 (1999).
Hanover, "Glycan-dependent signaling: O-linked N-acetylglucosamine," FASEB J. 15(11):1865-76 (2001).
Henrissat et al., "New families in the classification of glycosyl hydrolases based on amino acid sequence similarities," Biochem J. 293(Pt 3):781-8 (1993).
Henrissat et al., "Updating the sequence-based classification of glycosyl hydrolases," Biochem J. 316(Pt 2):695-6 (1996).
Horsch et al., "N-acetylglucosaminono-1,5-lactone oxime and the corresponding (phenylcarbamoyl)oxime. Novel and potent inhibitors of beta-N-acetylglucosaminidase," Eur J Biochem. 197(3):815-8 (1991).
Hoyer, "Brain glucose and energy metabolism abnormalities in sporadic Alzheimer disease. Causes and consequences: an update," Exp Gerontol. 35(9-10):1363-72 (2000).
Hoyer, "Causes and consequences of disturbances of cerebral glucose metabolism in sporadic Alzheimer disease: therapeutic implications," Adv Exp Med Biol. 541:135-52 (2004).
Huang et al., "The hexosamine biosynthesis pathway negatively regulates IL-2 production by Jurkat T cells," Cell Immunol 245(1): 10 pages (2007).

(56) References Cited

OTHER PUBLICATIONS

Iqbal et al., "Alzheimer neurofibrillary degeneration: therapeutic targets and high-throughput assays," J Mol Neurosci. 20(3):425-9 (2003).
Iqbal et al., "Pharmacological targets to inhibit Alzheimer neurofibrillary degeneration," J Neural Transm Suppl. (62):309-19 (2002).
Iyer et al., "Identification and cloning of a novel family of coiled-coil domain proteins that interact with O—GlcNAc transferase," J Biol Chem. 278(7):5399-409 (2003).
Iyer et al., "Roles of the tetratricopeptide repeat domain in O—GlcNAc transferase targeting and protein substrate specificity," J Biol Chem. 278(27):24608-16 (2003).
Jackson et al., "O-glycosylation of eukaryotic transcription factors: implications for mechanisms of transcriptional regulation," Cell 55(1):125-33 (1988).
Jagust et al., "Diminished glucose transport in Alzheimer's disease: dynamic PET studies," J Cereb Blood Flow Metab. 11(2):323-30 (1991).
Junod et al., "Studies of the diabetogenic action of streptozotocin," Proc Soc Exp Biol Med. 126(1):201-5 (1967).
Jínek et al., "The superhelical TPR-repeat domain of O-linked GlcNAc transferase exhibits structural similarities to importin alpha," Nat Struct Mol Biol. 11(10):1001-7 (2004).
Kalaria et al., "Reduced glucose transporter at the blood-brain barrier and in cerebral cortex in Alzheimer disease," J Neurochem. 53(4):1083-8 (1989).
Kamemura et al., "Dynamic interplay between O-glycosylation and O-phosphorylation of nucleocytoplasmic proteins: a new paradigm for metabolic control of signal transduction and transcription," Prog Nucleic Acid Res Mol Biol. 73:107-36 (2003).
Kamemura et al., "Dynamic interplay between O-glycosylation and O-phosphorylation of nucleocytoplasmic proteins: alternative glycosylation/phosphorylation of THR-58, a known mutational hot spot of c-Myc in lymphomas, is regulated by mitogens," J Biol Chem. 277(21):19229-35 (2002).
Kelly et al., "RNA polymerase II is a glycoprotein. Modification of the COOH-terminal domain by O—GlcNAc," J Biol Chem. 268(14):10416-24 (1993).
Khlistunova et al., "Inhibition of tau aggregation in cell models of tauopathy," Curr Alzheimer Res. 4(5):544-6 (2007).
Knapp et al., "Addition of trialkylaluminum reagents to glyconolactones. Synthesis of 1-C-methyl GlcNAc oxazoline and thiazoline," Tetrahedron Letters 43:7101-4 (2002).
Knapp et al., "NAG-thiazoline, an N-acetyl-beta-hexosaminidase inhibitor that implicates acetamido participation," J Am Chem Soc. 118:6804-5 (1996).
Knapp et al., "Tautomeric modification of GlcNAc-thiazoline," Org Lett. 9(12):2321-4 (2007).
Konrad et al., "The potential mechanism of the diabetogenic action of streptozotocin: inhibition of pancreatic beta-cell O—GlcNAc-selective N-acetyl-beta-D-glucosaminidase," Biochem J. 356(Pt 1):31-41 (2001).
Kreppel et al., "Dynamic glycosylation of nuclear and cytosolic proteins. Cloning and characterization of a unique O—GlcNAc transferase with multiple tetratricopeptide repeats," J Biol Chem. 272(14):9308-15 (1997).
Kröncke et al., "Nitric oxide generation during cellular metabolization of the diabetogenic N-methyl-N-nitroso-urea streptozotozin contributes to islet cell DNA damage," Biol Chem Hoppe Seyler 376(3):179-85 (1995).
Ksiezak-Reding et al., "Phosphate analysis and dephosphorylation of modified tau associated with paired helical filaments," Brain Res. 597(2):209-19 (1992).
Köpke et al., "Microtubule-associated protein tau. Abnormal phosphorylation of a non-paired helical filament pool in Alzheimer disease," J Biol Chem. 268(32):24374-84 (1993).
Lamarre-Vincent et al., "Dynamic glycosylation of the transcription factor CREB: a potential role in gene regulation," J Am Chem Soc. 125(22):6612-3 (2003).

Lau et al., "Tau protein phosphorylation as a therapeutic target in Alzheimer's disease," Curr Top Med Chem. 2(4):395-415 (2002).
Le Corre et al., "An inhibitor of tau hyperphosphorylation prevents severe motor impairments in tau transgenic mice," Proc Natl Acad Sci U.S.A. 103(25):9673-8 (2006).
Lefebvre et al., "Does O—GlcNAc play a role in neurodegenerative diseases?," Expert Rev Proteomics 2(2):265-75 (2005).
Legler et al., "Bovine N-acetyl-beta-D-glucosaminidase: affinity purification and characterization of its active site with nitrogen containing analogs of N-acetylglucosamine," Biochim Biophys Acta. 1080(2):89-95 (1991).
Li et al., "Casein kinase 1 delta phosphorylates tau and disrupts its binding to microtubules," J Biol Chem. 279(16):15938-45 (2004).
Lillelund et al., "Recent developments of transition-state analogue glycosidase inhibitors of non-natural product origin," Chem Rev. 102(2):515-53 (2002).
Liu et al., "Accumulation of protein O—GlcNAc modification inhibits proteasomes in the brain and coincides with neuronal apoptosis in brain areas with high O—GlcNAc metabolism," J Neurochem. 89(4):1044-55 (2004).
Liu et al., "Glutamine protects isolated rat heart from ischemia/reperfusion injury through the hexosamine biosynthesis pathway," FASEB 20:A317 Abstract only (2006).
Liu et al., "Glutamine-induced protection of isolated rat heart from ischemia/reperfusion injury is mediated via the hexosamine biosynthesis pathway and increased protein O—GlcNAc levels," J Mol Cell Cardiol 42(1):17 pages (2007).
Liu et al., "Hexosaminidase inhibitors as new drug candidates for the therapy of osteoarthritis," Chem Biol. 8(7):701-11 (2001).
Liu et al., "Increased hexosamine biosynthesis and protein O—GlcNAc levels associated with myocardial protection against calcium paradox and ischemia," J Mol Cell Cardiol. 40(2):303-12 (2006).
Liu et al., "O—GlcNAcylation regulates phosphorylation of tau: a mechanism involved in Alzheimer's disease," Proc Natl Acad Sci U.S.A. 101(29):10804-9 (2004).
Liu et al., "O-linked N-acetylglucosamine modification of proteins protect isolated perfused rat heart from ischemia/reperfusion injury," FASEB J 19:A691 Abstract 386.11 (2005).
Liu et al., "Streptozotocin, an O—GlcNAcase inhibitor, blunts insulin and growth hormone secretion," Mol Cell Endocrinol. 194(1-2):135-46 (2002).
Liu et al., "Tau becomes a more favorable substrate for GSK-3 when it is prephosphorylated by PKA in rat brain," J Biol Chem. 279(48):50078-88 (2004).
Lubas et al., "Analysis of nuclear pore protein p62 glycosylation," Biochemistry 34(5):1686-94 (1995).
Lubas et al., "Functional expression of O-linked GlcNAc transferase. Domain structure and substrate specificity," J Biol Chem. 275(15):10983-8 (2000).
Lubas et al., "O-Linked GlcNAc transferase is a conserved nucleocytoplasmic protein containing tetratricopeptide repeats," J Biol Chem. 272(14):9316-24 (1997).
Macauley et al., "Enzymatic characterization and inhibition of the nuclear variant of human O—GlcNAcase," Carbohydr Res. 344(9):1079-84 (2009).
Macauley et al., "Increasing O—GlcNAc levels: an overview of small-molecule inhibitors of O—GlcNAcase," Biochim Biophys Acta. 1800(2):107-21 (2010).
Macauley et al., "O—GlcNAcase uses substrate-assisted catalysis: kinetic analysis and development of highly selective mechanism-inspired inhibitors," J Biol Chem. 280(27):25313-22 (2005).
Marchase et al., "Protection from ischemic and hypovolemic injury by hyperglycemia is transduced by hexosamine biosynthesis and O-linked N-acetylglucosamine on cytoplasmic proteins," Circulation 110:III-1099 Abstract only (2004).
Mark et al., "Crystallographic evidence for substrate-assisted catalysis in a bacterial beta-hexosaminidase," J Biol Chem. 276(13):10330-7 (2001).
Marshall et al., "New insights into the metabolic regulation of insulin action and insulin resistance: role of glucose and amino acids," FASEB J. 5(15):3031-6 (1991).

(56) References Cited

OTHER PUBLICATIONS

Mazanetz et al., "Untangling tau hyperphosphorylation in drug design for neurodegenerative diseases," Nat Rev Drug Discov. 6(6):464-79 (2007).
McClain et al., "Altered glycan-dependent signaling induces insulin resistance and hyperleptinemia," Proc Natl Acad Sci U.S.A. 99(16):10695-9 (2002).
Miller et al., "Sperm require beta-N-acetylglucosaminidase to penetrate through the egg zona pellucida," Development 118(4):1279-89 (1993).
Nagy et al., "Glucosamine inhibits angiotensin II-induced cytoplasmic $Ca^{2+}$ elevation in neonatal cardiomyocytes via protein-associated O-linked N-acetylglucosamine," Am J Physiol Cell Physiol. 290(1):C57-65 (2006).
Noble et al., "Inhibition of glycogen synthase kinase-3 by lithium correlates with reduced tauopathy and degeneration in vivo," Proc Natl Acad Sci U.S.A. 102(19):6990-5 (2005).
Nöt et al., "Glucosamine administration improves survival following trauma-hemorrhage in rats," FASEB 20:A1471 Abstract only (2006).
Okuyama et al., "Cytosolic O—GlcNAc accumulation is not involved in beta-cell death in HIT-T15 or Min6," Biochem Biophys Res Commun. 287(2):366-71 (2001).
Parker et al., "Hyperglycemia and inhibition of glycogen synthase in streptozotocin-treated mice: role of O-linked N-acetylglucosamine," J Biol Chem. 279(20):20636-42 (2004).
Pickhardt et al., "Anthraquinones inhibit tau aggregation and dissolve Alzheimer's paired helical filaments in vitro and in cells," J Biol Chem. 280(5):3628-35 (2005).
Roos et al., "O glycosylation of an Sp1-derived peptide blocks known Sp1 protein interactions," Mol Cell Biol. 17(11):6472-80 (1997).
Roos et al., "Streptozotocin, an analog of N-acetylglucosamine, blocks the removal of O—GlcNAc from intracellular proteins," Proc Assoc Am Physicians 110(5):422-32 (1998).
Roquemore et al., "Dynamic O—GlcNAcylation of the small heat shock protein αβ-crystallin," Biochemistry 35(11):3578-86 (1996).
Simpson et al., "Decreased concentrations of GLUT1 and GLUT3 glucose transporters in the brains of patients with Alzheimer's disease," Ann Neurol. 35(5):546-51 (1994).
Toleman et al., "Characterization of the histone acetyltransferase (HAT) domain of a bifunctional protein with activable O—GlcNAcase and HAT activities," J Biol Chem. 279(51):53665-73 (2004).
Torres et al., "Topography and polypeptide distribution of terminal N-acetylglucosamine residues on the surfaces of intact lymphocytes. Evidence for O-linked GlcNAc," J Biol Chem. 259(5):3308-17 (1984).
Triggs-Raine et al., "Naturally occurring mutations in $G_{M2}$ gangliosidosis: a compendium," Adv Genet. 44:199-224 (2001).
Ueno et al., "Purification and properties of neutral beta-N-acetylglucosaminidase from carp blood," Biochim Biophys Acta. 1074(1):79-84 (1991).
Volpe, "Application of method suitability for drug permeability classification," AAPS J. 12(4):670-8 (2010).
Vosseller et al., "Elevated nucleocytoplasmic glycosylation by O—GlcNAc results in insulin resistance associated with defects in Akt activation in 3T3-L1 adipocytes," Proc Natl Acad Sci U.S.A. 99(8):5313-8 (2002).
Wells et al., "Glycosylation of nucleocytoplasmic proteins: signal transduction and O—GlcNAc," Science 291(5512):2376-8 (2001).
Wells et al., "O—GlcNAc transferase is in a functional complex with protein phosphatase 1 catalytic subunits," J Biol Chem. 279(37):38466-70 (2004).
Whitworth et al., "Analysis of PUGNAc and NAG-thiazoline as transition state analogues for human O—GlcNAcase: mechanistic and structural insights into inhibitor selectivity and transition state poise," J Am Chem Soc. 129(3):635-44 (2007).
Yamada et al., "Preventive and therapeutic effects of large-dose nicotinamide injections on diabetes associated with insulitis. An observation in nonobese diabetic (NOD) mice," Diabetes 31(9):749-53 (1982).
Yamamoto et al., "Streptozotocin and alloxan induce DNA strand breaks and poly(ADP-ribose) synthetase in pancreatic islets," Nature 294(5838):284-6 (1981).
Yang et al., "Glucosamine administration during resuscitation improves organ function after trauma hemorrhage," Shock 25(6):600-7 (2006).
Yang et al., "Modification of p53 with O-linked N-acetylglucosamine regulates p53 activity and stability," Nat Cell Biol. 8(10):1074-83 (2006).
Yao et al., "Reduction of O-linked N-acetylglucosamine-modified assembly protein-3 in Alzheimer's disease," J Neurosci. 18(7):2399-411 (1998).
Yuzwa et al., "A potent mechanism-inspired O—GlcNAcase inhibitor that blocks phosphorylation of tau in vivo," Nat Chem Biol. 4(8):483-90 (2008).
Zachara et al., "Dynamic O—GlcNAc modification of nucleocytoplasmic proteins in response to stress. A survival response of mammalian cells," J Biol Chem. 279(29):30133-42 (2004).
Zachara et al., "Increased O—GlcNAc in response to stress, a survival response of mammals," Conference Abstracts of Joint Meeting of the Society for Glycobiology and the Japanese Society of Carbohydrate Research, Honolutu, HI, Nov. 17-20, 2004, p. 1170 Abstract 418.
Zhang et al., "O—GlcNAc modification is an endogenous inhibitor of the proteasome," Cell 115(6):715-25 (2003).
Zhou et al., "Lysosomal glycosphingolipid recognition by NKT cells," Science 306(5702):1786-9 (2004).
Zhu et al., "Insulin signaling, diabetes mellitus and risk of Alzheimer disease," J Alzheimers Dis. 7(1):81-4 (2005).
Zou et al., "Glucosamine improves recovery following trauma hemorrhage in rat," FASEB J. 19:A1224 Abstract 685.16 (2005).
Zou et al., "Increasing protein O—GlcNAc levels by inhibition of O—GlcNAcase improves cardiac function following trauma hemorrhage and resuscitation in rat," FASEB 20:A1471 Abstract only (2006).
Zou et al., "The protective effects of PUGNAc on cardiac function after trauma-hemorrhage are mediated via increased protein O—GlcNAc levels," Shock 27(4):402-8 (2007).
Office Action for Canadian Application No. 2,661,582, mailed Jul. 30, 2014 (2 pages).
English translation of Decision on Rejection for Chinese Application No. 200780040905.X, issuing on May 7, 2014 (12 pages).
English translation of Official Action for Japanese Application No. 2013-123917, mailed Aug. 12, 2014 (3 pages).
Extended European Search Report for European Application No. 12761443.6, mailed Jul. 24, 2014 (7 pages).
Avalos Gonzalez et al., "Sintesis de hidrobromuros de glucopirano[2,1-d]-2-tiazo-linas," Anales de Quimica 84(1):5-11 (1988) (English abstract included).
Communication pursuant to Article 94(3) EPC for European Application No. 11157096.6, mailed Sep. 18, 2014 (4 pages).
International Search Report and Written Opinion for International Application No. PCT/CA2011/001397, mailed Mar. 12, 2012 (12 pages).
International Search Report for International Application No. PCT/CN2011/074569, mailed Feb. 16, 2012 (5 pages).
English Language Translation of Office Action for Colombian National Phase of International Patent Application No. PCT/CN2011/074569, received Nov. 13, 2014 (2 pages).
Second Office Action for Chinese Application No. 201180066766.4, dated Mar. 31, 2015 (18 pages).
Office Action for Mexican Application No. MX/a/2013/007434, dated Jul. 2, 2015 (7 pages).
Office Action for Thai Application No. 1301003501, dated May 18, 2015 (4 pages).
Rao et al., "Structural insights into the mechanism and inhibition of eukaryotic O-GlcNAc hydrolysis," EMBO J. 25(7):1569-78 (2006).
Rempel et al., "Covalent inhibitors of glycosidases and their applications in biochemistry and biology," Glycobiology. 18(8):570-86 (2008).

\* cited by examiner

SELECTIVE GLYCOSIDASE INHIBITORS AND USES THEREOF

CROSS-REFERENCE TO RELATED APPLICATIONS

This application is the U.S. National Stage filing under 35 U.S.C. §371 of International Application No. PCT/CA2011/001397, filed Dec. 21, 2011, which is a continuation-in-part of International Application No. PCT/CN2011/074569, filed May 24, 2011, and which claims the benefit of U.S. Provisional Application No. 61/426,773, filed Dec. 23, 2010, and of U.S. Provisional Application No. 61/507,684, filed Jul. 14, 2011.

FIELD OF THE INVENTION

This application relates to compounds which selectively inhibit glycosidases and uses thereof.

BACKGROUND OF THE INVENTION

A wide range of cellular proteins, both nuclear and cytoplasmic, are post-translationally modified by the addition of the monosaccharide 2-acetamido-2-deoxy-β-D-glucopyranoside (β-N-acetylglucosamine) which is attached via an O-glycosidic linkage.[1] This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGT).[2-5] A second enzyme, known as glycoprotein 2-acetamido-2-deoxy-β-D-glucopyranosidase (O-GlcNAcase)[6,7] removes this post-translational modification to liberate proteins making the O-GlcNAc-modification a dynamic cycle occurring several times during the lifetime of a protein.[8]

O-GlcNAc-modified proteins regulate a wide range of vital cellular functions including, for example, transcription,[9-12] proteasomal degradation,[13] and cellular signaling.[14] O-GlcNAc is also found on many structural proteins.[15-17] For example, it has been found on a number of cytoskeletal proteins, including neurofilament proteins,[18,19] synapsins,[6,20] synapsin-specific clathrin assembly protein AP-3,[7] and ankyrinG.[14] O-GlcNAc modification has been found to be abundant in the braill.[21,22] It has also been found on proteins clearly implicated in the etiology of several diseases including Alzheimer's disease (AD) and cancer.

For example, it is well established that AD and a number of related tauopathies including Downs' syndrome, Pick's disease, Niemann-Pick Type C disease, and amyotrophic lateral sclerosis (ALS) are characterized, in part, by the development of neurofibrillary tangles (NFTs). These NFTs are aggregates of paired helical filaments (PHFs) and are composed of an abnormal form of the cytoskeletal protein "tau". Normally tau stabilizes a key cellular network of microtubules that is essential for distributing proteins and nutrients within neurons. In AD patients, however, tau becomes hyperphosphorylated, disrupting its normal functions, forming PHFs and ultimately aggregating to form NFTs. Six isoforms of tau are found in the human brain. In AD patients, all six isoforms of tau are found in NFTs, and all are markedly hyperphosphorylated.[23,24] Tau in healthy brain tissue bears only 2 or 3 phosphate groups, whereas those found in the brains of AD patients bear, on average, 8 phosphate groups.[25,26] A clear parallel between NFT levels in the brains of AD patients and the severity of dementia strongly supports a key role for tau dysfunction in AD.[27,28] The precise causes of this hyperphosphorylation of tau remain elusive. Accordingly, considerable effort has been dedicated toward: a) elucidating the molecular physiological basis of tau hyperphosphorylation;[29] and b) identifying strategies that could limit tau hyperphosphorylation in the hope that these might halt, or even reverse, the progression of Alzheimer's disease[30-33] Thus far, several lines of evidence suggest that up-regulation of a number of kinases may be involved in hyperphosphorylation of tau,[21,34,35] although very recently, an alternative basis for this hyperphosphorylation has been advanced.[21]

In particular, it has emerged that phosphate levels of tau are regulated by the levels of O-GlcNAc on tau. The presence of O-GlcNAc on tau has stimulated studies that correlate O-GlcNAc levels with tau phosphorylation levels. The interest in this field stems from the observation that O-GlcNAc modification has been found to occur on many proteins at amino acid residues that are also known to be phosphorylated.[36-38] Consistent with this observation, it has been found that increases in phosphorylation levels result in decreased O-GlcNAc levels and conversely, increased O-GlcNAc levels correlate with decreased phosphorylation levels.[39] This reciprocal relationship between O-GlcNAc and phosphorylation has been termed the "Yin-Yang hypothesis"[40] and has gained strong biochemical support by the discovery that the enzyme OGT[4] forms a functional complex with phosphatases that act to remove phosphate groups from proteins.[41] Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD.[7,42] Hyperphosphorylated tau in human AD brains has markedly lower levels of O-GlcNAc than are found in healthy human brains.[21] It has been shown that O-GlcNAc levels of soluble tau protein from human brains affected with AD are markedly lower than those from healthy brain.[21] Furthermore, PHF from diseased brain was suggested to lack completely any O-GlcNAc modification whatsoever.[21] The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosamindase inhibitor was used to increase tau O-GlcNAc levels, whereupon it was observed that phosphorylation levels decreased.[21] The implication of these collective results is that by maintaining healthy O-GlcNAc levels in AD patients, such as by inhibiting the action of O-GlcNAcase, one should be able to block hyperphosphorylation of tau and all of the associated effects of tau hyperphosphorylation, including the formation of NFTs and downstream effects. However, because the proper functioning of the β-hexosaminidases is critical, any potential therapeutic intervention for the treatment of AD that blocks the action of O-GlcNAcase would have to avoid the concomitant inhibition of both hexosaminidases A and B.

Neurons do not store glucose and therefore the brain relies on glucose supplied by blood to maintain its essential metabolic functions. Notably, it has been shown that within brain, glucose uptake and metabolism decreases with aging.[43] Within the brains of AD patients marked decreases in glucose utilization occur and are thought to be a potential cause of neurodegeneration.[44] The basis for this decreased glucose supply in AD brain[45-47] is thought to stem from any of decreased glucose transport,[48,49] impaired insulin signaling,[50,51] and decreased blood flow.[52]

In light of this impaired glucose metabolism, it is worth noting that of all glucose entering into cells, 2-5% is shunted into the hexosamine biosynthetic pathway, thereby regulating cellular concentrations of the end product of this pathway, uridine diphosphate-N-acetylglucosamine (UDP-GlcNAc).[53] UDP-GlcNAc is a substrate of the nucleocytoplasmic enzyme O-GlcNAc transferase (OGT),[2-5] which acts to post-translationally add GlcNAc to specific serine and threonine residues of numerous nucleocytoplasmic proteins. OGT recognizes many of its substrates[54,55] and binding partners[41,56] through its tetratricopeptide repeat (TPR) domains.[57,58] As described above, O-GlcNAcase[6,7] removes this post-translational modification to liberate proteins making the O-GlcNAc-modification a dynamic cycle occurring several times during the lifetime of a protein.[8] O-GlcNAc has been found in several proteins on known phosphorylation sites,[10,37,38,59] including tau and neurofilaments.[60] Additionally, OGT shows unusual kinetic behaviour making it exquisitely sensitive to intracellular UDP-GlcNAc substrate concentrations and therefore glucose supply.[41]

Consistent with the known properties of the hexosamine biosynthetic pathway, the enzymatic properties of OGT, and the reciprocal relationship between O-GlcNAc and phosphorylation, it has been shown that decreased glucose availability in brain leads to tau hyperphosphorylation.[44] Therefore the gradual impairment of glucose transport and metabolism, whatever its causes, leads to decreased O-GlcNAc and hyperphosphorylation of tau (and other proteins). Accordingly, the inhibition of O-GlcNAcase should compensate for the age related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention[61] comes from recent studies showing that when transgenic mice harbouring human tau are treated with kinase inhibitors, they do not develop typical motor defects[33] and, in another case,[32] show decreased levels of insoluble tau. These studies provide a clear link between lowering tau phosphorylation levels and alleviating AD-like behavioural symptoms in a murine model of this disease. Indeed, pharmacological modulation of tau hyperphosphorylation is widely recognized as a valid therapeutic strategy for treating AD and other neurodegenerative disorders.[62]

Small-molecule O-GlcNAcase inhibitors, to limit tau hyperphosphorylation, have been considered for treatment of AD and related tauopathies.[63] Specifically, the O-GlcNAcase inhibitor thiamet-G has been implicated in the reduction of tau phosphorylation in cultured PC-12 cells at pathologically relevant sites.[63] Moreover, oral administration of thiamet-G to healthy Sprague-Dawley rats has been implicated in reduced phosphorylation of tau at Thr231, Ser396 and Ser422 in both rat cortex and hippocampus.[63]

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animals models of ischemia/reperfusion,[64-70] trauma hemorrhage,[71-73] hypervolemic shock,[74] and calcium paradox.[64,75] Moreover, strong evidence indicates that these cardioprotective effects are mediated by elevated levels of protein O-GlcNAc modification.[64,65,67,70,72,75-78] There is also evidence that the O-GlcNAc modification plays a role in a variety of neurodegenerative diseases, including Parkinson's disease and Huntington's disease.[79]

Humans have three genes encoding enzymes that cleave terminal β-N-acetyl-glucosamine residues from glycoconjugates. The first of these encodes O-GlcNAcase. O-GlcNAcase is a member of family 84 of glycoside hydrolases that includes enzymes from organisms as diverse as prokaryotic pathogens to humans (for the family classification of glycoside hydrolases see Coutinho, P. M. & Henrissat, B. (1999) Carbohydrate-Active Enzymes server at URL: http://afmb.cnrs-mrs.fr/CAZY/.[27,28] O-GlcNAcase acts to hydrolyse O-GlcNAc off of serine and threonine residues of post-translationally modified proteins.[1,6,7,80,81] Consistent with the presence of O-GlcNAc on many intracellular proteins, the enzyme O-GlcNAcase appears to have a role in the etiology of several diseases including type II diabetes,[14,82] AD,[16,21,83] and cancer.[22,84] Although O-GlcNAcase was likely isolated earlier on,[18,19] about 20 years elapsed before its biochemical role in acting to cleave O-GlcNAc from serine and threonine residues of proteins was understood.[6] More recently O-GlcNAcase has been cloned,[7] partially characterized,[20] and suggested to have additional activity as a histone acetyltransferase.[20] However, little was known about the catalytic mechanism of this enzyme.

The other two genes, HEXA and HEXB, encode enzymes catalyzing the hydrolytic cleavage of terminal β-N-acetylglucosamine residues from glycoconjugates. The gene products of HEXA and HEXB predominantly yield two dimeric isozymes, hexosaminidase A and hexosaminidase B, respectively. Hexosaminidase A (αβ), a heterodimeric isozyme, is composed of an α- and a β-subunit. Hexosaminidase B (ββ), a homodimeric isozyme, is composed of two β-subunits. The two subunits, α- and β-, bear a high level of sequence identity. Both of these enzymes are classified as members of family 20 of glycoside hydrolases and are normally localized within lysosomes. The proper functioning of these lysosomal β-hexosaminidases is critical for human development, a fact that is underscored by the tragic genetic illnesses, Tay-Sach's and Sandhoff diseases which stem from a dysfunction in, respectively, hexosaminidase A and hexosaminidase B.[85] These enzymatic deficiencies cause an accumulation of glycolipids and glycoconjugates in the lysosomes resulting in neurological impairment and deformation. The deleterious effects of accumulation of gangliosides at the organismal level are still being uncovered.[86]

As a result of the biological importance of these β-N-acetyl-glucosaminidases, small molecule inhibitors of glycosidases[87-90] have received a great deal of attention,[91] both as tools for elucidating the role of these enzymes in biological processes and in developing potential therapeutic applications. The control of glycosidase function using small molecules offers several advantages over genetic knockout studies including the ability to rapidly vary doses or to entirely withdraw treatment.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, many compounds that act to block O-GlcNAcase function are non-specific and act potently to inhibit the lysosomal β-hexosaminidases.

A few of the better characterized inhibitors of β-N-acetyl-glucosaminidases which have been used in studies of O-GlcNAc post-translational modification within both cells and tissues are streptozotocin (STZ), 2"-methyl-α-D-glu-copyrano-[2,1-d]-Δ2'-thiazoline (NAG-thiazoline) and O-(2-acetamido-2-deoxy-D-glucopyranosylidene)amino N-phe-nylcarbamate (PUGNAc).[14,92-95]

STZ has long been used as a diabetogenic compound because it has a particularly detrimental effect on β-islet cells.[96] STZ exerts its cytotoxic effects through both the alkylation of cellular DNA[96,97] as well as the generation of radical species including nitric oxide.[98] The resulting DNA strand breakage promotes the activation of poly(ADP-ribose) polymerase (PARP)[99] with the net effect of depleting cellular NAD+levels and, ultimately, leading to cell death.[100,101] Other investigators have proposed instead that STZ toxicity is a consequence of the irreversible inhibition of O-GlcNAcase, which is highly expressed within β-islet cells.[92,102] This hypothesis has, however, been brought into question by two independent research groups.[103,104] Because cellular O-GlcNAc levels on proteins increase in response to many forms of cellular stress[105] it seems possible that STZ results in increased O-GlcNAc-modification levels on proteins by inducing cellular stress rather than through any specific and direct action on O-GlcNAcase. Indeed, Hanover and coworkers have shown that STZ functions as a poor and somewhat selective inhibitor of O-GlcNAcase[106] and although it has been proposed by others that STZ acts to irreversibly inhibit O-GlcNAcase,[107] there has been no clear demonstration of this mode of action. More recently, it has been shown that STZ does not irreversibly inhibit O-GlcNAcase.[108]

NAG-thiazoline has been found to be a potent inhibitor of family 20 hexosaminidases,[90,109] and more recently, the family 84 O-GlcNAcases.[108] Despite its potency, a downside to using NAG-thiazoline in a complex biological context is that it lacks selectivity and therefore perturbs multiple cellular processes.

PUGNAc is another compound that suffers from the same problem of lack of selectivity, yet has enjoyed use as an inhibitor of both human O-GlcNAcase[6,110] and the family 20 human β-hexosaminidases.[111] This molecule, developed by Vasella and coworkers, was found to be a potent competitive inhibitor of the β-N-acetyl-glucosaminidases from *Canavalia ensiformis*, *Mucor rouxii*, and the β-hexosaminidase from bovine kidney.[88] It has been demonstrated that administration of PUGNAc in a rat model of trauma hemorrhage decreases circulating levels of the pro-inflammatory cytokines TNF-α and IL-6.[112] It has also been shown that administration of PUGNAc in a cell-based model of lymphocyte activation decreases production of the cytokine IL-2.[113] Subsequent studies have indicated that PUGNAc can be used in an animal model to reduce myocardial infarct size after left coronary artery occlusions.[114] Of particular significance is the fact that elevation of O-GlcNAc levels by administration of PUGNAc, an inhibitor of O-GlcNAcase, in a rat model of trauma hemorrhage improves cardiac function.[112,115] In addition, elevation of O-GlcNAc levels by treatment with PUGNAc in a cellular model of ischemia/reperfusion injury using neonatal rat ventricular myocytes improved cell viability and reduced necrosis and apoptosis compared to untreated cells.[116]

More recently, it has been suggested that the selective O-GlcNAcase inhibitor NButGT exhibits protective activity in cell-based models of ischemia/reperfusion and cellular stresses, including oxidative stress.[117] This study suggests the use of O-GlcNAcase inhibitors to elevate protein O-GlcNAc levels and thereby prevent the pathogenic effects of stress in cardiac tissue.

International patent applications PCT/CA2006/000300, filed 1 Mar. 2006, published under No. WO 2006/092049 on 8 Sep. 2006; PCT/CA2007/001554, filed 31 Aug. 2007, published under No. WO 2008/025170 on 6 Mar. 2008; PCT/CA2009/001087, filed 31 Jul. 2009, published under No. WO 2010/012106 on 4 Feb. 2010; PCT/CA2009/001088, filed 31 Jul. 2009, published under WO 2010/012107 on 4 Feb. 2010; and PCT/CA2009/001302, filed 16 Sep. 2009, published under WO 2010/037207 on 8 Apr. 2010, describe selective inhibitors of O-GlcNAcase.

SUMMARY OF THE INVENTION

The invention provides, in part, compounds for selectively inhibiting glycosidases, prodrugs of the compounds, uses of the compounds and the prodrugs, pharmaceutical compositions including the compounds or prodrugs of the compounds, and methods of treating diseases and disorders related to deficiency or overexpression of O-GlcNAcase, and/or accumulation or deficiency of O-GlcNAc.

In one aspect, the invention provides a compound of Formula (I) or a pharmaceutically acceptable salt thereof:

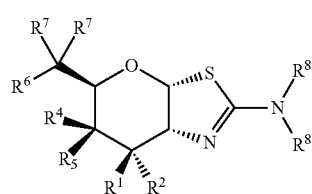

(I)

where $R^1$ and $R^2$ may be H, or $R^1$ may be H and $R^2$ may be F, or $R^1$ may be F and $R^2$ may be H, or $R^1$ may be $OR^3$ and $R^2$ may be H; each $R^3$ may be independently H or $C_{1-6}$ acyl; $R^4$ may be H and $R^5$ may be $OR^3$, or $R^4$ may be $OR^3$ and $R^5$ may be H; $R^6$ may be H, F, or $OR^3$; each $R^7$ may be independently H or F; each $R^8$ may be independently selected from the group consisting of: H, $C_{1-6}$ alkyl, $C_{3-6}$ alkenyl, $C_{3-6}$ alkynyl, and $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl, or the two $R^8$ groups may be connected together with the nitrogen atom to which they are attached to form a ring, said ring optionally independently substituted from one up to the maximum number of substituents with one or more of fluoro, OH, or methyl; with the proviso that when $R^6$ is $OR^3$, each $R^7$ is H; and with the proviso that either $R^1$ or $R^6$ is other than $OR^3$.

In alternative embodiments, the invention provides a compound of Formula (I) or a pharmaceutically acceptable salt thereof:

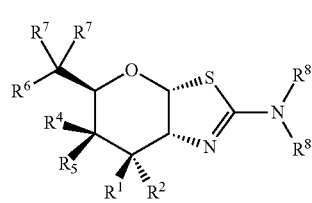

(I)

where $R^1$ and $R^2$ may be H and $R^6$ may be H, F or $OR^3$; or $R^1$ may be H and $R^2$ may be F and $R^6$ may be H, F or $OR^3$; or $R^1$ may be F and $R^2$ may be H and $R^6$ may be H, F or $OR^3$; or $R^1$ may be $OR^3$ and $R^2$ may be H and $R^6$ may be H or F; each $R^3$ may be independently H or $C_{1-6}$ acyl; $R^4$ may be H and $R^5$ may be $OR^3$; or $R^4$ may be $OR^3$ and $R^5$ may be H; each $R^7$ may be independently H or F; each $R^8$ may be independently selected from the group consisting of: H, $C_{1-6}$ alkyl, $C_{3-6}$ alkenyl, $C_{3-6}$ alkynyl, and $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl, or the two $R^8$ groups may be connected together with the nitrogen atom to which they are attached to form a ring, said ring optionally independently substituted from one up to the maximum number of substituents with one or more of fluoro, OH, or methyl; with the proviso that when $R^6$ is $OR^3$, each $R^7$ is H.

In alternative embodiments, the invention provides a compound of Formula (Ia) or a pharmaceutically acceptable salt thereof:

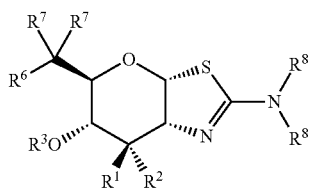

(Ia)

where $R^1$ and $R^2$ may be H and $R^6$ may be F; or $R^1$ may be H and $R^2$ may be F and $R^6$ may be H, F or $OR^3$; or $R^1$ may be F and $R^2$ may be H and $R^6$ may be H, F or $OR^3$; or $R^1$ may be $OR^3$ and $R^2$ may be H and $R^6$ may be F; each $R^3$ may be independently H or $C_{1-6}$ acyl; each $R^7$ may be independently H or F; each $R^8$ may be independently selected from the group consisting of: H, $C_{1-6}$ alkyl, $C_{3-6}$ alkenyl, $C_{3-6}$ alkynyl, and $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl, or the two $R^8$ groups may be connected together with the nitrogen atom to which they are attached to form a ring, said ring optionally independently substituted from one up to the maximum number of substituents with one or more of fluoro, OH, or methyl; with the proviso that when $R^6$ is $OR^3$, each $R^7$ is H.

In alternative embodiments, the invention provides a compound of Formula (Ib) or a pharmaceutically acceptable salt thereof:

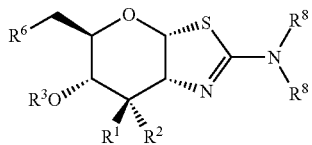

(Ib)

where $R^1$ and $R^2$ may be H and $R^6$ may be H or $OR^3$; or $R^1$ may be $OR^3$ and $R^2$ may be H and $R^6$ may be H; each $R^3$ may be independently H or $C_{1-6}$ acyl; each $R^8$ may be independently selected from the group consisting of: H, $C_{1-6}$ alkyl, $C_{3-6}$ alkenyl, $C_{3-6}$ alkynyl, and $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl, or the two $R^8$ groups may be connected together with the nitrogen atom to which they are attached to form a ring, said ring optionally independently substituted from one up to the maximum number of substituents with one or more of fluoro, OH, or methyl.

In alternative embodiments, the invention provides a compound of Formula (I) or a pharmaceutically acceptable salt thereof:

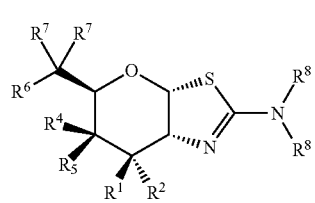

(I)

where $R^1$ may be H, F or $OR^3$; $R^2$ may be H or F; each $R^3$ may be independently H or $C_{1-6}$ acyl; $R^4$ may be H; $R^5$ may be $OR^3$; $R^6$ may be H, F, or $OR^3$; each $R^7$ may be independently H or F; each $R^8$ may be independently selected from the group consisting of: H, $C_{1-6}$ alkyl, $C_{3-6}$ alkenyl, $C_{3-6}$ alkynyl, and $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl, or the two $R^8$ groups may be connected together with the nitrogen atom to which they are attached to form a ring, said ring optionally independently substituted from one up to the maximum number of substituents with one or more of fluoro, OH, or methyl; with the proviso that when $R^1$ is $OR^3$, $R^2$ is H; and with the proviso that when $R^6$ is $OR^3$, each $R^7$ is H; and with the proviso that either $R^1$ or $R^6$ is other than $OR^3$; and with the proviso that either $R^1$ or $R^2$ is other than F.

In alternative embodiments, the compound may be a prodrug; the compound may selectively inhibit an O-glycoprotein 2-acetamido-2-deoxy-β-D-glucopyranosidase (O-GlcNAcase); the compound may selectively bind an O-GlcNAcase (e.g., a mammalian O-GlcNAcase); the compound may selectively inhibit the cleavage of a 2-acetamido-2-deoxy-β-D-glucopyranoside (O-GlcNAc); the compound may not substantially inhibit a mammalian β-hexosaminidase.

In alternative embodiments, a compound according to Formula (Ia) or Formula (Ib) may have enhanced permeability.

In alternative aspects, the invention provides a pharmaceutical composition including a compound according to the invention, in combination with a pharmaceutically acceptable carrier.

In alternative aspects, the invention provides methods of selectively inhibiting an O-GlcNAcase, or of inhibiting an O-GlcNAcase in a subject in need thereof, or of increasing the level of O-GlcNAc, or of treating a neurodegenerative disease, a tauopathy, cancer or stress, in a subject in need thereof, by administering to the subject an effective amount of a compound of Formula (I) or a pharmaceutically acceptable salt thereof:

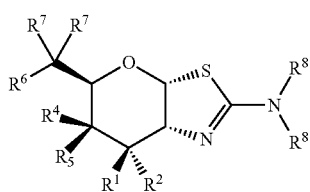 (I)

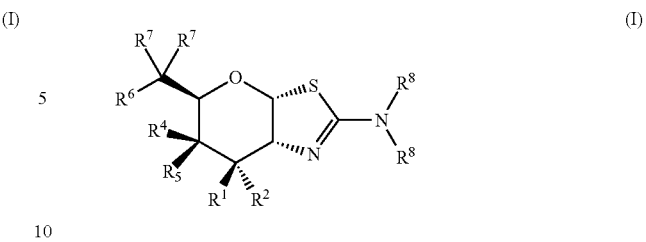 (I)

where $R^1$ and $R^2$ may be H, or $R^1$ may be H and $R^2$ may be F, or $R^1$ may be F and $R^2$ may be H, or $R^1$ may be $OR^3$ and $R^2$ may be H; each $R^3$ may be independently H or $C_{1-6}$ acyl; $R^4$ may be H and $R^5$ may be $OR^3$, or $R^4$ may be $OR^3$ and $R^5$ may be H; $R^6$ may be H, F, or $OR^3$; each $R^7$ may be independently H or F; each $R^8$ may be independently selected from the group consisting of: H, $C_{1-6}$ alkyl, $C_{3-6}$ alkenyl, $C_{3-6}$ alkynyl, and $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl, or the two $R^8$ groups may be connected together with the nitrogen atom to which they are attached to form a ring, said ring optionally independently substituted from one up to the maximum number of substituents with one or more of fluoro, OH, or methyl; with the proviso that when $R^6$ is $OR^3$, each $R^7$ is H; and with the proviso that either $R^1$ or $R^6$ is other than $OR^3$. The condition may be Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, Huntington's disease, Parkinson's disease, Schizophrenia, Mild Cognitive Impairment (MCI), Neuropathy (including peripheral neuropathy, autonomic neuropathy, neuritis, and diabetic neuropathy), or Glaucoma. The stress may be a cardiac disorder, e.g., ischemia; hemorrhage; hypovolemic shock; myocardial infarction; an interventional cardiology procedure; cardiac bypass surgery; fibrinolytic therapy; angioplasty; or stent placement.

In alternative aspects, the invention provides a method of treating an O-GlcNAcase-mediated condition that excludes a neurodegenerative disease, a tauopathy, cancer or stress, in a subject in need thereof, by administering to the subject an effective amount of a compound of Formula (I) or a pharmaceutically acceptable salt thereof:

where $R^1$ and $R^2$ may be H, or $R^1$ may be H and $R^2$ may be F, or $R^1$ may be F and $R^2$ may be H, or $R^1$ may be $OR^3$ and $R^2$ may be H; each $R^3$ may be independently H or $C_{1-6}$ acyl; $R^4$ may be H and $R^5$ may be $OR^3$, or $R^4$ may be $OR^3$ and $R^5$ may be H; $R^6$ may be H, F, or $OR^3$; each $R^7$ may be independently H or F; each $R^8$ may be independently selected from the group consisting of: H, $C_{1-6}$ alkyl, $C_{3-6}$ alkenyl, $C_{3-6}$ alkynyl, and $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl, or the two $R^8$ groups may be connected together with the nitrogen atom to which they are attached to form a ring, said ring optionally independently substituted from one up to the maximum number of substituents with one or more of fluoro, OH, or methyl; with the proviso that when $R^6$ is $OR^3$, each $R^7$ is H; and with the proviso that either $R^1$ or $R^6$ is other than $OR^3$. In some embodiments, the condition may be inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, Guillain-Barré syndrome, systemic lupus erythematosus, myastenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, and eosiniphilic fasciitis; graft rejection, in particular but not limited to solid organ transplants, such as heart, lung, liver, kidney, and pancreas transplants (e.g. kidney and lung allografts); epilepsy; pain; fibromyalgia; stroke, e.g., neuroprotection following a stroke.

In alternative embodiments, $R^1$ and $R^2$ may be H, or $R^1$ may be H and $R^2$ may be F, or $R^1$ may be F and $R^2$ may be H, or $R^1$ may be $OR^3$ and $R^2$ may be H; each $R^3$ may be independently H or $C_{1-6}$ acyl; $R^4$ may be H and $R^5$ may be $OR^3$, or $R^4$ may be $OR^3$ and $R^5$ may be H; $R^6$ may be H, F, or $OR^3$; each $R^7$ may be independently H or F; each $R^8$ may be independently selected from the group consisting of: H, $C_{1-6}$ alkyl, $C_{3-6}$ alkenyl, $C_{3-6}$ alkynyl, and $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl, or the two $R^8$ groups may be connected together with the nitrogen atom to which they are attached to form a ring, said ring optionally independently substituted from one up to the maximum number of substituents with one or more of fluoro, OH, or methyl; with the proviso that when $R^6$ is $OR^3$, each $R^7$ is H; and with the proviso that either $R^1$ or $R^6$ is other than $OR^3$. The administering may increase the level of O-GlcNAc in the subject. The subject may be a human.

In alternative aspects, the invention provides use of a compound of an effective amount of a compound of Formula (I) or a pharmaceutically acceptable salt thereof:

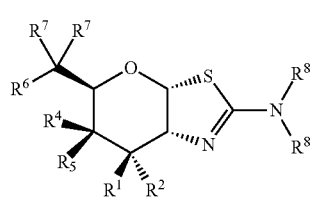

(I)

where $R^1$ and $R^2$ may be H, or $R^1$ may be H and $R^2$ may be F, or $R^1$ may be F and $R^2$ may be H, or $R^1$ may be $OR^3$ and $R^2$ may be H; each $R^3$ may be independently H or $C_{1-6}$ acyl; $R^4$ may be H and $R^5$ may be $OR^3$, or $R^4$ may be $OR^3$ and $R^5$ may be H; $R^6$ may be H, F, or $OR^3$; each $R^7$ may be independently H or F; each $R^8$ may be independently selected from the group consisting of: H, $C_{1-6}$ alkyl, $C_{3-6}$ alkenyl, $C_{3-6}$ alkynyl, and $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl, or the two $R^8$ groups may be connected together with the nitrogen atom to which they are attached to form a ring, said ring optionally independently substituted from one up to the maximum number of substituents with one or more of fluoro, OH, or methyl; with the proviso that when $R^6$ is $OR^3$, each $R^7$ is H; and with the proviso that either $R^1$ or $R^6$ is other than $OR^3$, in the preparation of a medicament. The medicament may be for selectively inhibiting an O-GlcNAcase, for increasing the level of O-GlcNAc, for treating a condition modulated by an O-GlcNAcase, for treating a neurodegenerative disease, a tauopathy, a cancer, or stress.

In alternative aspects, the invention provides a method for screening for a selective inhibitor of an O-GlcNAcase, by a) contacting a first sample with a test compound; b) contacting a second sample with a compound of Formula (I)

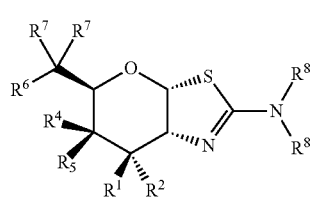

(I)

where $R^1$ and $R^2$ may be H, or $R^1$ may be H and $R^2$ may be F, or $R^1$ may be F and $R^2$ may be H, or $R^1$ may be $OR^3$ and $R^2$ may be H; each $R^3$ may be independently H or $C_{1-6}$ acyl; $R^4$ may be H and $R^5$ may be $OR^3$, or $R^4$ may be $OR^3$ and $R^5$ may be H; $R^6$ may be H, F, or $OR^3$; each $R^7$ may be independently H or F; each $R^8$ may be independently selected from the group consisting of: H, $C_{1-6}$ alkyl, $C_{3-6}$ alkenyl, $C_{3-6}$ alkynyl, and $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl, or the two $R^8$ groups may be connected together with the nitrogen atom to which they are attached to form a ring, said ring optionally independently substituted from one up to the maximum number of substituents with one or more of fluoro, OH, or methyl; with the proviso that when $R^6$ is $OR^3$, each $R^7$ is H; and with the proviso that either $R^1$ or $R^6$ is other than $OR^3$; c) determining the level of inhibition of the O-GlcNAcase in the first and second samples, where the test compound is a selective inhibitor of a O-GlcNAcase if the test compound exhibits the same or greater inhibition of the O-GlcNAcase when compared to the compound of Formula (I).

This summary of the invention does not necessarily describe all features of the invention.

DETAILED DESCRIPTION

The invention provides, in part, novel compounds that are capable of inhibiting an O-glycoprotein 2-acetamido-2-deoxy-β-D-glucopyranosidase (O-GlcNAcase). In some embodiments, the O-GlcNAcase is a mammalian O-GlcNAcase, such as a rat, mouse or human O-GlcNAcase.

In some embodiments, one or more of the compounds according to the invention exhibit enhanced permeability. Permeability can be assessed using a variety of standard experimental techniques, including without limitation in situ perfusion, ex vivo tissue diffusion, in vitro cell monolayers (e.g. Caco-2 cells, MDCK cells, LLC-PKI cells), and artificial cell membranes (e.g. PAMPA assay); suitable techniques for measuring effective permeability ($P_{eff}$) or apparent peameability ($P_{app}$) are reviewed for example by Volpe in The AAPS Journal, 2010, 12(4), 670-678. In some embodiments, one or more of the compounds according to the invention show enhanced permeability when tested in one or more of these assays for determining $P_{eff}$ or $P_{app}$. In some embodiments, a compound that exhibits enhanced permeability exhibits greater oral absorption. In some embodiments, a compound that exhibits enhanced permeability exhibits greater brain penetrance when administered in vivo. In some embodiments, a compound that exhibits enhanced permeability achieves higher brain concentrations when administered in vivo. In some embodiments, a compound that exhibits enhanced permeability exhibits a higher brain/plasma concentration ratio when administered in vivo. In some embodiments, "enhanced permeability" means an increase in measured $P_{eff}$ or $P_{app}$ by any value between 10% and 100%, or of any integer value between 10% and 100%, for example, 10%, 20%, 30%, 40%, 50%, 60%, 70%, 80%, 90%, 100%, or over 100%, or an increase by 1-fold, 2-fold, or 3-fold, or more, as compared to a suitable reference compound disclosed in for example WO 2006/092049 or WO 2008/025170. A suitable reference compound may be, for example, -(3aR,5R,6S,7R,7aR)-5-(hydroxymethyl)-2-propyl-5,6,7,7a-tetrahydro-3aH-pyrano[3,2-d]thiazole-6,7-diol, or -(3aR,5R,6S,7R,7aR)-2-(ethylamino)-5-(hydroxymethyl)-5,6,7,7a-tetrahydro-3aH-pyrano[3,2-d]thiazole-6,7-diol, or -(3aR,5R,6S,7R,7aR)-2-(dimethylamino)-5-(hydroxymethyl)-5,6,7,7a-tetrahydro-3aH-pyrano[3,2-d]thiazole-6,7-diol. In some embodiments, "enhanced permeability" means a measurable $P_{app}$ value (i.e. a value greater than zero) in the assay described below for determination of $P_{app}$ in LLC-PK1 cells. In some embodiments, "enhanced permeability" means a $P_{app}$ value greater than $2 \times 10^{-6}$ cm/s in the assay described below for determination of $P_{app}$ in LLC-PK1 cells. In some embodiments, "enhanced permeability" means a $P_{app}$ value greater than $1 \times 10^{-6}$ cm/s in the assay described below for determination of $P_{app}$ in LLC-PK1 cells. In alternative embodiments, "enhanced permeability" means a $P_{app}$ value in the range $2 \times 10^{-6}$ cm/s to $30 \times 10^{-6}$ cm/s in the assay described below for determination of $P_{app}$ in LLC-PK1 cells.

In some embodiments, a compound according to the invention exhibits superior selectivity in inhibiting an O-GlcNAcase. In some embodiments, one or more of the compounds according to the invention are more selective for an O-GlcNAcase over a β-hexosaminidase. In some embodiments, one or more of the compounds selectively inhibit the activity of a mammalian O-GlcNAcase over a mammalian β-hexosaminidase. In some embodiments, a selective inhibitor of an O-GlcNAcase does not substantially inhibit a β-hexosaminidase. In some embodiments, the β-hexosaminidase is a mammalian β-hexosaminidase, such as a rat, mouse or human β-hexosaminidase. A compound that "selectively" inhibits an O-GlcNAcase is a compound that inhibits the activity or biological function of an O-GlcNAcase, but does not substantially inhibit the activity or biological function of a β-hexosaminidase. For example, in some embodiments, a selective inhibitor of an O-GlcNAcase selectively inhibits the cleavage of 2-acetamido-2-deoxy-β-D-glucopyranoside (O-GlcNAc) from polypeptides. In some embodiments, a selective inhibitor of an O-GlcNAcase selectively binds to an O-GlcNAcase. In some embodiments, a selective inhibitor of an O-GlcNAcase inhibits hyperphosphorylation of a tau protein and/or inhibits formations of NFTs. By "inhibits," "inhibition" or "inhibiting" means a decrease by any value between 10% and 90%, or of any integer value between 30% and 60%, or over 100%, or a decrease by 1-fold, 2-fold, 5-fold, 10-fold or more. It is to be understood that the inhibiting does not require full inhibition. In some embodiments, a selective inhibitor of an O-GlcNAcase elevates or enhances O-GlcNAc levels e.g., O-GlcNAc-modified polypeptide or protein levels, in cells, tissues, or organs (e.g., in brain, muscle, or heart (cardiac) tissue) and in animals. By "elevating" or "enhancing" is meant an increase by any value between 10% and 90%, or of any integer value between 30% and 60%, or over 100%, or an increase by 1-fold, 2-fold, 5-fold, 10-fold, 15-fold, 25-fold, 50-fold, 100-fold or more. In some embodiments, a selective inhibitor of an O-GlcNAcase exhibits a selectivity ratio, as described herein, in the range 10 to 100000, or in the range 100 to 100000, or in the range 1000 to 100000, or at least 10, 20, 50, 100, 200, 500, 1000, 1500, 2000, 2500, 3000, 3500, 4000, 4500, 5000, 6000, 7000, 10,000, 25,000, 50,000, 75,000, or any value within or about the described range.

One or more of the compounds of the present invention elevate O-GlcNAc levels on O-GlcNAc-modified polypeptides or proteins in vivo specifically via interaction with an O-GlcNAcase enzyme, and are effective in treating conditions which require or respond to inhibition of O-GlcNAcase activity.

In some embodiments, one or more of the compounds of the present invention are useful as agents that produce a decrease in tau phosphorylation and NFT formation. In some embodiments, one or more of the compounds are therefore useful to treat Alzheimer's disease and related tauopathies. In some embodiments, one or more of the compounds are thus capable of treating Alzheimer's disease and related tauopathies by lowering tau phosphorylation and reducing NFT formation as a result of increasing tau O-GlcNAc levels. In some embodiments, one or more of the compounds produce an increase in levels of O-GlcNAc modification on O-GlcNAc-modified polypeptides or proteins, and are therefore useful for treatment of disorders responsive to such increases in O-GlcNAc modification; these disorders include without limitation neurodegenerative, inflammatory, cardiovascular, and immunoregulatory diseases. In some embodiments, a compound is also useful as a result of other biological activites related to their ability to inhibit the activity of glycosidase enzymes. In alternative embodiments, one or more of the compounds of the invention are valuable tools in studying the physiological role of O-GlcNAc at the cellular and organismal level.

In alternative embodiments, the invention provides methods of enhancing or elevating levels of protein O-GlcNAc modification in animal subjects, such as, veterinary and human subjects. In alternative embodiments, the invention provides methods of selectively inhibiting an O-GlcNAcase enzyme in animal subjects, such as, veterinary and human subjects. In alternative embodiments, the invention provides methods of inhibiting phosphorylation of tau polypeptides, or inhibiting formation of NFTs, in animal subjects, such as, veterinary and human subjects.

In specific embodiments, the invention provides compounds described generally by Formula (I) and the salts, prodrugs, and enantiomeric forms thereof:

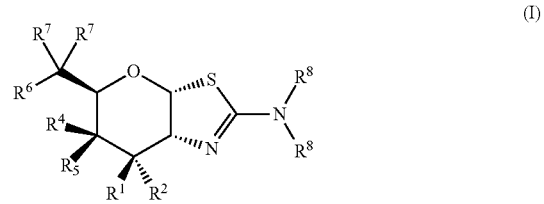

(I)

As set forth in Formula (I): $R^1$ and $R^2$ may be H, or $R^1$ may be H and $R^2$ may be F, or $R^1$ may be F and $R^2$ may be H, or $R^1$ may be $OR^3$ and $R^2$ may be H; each $R^3$ may be independently H or $C_{1-6}$ acyl; $R^4$ may be H and $R^5$ may be $OR^3$, or $R^4$ may be $OR^3$ and $R^5$ may be H; $R^6$ may be H, F, or $OR^3$; each $R^7$ may be independently H or F; each $R^8$ may be independently selected from the group consisting of: H, $C_{1-6}$ alkyl, $C_{3-6}$ alkenyl, $C_{3-6}$ alkynyl, and $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl, or the two $R^8$ groups may be connected together with the nitrogen atom to which they are attached to form a ring, said ring optionally independently substituted from one up to the maximum number of substituents with one or more of fluoro, OH, or methyl; with the proviso that when $R^6$ is $OR^3$, each $R^7$ is H; and with the proviso that either $R^1$ or $R^6$ is other than $OR^3$.

In some embodiments, $R^1$ as set forth in Formula (I) may be H, F, OH, or $OC(O)R^9$, where $R^9$ may be H, $C_{1-6}$ alkyl, or $C_{3-6}$ cycloalkyl. In some embodiments, $R^1$ may be H, F or OH.

In some embodiments, $R^2$ as set forth in Formula (I) may be H or F.

In some embodiments, $R^3$ as set forth in Formula (I) may be H or $C(O)R^9$, where $R^9$ may be H, $C_{1-6}$ alkyl, or $C_{3-6}$ cycloalkyl. In some embodiments, $R^3$ may be H.

In some embodiments, $R^4$ as set forth in Formula (I) may be H, OH, or $OC(O)R^9$, where $R^9$ may be H, $C_{1-6}$ alkyl, or $C_{3-6}$ cycloalkyl. In some embodiments, $R^4$ may be H or OH.

In some embodiments, $R^5$ as set forth in Formula (I) may be H, OH, or OC(O)$R^9$, where $R^9$ may be H, $C_{1-6}$ alkyl, or $C_{3-6}$ cycloalkyl. In some embodiments, $R^5$ may be H or OH.

In some embodiments, $R^6$ as set forth in Formula (I) may be H, F, OH, or OC(O)$R^9$, where $R^9$ may be H, $C_{1-6}$ alkyl, or $C_{3-6}$ cycloalkyl. In some embodiments, $R^6$ may be H, F, or OH.

In some embodiments, each $R^7$ as set forth in Formula (I) may be independently H or F.

In some embodiments, each $R^8$ as set forth in Formula (I) may be independently H, $C_{1-6}$ alkyl, $C_{3-6}$ alkenyl, $C_{3-6}$ alkynyl, or $C_{1-6}$ alkoxy, where the $C_{1-6}$ alkyl, $C_{3-6}$ alkenyl, $C_{3-6}$ alkynyl, or $C_{1-6}$ alkoxy may be optionally substituted from one up to the maximum number of substituents with one or more of fluoro, OH, or methyl. In some embodiments, each $R^8$ may be independently H, $CH_3$, $CH_2CH_3$, $(CH_2)_2CH_3$, $CH_2CH=CH_2$, or $CH_2C\equiv CH$.

In some embodiments, the two $R^8$ groups as set forth in Formula (I) may be connected together with the nitrogen atom to which they are attached to form a ring, said ring optionally independently substituted from one up to the maximum number of substituents with one or more of fluoro, OH, or methyl.

In some embodiments, $NR^8_2$ as set forth in Formula (I), may be optionally substituted

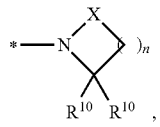

where X may be $CR^{10}_2$, $NR^{10}$, O, C=O, O(C=O), (C=O)O, $NR^{10}$(C=O), or (C=O)$NR^{10}$; where each $R^{10}$ may be independently H or $C_{1-4}$ alkyl; and n may be an integer between 0 and 3. In some embodiments, $NR^8_2$ may be optionally substituted 1-aziridinyl, 1-azetidinyl, 1-pyrrolidinyl, 1-piperidinyl, morpholin-4-yl, 1-piperizinyl, azetidin-2-one-1-yl, pyrrolidin-2-one-1-yl, or piperid-2-one-1-yl. In some embodiments, $NR^8_2$ may be

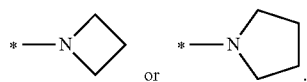

In specific embodiments of the invention, compounds according to Formula (I) include the compounds described in Table 1.

TABLE 1

| Example | Name | Structure |
|---|---|---|
| 1 | (3aR,5R,6S,7R,7aR)-2-(ethylamino)-5-methyl-5,6,7,7a-tetrahydro-3aH-pyrano[3,2-d]thiazole-6,7-diol | 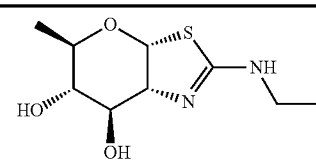 |
| 2 | (3aR,5R,6S,7aR)-2-(ethylamino)-5-(hydroxymethyl)-5,6,7,7a-tetrahydro-3aH-pyrano[3,2-d]thiazol-6-ol | 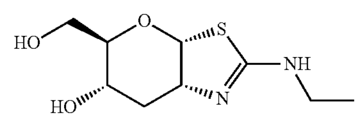 |
| 3 | (3aR,5R,6S,7aR)-5-(hydroxymethyl)-2-(methylamino)-5,6,7,7a-tetrahydro-3aH-pyrano[3,2-d]thiazol-6-ol | 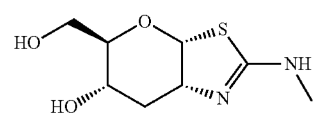 |
| 4 | (3aR,5R,6S,7aR)-2-(dimethylamino)-5-(hydroxymethyl)-5,6,7,7a-tetrahydro-3aH-pyrano[3,2-d]thiazol-6-ol | 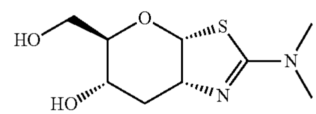 |
| 5 | (3aR,5R,6S,7aR)-2-amino-5-(hydroxymethyl)-5,6,7,7a-tetrahydro-3aH-pyrano[3,2-d]thiazol-6-ol | 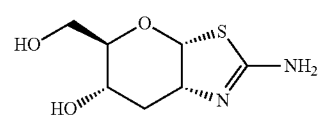 [SMILES: NC1=N[C@@H]2C[C@H](O)[C@@H](CO)O[C@@H]2S1] |
| 6 | (3aR,5R,6S,7aR)-5-(hydroxymethyl)-2-(propylamino)-5,6,7,7a-tetrahydro-3aH-pyrano[3,2-d]thiazol-6-ol | 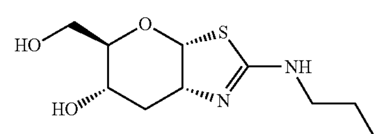 |
| 7 | (3aR,5R,6R,7R,7aR)-2-(ethylamino)-7-fluoro-5-(hydroxymethyl)-5,6,7,7a-tetrahydro-3aH-pyrano[3,2-d]thiazol-6-ol | 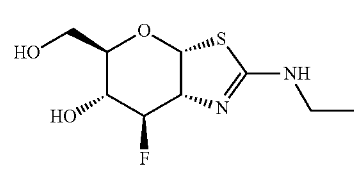 [SMILES: CCNC1=N[C@@H]2[C@@H](F)[C@H](O)[C@@H](CO)O[C@@H]2S1] |

| Example | Name | Structure |
|---|---|---|
| 8 | (3aR,5R,6R,7R,7aR)-2-(dimethylamino)-7-fluoro-5-(hydroxymethyl)-5,6,7,7a-tetrahydro-3aH-pyrano[3,2-d]thiazol-6-ol | 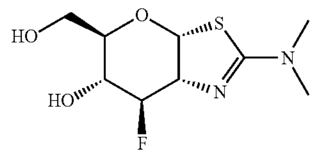 [SMILES: CN(C)C1=N[C@@H]2[C@@H](F)[C@H](O)[C@@H](CO)O[C@@H]2S1] |
| 9 | (3aR,5R,6R,7R,7aR)-7-fluoro-5-(hydroxymethyl)-2-(methylamino)-5,6,7,7a-tetrahydro-3aH-pyrano[3,2-d]thiazol-6-ol | 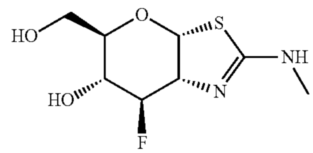 |
| 10 | (3aR,5R,6R,7R,7aR)-7-fluoro-5-(hydroxymethyl)-2-(propylamino)-5,6,7,7a-tetrahydro-3aH-pyrano[3,2-d]thiazol-6-ol | 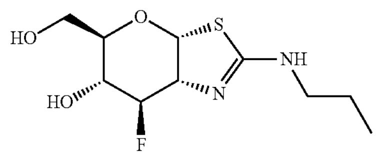 [SMILES: CCCNC1=N[C@@H]2[C@@H](F)[C@H](O)[C@@H](CO)O[C@@H]2S1] |
| 11 | (3aR,5R,6R,7S,7aR)-7-fluoro-5-(hydroxymethyl)-2-(methylamino)-5,6,7,7a-tetrahydro-3aH-pyrano[3,2-d]thiazol-6-ol | 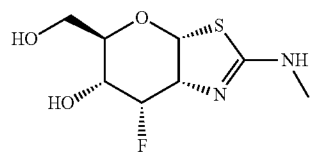 |
| 12 | (3aR,5S,6S,7R,7aR)-2-(ethylamino)-5-(fluoromethyl)-5,6,7,7a-tetrahydro-3aH-pyrano[3,2-d]thiazole-6,7-diol | 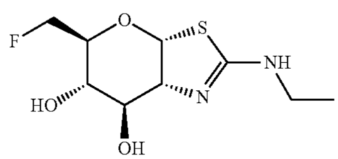 [SMILES: CCNC1=N[C@@H]2[C@@H](O)[C@H](O)[C@@H](CF)O[C@@H]2S1] |
| 13 | (3aR,5S,6S,7R,7aR)-2-(dimethylamino)-5-(fluoromethyl)-5,6,7,7a-tetrahydro-3aH-pyrano[3,2-d]thiazole-6,7-diol | 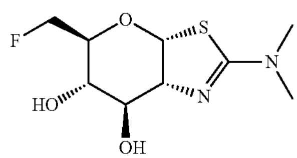 [SMILES: CN(C)C1=N[C@@H]2[C@@H](O)[C@H](O)[C@@H](CF)O[C@@H]2S1] |
| 14 | (3aR,5S,6S,7R,7aR)-2-(allylamino)-5-(fluoromethyl)-5,6,7,7a-tetrahydro-3aH-pyrano[3,2-d]thiazole-6,7-diol | 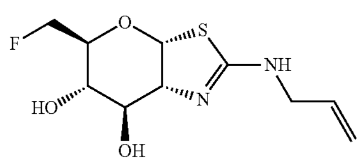 [SMILES: C=CCNC1=N[C@@H]2[C@@H](O)[C@H](O)[C@@H](CF)O[C@@H]2S1] |
| 15 | (3aR,5S,6S,7R,7aR)-2-amino-5-(fluoromethyl)-5,6,7,7a-tetrahydro-3aH-pyrano[3,2-d]thiazole-6,7-diol | 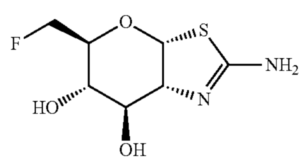 [SMILES: NC1=N[C@@H]2[C@@H](O)[C@H](O)[C@@H](CF)O[C@@H]2S1] |
| 16 | (3aR,5S,6S,7R,7aR)-2-(azetidin-1-yl)-5-(fluoromethyl)-5,6,7,7a-tetrahydro-3aH-pyrano[3,2-d]thiazole-6,7-diol | 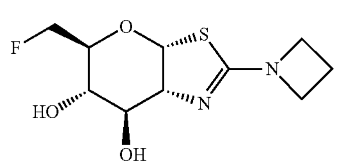 [SMILES: O[C@H]1[C@H](O)[C@@H](CF)O[C@@H]2SC(N3CCC3)=N[C@H]12] |
| 17 | (3aR,5S,6S,7R,7aR)-5-(fluoromethyl)-2-(methylamino)-5,6,7,7a-tetrahydro-3aH-pyrano[3,2-d]thiazole-6,7-diol | 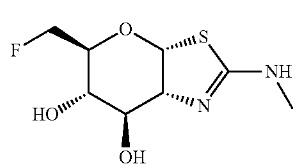 |

TABLE 1-continued

| Example | Name | Structure |
|---|---|---|
| 18 | (3aR,5S,6S,7R,7aR)-5-(fluoromethyl)-2-(propylamino)-5,6,7,7a-tetrahydro-3aH-pyrano[3,2-d]thiazole-6,7-diol | 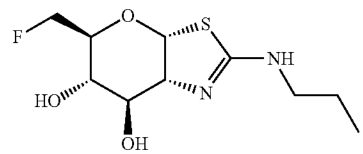 [SMILES: CCCNC1=N[C@@H]2[C@@H](O)[C@H](O)[C@@H](CF)O[C@@H]2S1] |
| 19 | (3aR,5S,6S,7R,7aR)-5-(difluoromethyl)-2-(ethylamino)-5,6,7,7a-tetrahydro-3aH-pyrano[3,2-d]thiazole-6,7-diol | 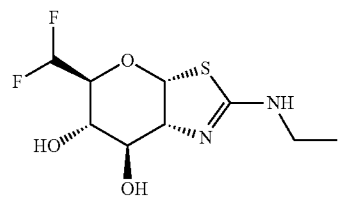 [SMILES: CCNC1=N[C@@H]2[C@@H](O)[C@H](O)[C@@H](C(F)F)O[C@@H]2S1] |
| 20 | (3aR,5S,6S,7R,7aR)-5-(difluoromethyl)-2-(dimethylamino)-5,6,7,7a-tetrahydro-3aH-pyrano[3,2-d]thiazole-6,7-diol | 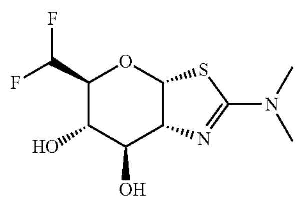 [SMILES: CN(C)C1=N[C@@H]2[C@@H](O)[C@H](O)[C@@H](C(F)F)O[C@@H]2S1] |
| 21 | (3aR,5S,6S,7R,7aR)-2-(allylamino)-5-(difluoromethyl)-5,6,7,7a-tetrahydro-3aH-pyrano[3,2-d]thiazole-6,7-diol | 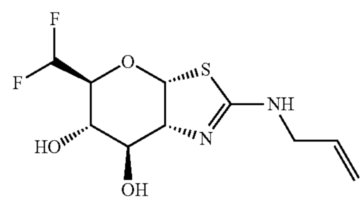 [SMILES: C=CCNC1=N[C@@H]2[C@@H](O)[C@H](O)[C@@H](C(F)F)O[C@@H]2S1] |
| 22 | (3aR,5S,6S,7R,7aR)-2-amino-5-(difluoromethyl)-5,6,7,7a-tetrahydro-3aH-pyrano[3,2-d]thiazole-6,7-diol | 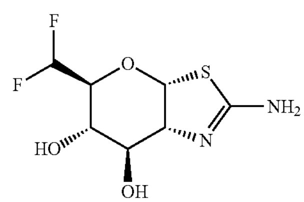 [SMILES: NC1=N[C@@H]2[C@@H](O)[C@H](O)[C@@H](C(F)F)O[C@@H]2S1] |
| 23 | (3aR,5S,6S,7R,7aR)-5-(difluoromethyl)-2-(prop-2-yn-1-ylamino)-5,6,7,7a-tetrahydro-3aH-pyrano[3,2-d]thiazole-6,7-diol | 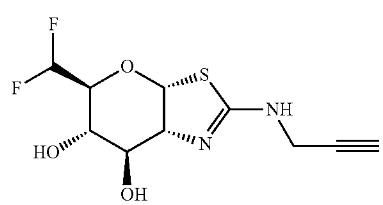 [SMILES: C#CCNC1=N[C@@H]2[C@@H](O)[C@H](O)[C@@H](C(F)F)O[C@@H]2S1] |
| 24 | (3aR,5S,6S,7R,7aR)-2-(azetidin-1-yl)-5-(difluoromethyl)-5,6,7,7a-tetrahydro-3aH-pyrano[3,2-d]thiazole-6,7-diol | 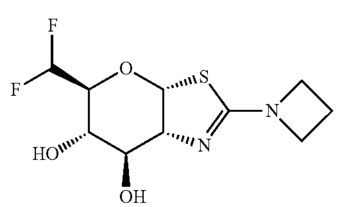 [SMILES: O[C@H]1[C@H](O)[C@@H](C(F)F)O[C@@H]2SC(N3CCC3)=N[C@H]12] |
| 25 | (3aR,5S,6S,7R,7aR)-5-(difluoromethyl)-2-(methylamino)-5,6,7,7a-tetrahydro-3aH-pyrano[3,2-d]thiazole-6,7-diol | 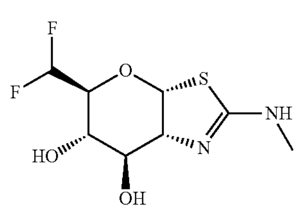 [SMILES: CNC1=N[C@@H]2[C@@H](O)[C@H](O)[C@@H](C(F)F)O[C@@H]2S1] |

TABLE 1-continued

| Example | Name | Structure |
|---|---|---|
| 26 | (3aR,5S,6S,7R,7aR)-5-(difluoromethyl)-2-(propylamino)-5,6,7,7a-tetrahydro-3aH-pyrano[3,2-d]thiazole-6,7-diol | 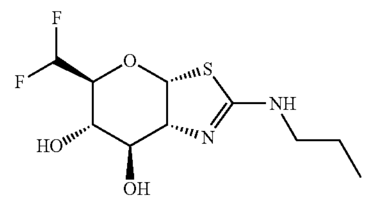 [SMILES: CCCNC1=N[C@@H]2[C@@H](O)[C@H](O)[C@@H](C(F)F)O[C@@H]2S1] |
| 27 | (3aR,5S,6S,7aR)-5-(difluoromethyl)-2-(methylamino)-5,6,7,7a-tetrahydro-3aH-pyrano[3,2-d]thiazol-6-ol | 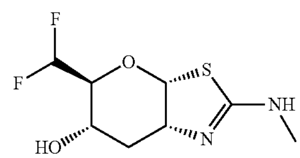 |
| 28 | (3aR,5S,6S,7aR)-5-(difluoromethyl)-2-(dimethylamino)-5,6,7,7a-tetrahydro-3aH-pyrano[3,2-d]thiazol-6-ol | 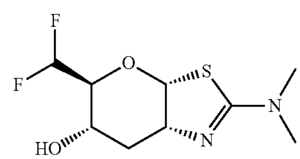 [SMILES: CN(C)C1=N[C@@H]2C[C@H](O)[C@@H](C(F)F)O[C@@H]2S1] |
| 29 | (3aR,5S,6R,7R,7aR)-5-(difluoromethyl)-2-(ethylamino)-5,6,7,7a-tetrahydro-3aH-pyrano[3,2-d]thiazole-6,7-diol | 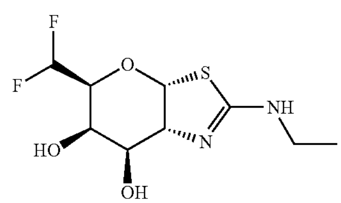 [SMILES: CCNC1=N[C@@H]2[C@@H](O)[C@@H](O)[C@@H](C(F)F)O[C@@H]2S1] |
| 30 | (3aR,5R,6S,7R,7aR)-7-fluoro-5-(hydroxymethyl)-2-(methylamino)-5,6,7,7a-tetrahydro-3aH-pyrano[3,2-d]thiazol-6-ol | 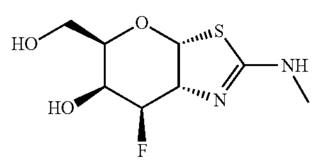 |
| 31 | (3aR,5S,6R,7R,7aR)-7-fluoro-5-(fluoromethyl)-2-(methylamino)-5,6,7,7a-tetrahydro-3aH-pyrano[3,2-d]thiazol-6-ol | 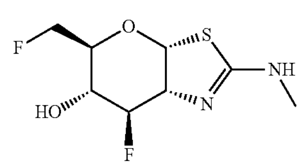 |
| 32 | (3aR,5S,6R,7R,7aR)-5-(difluoromethyl)-7-fluoro-2-(methylamino)-5,6,7,7a-tetrahydro-3aH-pyrano[3,2-d]thiazol-6-ol | 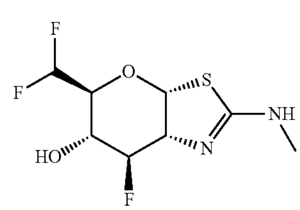 [SMILES: CNC1=N[C@@H]2[C@@H](F)[C@H](O)[C@@H](C(F)F)O[C@@H]2S1] |
| 33 | (3aR,5S,6R,7S,7aR)-5-(difluoromethyl)-7-fluoro-2-(methylamino)-5,6,7,7a-tetrahydro-3aH-pyrano[3,2-d]thiazol-6-ol | 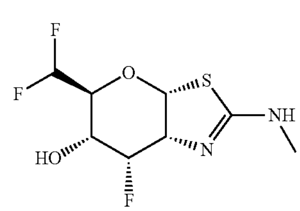 [SMILES: CNC1=N[C@@H]2[C@H](F)[C@H](O)[C@@H](C(F)F)O[C@@H]2S1] |

TABLE 1-continued

| Example | Name | Structure |
|---|---|---|
| 34 | (3aR,5R,6R,7S,7aR)-2-(ethylamino)-7-fluoro-5-(hydroxymethyl)-5,6,7,7a-tetrahydro-3aH-pyrano[3,2-d]thiazol-6-ol | 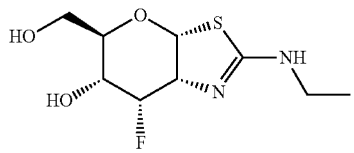 [SMILES: CCNC1=N[C@@H]2[C@H](F)[C@H](O)[C@@H](CO)O[C@@H]2S1] |
| 35 | (3aR,5R,6R,7S,7aR)-2-(dimethylamino)-7-fluoro-5-(hydroxymethyl)-5,6,7,7a-tetrahydro-3aH-pyrano[3,2-d]thiazol-6-ol | 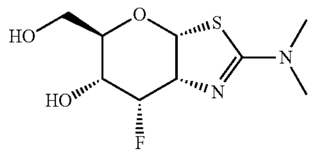 [SMILES: CN(C)C1=N[C@@H]2[C@H](F)[C@H](O)[C@@H](CO)O[C@@H]2S1] |
| 36 | (3aR,5R,6R,7S,7aR)-7-fluoro-5-(hydroxymethyl)-2-(propylamino)-5,6,7,7a-tetrahydro-3aH-pyrano[3,2-d]thiazol-6-ol | 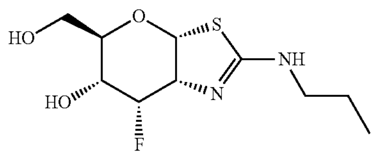 [SMILES: CCCNC1=N[C@@H]2[C@H](F)[C@H](O)[C@@H](CO)O[C@@H]2S1] |
| 37 | (3aR,5R,6R,7S,7aR)-7-fluoro-5-(hydroxymethyl)-2-(isobutylamino)-5,6,7,7a-tetrahydro-3aH-pyrano[3,2-d]thiazol-6-ol | 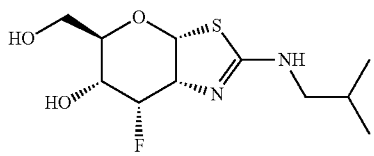 [SMILES: CC(C)CNC1=N[C@@H]2[C@H](F)[C@H](O)[C@@H](CO)O[C@@H]2S1] |
| 38 | (3aR,5S,6R,7R,7aR)-5-(difluoromethyl)-7-fluoro-2-(((E)-3-fluoro-2-methylallyl)amino)-5,6,7,7a-tetrahydro-3aH-pyrano[3,2-d]thiazol-6-ol | 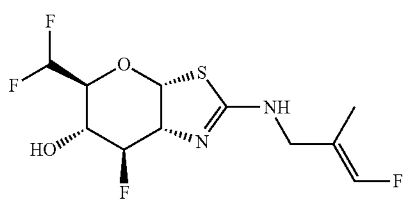 [SMILES: C/C(=C\F)CNC1=N[C@@H]2[C@@H](F)[C@H](O)[C@@H](C(F)F)O[C@@H]2S1] |
| 39 | (3aR,5S,6S,7R,7aR)-5-(fluoromethyl)-2-((4-hydroxybut-2-yn-1-yl)amino)-5,6,7,7a-tetrahydro-3aH-pyrano[3,2-d]thiazole-6,7-diol | 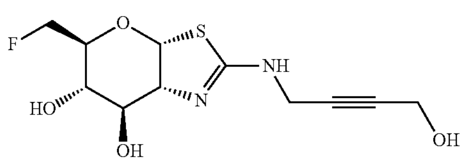 |
| 40 | (3aR,5S,6S,7aR)-2-((2,2-difluoroethoxy)(methyl)amino)-5-(difluoromethyl)-5,6,7,7a-tetrahydro-3aH-pyrano[3,2-d]thiazol-6-ol | 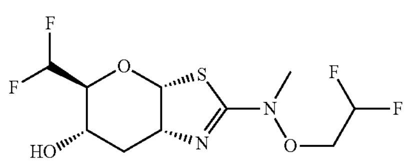 [SMILES: CN(OCC(F)F)C1=N[C@@H]2C[C@H](O)[C@@H](C(F)F)O[C@@H]2S1] |
| 41 | (3aR,5S,6R,7S,7aR)-7-fluoro-2-(3-fluoroazetidin-1-yl)-5-(fluoromethyl)-5,6,7,7a-tetrahydro-3aH-pyrano[3,2-d]thiazol-6-ol | 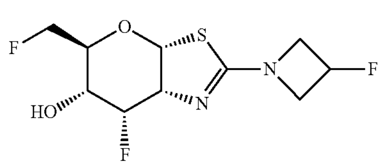 [SMILES: O[C@H]1[C@@H](F)[C@H]2N=C(N3CC(F)C3)S[C@H]2O[C@@H]1CF] |
| 42 | (3aR,5R,6S,7S,7aR)-2-(3,3-difluoroazetidin-1-yl)-7-fluoro-5-methyl-5,6,7,7a-tetrahydro-3aH-pyrano[3,2-d]thiazol-6-ol | 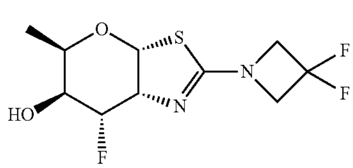 [SMILES: C[C@H]1O[C@@H]2SC(N3CC(F)(F)C3)=N[C@@H]2[C@H](F)[C@H]1O] |

As will be appreciated by a person skilled in the art, Formula (I) above may also be represented alternatively as follows:

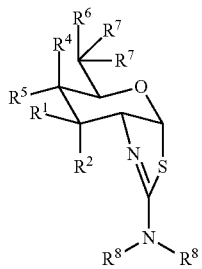

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Throughout this application, it is contemplated that the term "compound" or "compounds" refers to the compounds discussed herein and includes precursors and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Certain groups may be optionally substituted as described herein. Suitable substituents include: H, alkyl ($C_{1-6}$), alkenyl ($C_{2-6}$), or alkynyl ($C_{2-6}$) each of which may optionally contain one or more heteroatoms selected from O, S, P, N, F, Cl, Br, I, or B, and each of which may be further substituted, for example, by =O; or optionally substituted forms of acyl, alkyl- alkenyl-, or alkynyl- and forms thereof which contain heteroatoms in the alkyl, alkenyl, or alkynyl moieties. Other suitable substituents include =O, =NR, halo, CN, $CF_3$, $CHF_2$, $NO_2$, OR, SR, $NR_2$, $N_3$, COOR, and $CONR_2$, where R is H or alkyl, cycloalkyl, alkenyl, or alkynyl. Where the substituted atom is C, the substituents may include, in addition to the substituents listed above, halo, OOCR, NROCR, where R is H or a substituent set forth above.

For example, in the above Formula (I), each $C_{1-6}$ acyl, $C_{1-6}$ alkyl, $C_{3-6}$ alkenyl, $C_{3-6}$ alkynyl, or $C_{1-6}$ alkoxy group may be independently optionally substituted with one or more substituents. In some embodiments, each $C_{1-6}$ acyl, $C_{1-6}$ alkyl, $C_{3-6}$ alkenyl, $C_{3-6}$ alkynyl, or $C_{1-6}$ alkoxy group in Formula (I) may be substituted with one or more inorganic substituents; phosphoryl; halo; =O; =$NR^9$; OR; $C_{1-6}$ alkyl or $C_{2-6}$ alkenyl optionally containing one or more P, N, O, S, N, F, Cl, Br, I, or B, and optionally substituted with halo; CN; optionally substituted carbonyl; $NR^9{}_2$; C=$NR^9$; an optionally substituted carbocyclic or heterocyclic ring, where $R^9$ may be H, $C_{1-6}$ alkyl, or $C_{3-6}$ cycloalkyl. In alternative embodiments, each $C_{1-6}$ acyl, $C_{1-6}$ alkyl, $C_{3-6}$ alkenyl, $C_{3-6}$ alkynyl, or $C_{1-6}$ alkoxy group may be optionally substituted from one up to the maximum number of substituents with one or more of fluoro, OH, or methyl. In alternative embodiments, each optionally substituted $C_{1-6}$ acyl, $C_{1-6}$ alkyl, $C_{3-6}$ alkenyl, $C_{3-6}$ alkynyl, and $C_{1-6}$ alkoxy group in Formula (I) may independently include one or more heteroatoms selected from P, O, S, N, F, Cl, Br, I, or B.

"Alkyl" refers to a straight or branched hydrocarbon chain group consisting solely of carbon and hydrogen atoms, containing no unsaturation and including, for example, from one to ten carbon atoms, such as 1, 2, 3, 4, 5, 6, 7, 8, 9, or 10 carbon atoms, and which is attached to the rest of the molecule by a single bond. Unless stated otherwise specifically in the specification, the alkyl group may be optionally substituted by one or more substituents as described herein. Unless stated otherwise specifically herein, it is understood that the substitution can occur on any carbon of the alkyl group.

"Alkenyl" refers to a straight or branched hydrocarbon chain group consisting solely of carbon and hydrogen atoms, containing at least one double bond and including, for example, from two to ten carbon atoms, such as 2, 3, 4, 5, 6, 7, 8, 9, or 10 carbon atoms, and which is attached to the rest of the molecule by a single bond or a double bond. Unless stated otherwise specifically in the specification, the alkenyl group may be optionally substituted by one or more substituents as described herein. Unless stated otherwise specifically herein, it is understood that the substitution can occur on any carbon of the alkenyl group.

"Alkynyl" refers to a straight or branched hydrocarbon chain group consisting solely of carbon and hydrogen atoms, containing at least one triple bond and including, for example, from two to ten carbon atoms. Unless stated otherwise specifically in the specification, the alkenyl group may be optionally substituted by one or more substituents as described herein.

"Aryl" refers to a phenyl group, an aromatic ring including 6 carbon atoms. Unless stated otherwise specifically herein, the term "aryl" is meant to include aryl groups optionally substituted by one or more substituents as described herein.

"Heteroaryl" refers to a single aromatic ring group containing one or more heteroatoms in the ring, for example N, O, S, including for example, 5-6 members, such as 5 or 6 members. Examples of heteroaryl groups include furan, thiophene, pyrrole, oxazole, thiazole, imidazole, pyrazole, isoxazole, isothiazole, 1,2,3-oxadiazole, 1,2,3-triazole, 1,2, 4-triazole, 1,3,4-thiadiazole, tetrazole, pyridine, pyridazine, pyrimidine, pyrazine, 1,3,5-triazine, imidazole. Unless stated otherwise specifically herein, the term "heteroaryl" is meant to include heteroaryl groups optionally substituted by one or more substituents as described herein.

"Acyl" refers to a group of the formula —C(O)$R_a$, where $R_a$ is a $C_{1-10}$ alkyl or $C_{3-15}$ cycloalkyl group as described herein. The alkyl or cycloalkyl group(s) may be optionally substituted as described herein.

"Alkoxy" refers to a group of the formula —O$R_b$, where $R_b$ is a $C_{1-10}$ alkyl group as described herein. The alkyl group(s) may be optionally substituted as described herein.

"Cycloalkyl" refers to a stable monovalent monocyclic, bicyclic or tricyclic hydrocarbon group consisting solely of carbon and hydrogen atoms, having for example from 3 to 15 carbon atoms, and which is saturated and attached to the rest of the molecule by a single bond. Unless otherwise stated specifically herein, the term "cycloalkyl" is meant to include cycloalkyl groups which are optionally substituted as described herein.

"Halo" refers to bromo, chloro, fluoro, iodo, etc. In some embodiments, suitable halogens include fluorine or chlorine.

In some embodiments, two $R^8$ groups as set forth in Formula (I) may be connected together with the nitrogen atom to which they are attached to form a ring. In these embodiments, "ring" refers to a stable nitrogen-containing monocyclic group having 3 to 6 members that may be saturated or monounsaturated. In alternative embodiments, the ring may include C, H and N atoms. In other embodiments, the ring may include heteroatoms, for example O and S. Examples of a ring in these embodiments include 1-aziridinyl, 1-azetidinyl, 1-pyrrolidinyl, 2,5-dihydro-1H-pyrrol-1-yl, 1-piperidinyl, 1,2,3,6-tetrahydropyridin-1-yl, morpholin-4-yl, thiomorpholin-4-yl, 1-piperizinyl, azetidin-2-one-1-yl, pyrrolidin-2-one-1-yl, piperid-2-one-1-yl, 1,2-oxazetidin-2-yl, isoxazolidin-2-yl, and 1,2-oxazinan-2-yl. The ring in these embodiments may be optionally substituted as described herein.

"Optional" or "optionally" means that the subsequently described event of circumstances may or may not occur, and that the description includes instances where said event or circumstance occurs one or more times and instances in which it does not. For example, "optionally substituted alkyl" means that the alkyl group may or may not be substituted and that the description includes both substituted alkyl groups and alkyl groups having no substitution, and that said alkyl groups may be substituted one or more times. Examples of optionally substituted alkyl groups include, without limitation, methyl, ethyl, propyl, etc. and including cycloalkyls such as cyclopropyl, cyclobutyl, cyclopentyl, cyclohexyl, cycloheptyl, etc.; examples of optionally substituted alkenyl groups include allyl, crotyl, 2-pentenyl, 3-hexenyl, 2-cyclopentenyl, 2-cyclohexenyl, 2-cyclopentenylmethyl, 2-cyclohexenylmethyl, etc. In some embodiments, optionally substituted alkyl and alkenyl groups include $C_{1-6}$ alkyls or alkenyls.

Therapeutic Indications

The invention provides methods of treating conditions that are modulated, directly or indirectly, by an O-GlcNAcase enzyme or by O-GlcNAc-modified protein levels, for example, a condition that is benefited by inhibition of an O-GlcNAcase enzyme or by an elevation of O-GlcNAc-modified protein levels. Such conditions include, without limitation, Glaucoma, Schizophrenia, tauopathies, such as Alzheimer's disease, neurodegenerative diseases, cardiovascular diseases, diseases associated with inflammation, diseases associated with immunosuppression and cancers. One or more of the compounds of the invention are also useful in the treatment of diseases or disorders related to deficiency or over-expression of O-GlcNAcase or accumulation or depletion of O-GlcNAc, or any disease or disorder responsive to glycosidase inhibition therapy. Such diseases and disorders include, but are not limited to, Glaucoma, Schizophrenia, neurodegenerative disorders, such as Alzheimer's disease (AD), or cancer. Such diseases and disorders may also include diseases or disorders related to the accumulation or deficiency in the enzyme OGT. Also included is a method of protecting or treating target cells expressing proteins that are modified by O-GlcNAc residues, the dysregulation of which modification results in disease or pathology. The term "treating" as used herein includes treatment, prevention, and amelioration.

In alternative embodiments, the invention provides methods of enhancing or elevating levels of protein O-GlcNAc modification in animal subjects, such as, veterinary and human subjects. This elevation of O-GlcNAc levels can be useful for the prevention or treatment of Alzheimer's disease; prevention or treatment of other neurodegenerative diseases (e.g. Parkinson's disease, Huntington's disease); providing neuroprotective effects; preventing damage to cardiac tissue; and treating diseases associated with inflammation or immunosuppression.

In alternative embodiments, the invention provides methods of selectively inhibiting an O-GlcNAcase enzyme in animal subjects, such as veterinary and human subjects.

In alternative embodiments, the invention provides methods of inhibiting phosphorylation of tau polypeptides, or inhibiting formation of NFTs, in animal subjects, such as, veterinary and human subjects. Accordingly, a compound of the invention may be used to study and treat AD and other tauopathies.

In general, the methods of the invention are effected by administering a compound according to the invention to a subject in need thereof, or by contacting a cell or a sample with a compound according to the invention, for example, a pharmaceutical composition comprising a therapeutically effective amount of the compound according to Formula (I). More particularly, they are useful in the treatment of a disorder in which the regulation of O-GlcNAc protein modification is implicated, or any condition as described herein. Disease states of interest include Alzheimer's disease (AD) and related neurodegenerative tauopathies, in which abnormal hyperphosphorylation of the microtubule-associated protein tau is involved in disease pathogenesis. In some embodiments, a compound may be used to block hyperphosphorylation of tau by maintaining elevated levels of O-GlcNAc on tau, thereby providing therapeutic benefit.

The effectiveness of a compound in treating pathology associated with the accumulation of toxic tau species (for example, Alzheimer's disease and other tauopathies) may be confirmed by testing the ability of a compound to block the formation of toxic tau species in established cellular[118-120] and/or transgenic animal models of disease.[32,33]

Tauopathies that may be treated with a compound of the invention include: Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, and Glaucoma.

One or more of the compounds of this invention are also useful in the treatment of conditions associate with tissue damage or stress, stimulating cells, or promoting differentiation of cells. Accordingly, in some embodiments, a compound of this invention may be used to provide therapeutic benefit in a variety of conditions or medical procedures involving stress in cardiac tissue, including but not limited to: ischemia; hemorrhage; hypovolemic shock; myocardial infarction; an interventional cardiology procedure; cardiac bypass surgery; fibrinolytic therapy; angioplasty; and stent placement.

The effectiveness of a compound in treating pathology associated with cellular stress (including ischemia, hemorrhage, hypovolemic shock, myocardial infarction, and other cardiovascular disorders) may be confirmed by testing the ability of a compound to prevent cellular damage in established cellular stress assays,[105,116,117] and to prevent tissue damage and promote functional recovery in animal models of ischemia-reperfusion,[70,114] and trauma-hemorrhage.[72,112,115]

Compounds that selectively inhibit O-GlcNAcase activity may be used for the treatment of diseases that are associated with inflammation, including but not limited to, inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, Guillain-Barr syndrome, systemic lupus erythematosus, myasthenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition, compounds that affects levels of protein O-GlcNAc modification may be used for the treatment of diseases associated with immunosuppression, such as in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes.

One or more of the compounds of the invention may be useful for treatment of neurodegenerative diseases, including Parkinson's disease and Huntington's disease. Other conditions that may be treated are those triggered, affected, or in any other way correlated with levels of O-GlcNAc post-translational protein modification. It is expected that one or more of the compounds of this invention may be useful for the treatment of such conditions and in particular, but not limited to, the following for which a association with O-GlcNAc levels on proteins has been established: graft rejection, in particular but not limited to solid organ transplants, such as heart, lung, liver, kidney, and pancreas transplants (e.g. kidney and lung allografts); cancer, in particular but not limited to cancer of the breast, lung, prostate, pancreas, colon, rectum, bladder, kidney, ovary; as well as non-Hodgkin's lymphoma and melanoma; epilepsy, pain, fibromyalgia, or stroke, e.g., for neuroprotection following a stroke.

Pharmaceutical & Veterinary Compositions, Dosages, And Administration

Pharmaceutical compositions including compounds according to the invention, or for use according to the invention, are contemplated as being within the scope of the invention. In some embodiments, pharmaceutical compositions including an effective amount of a compound of Formula (I) are provided.

The compounds of Formula (I) and their pharmaceutically acceptable salts, enantiomers, solvates, and derivatives are useful because they have pharmacological activity in animals, including humans. In some embodiments, one or more of the compounds according to the invention are stable in plasma, when administered to a subject.

In some embodiments, a compound according to the invention, or for use according to the invention, may be provided in combination with any other active agents or pharmaceutical compositions where such combined therapy is useful to modulate O-GlcNAcase activity, for example, to treat neurodegenerative, inflammatory, cardiovascular, or immunoregulatory diseases, or any condition described herein. In some embodiments, a compound according to the invention, or for use according to the invention, may be provided in combination with one or more agents useful in the prevention or treatment of Alzheimer's disease. Examples of such agents include, without limitation, acetylcholine esterase inhibitors (AChEIs) such as Aricept® (Donepezil), Exelon®(Rivastigmine), Razadyne® (Razadyne ER®, Reminyl®, Nivalin®, Galantamine), Cognex® (Tacrine), Dimebon, Huperzine A, Phenserine, Debio-9902 SR (ZT-1 SR), Zanapezil (TAK0147), ganstigmine, NP7557, etc.;
  NMDA receptor antagonists such as Namenda® (Axura®, Akatinol®, Ebixa®, Memantine), Dimebon, SGS-742, Neramexane, Debio-9902 SR (ZT-1 SR), etc.;
  gamma-secretase inhibitors and/or modulators such as Flurizan™ (Tarenflurbil, MPC-7869, R-flurbiprofen), LY450139, MK 0752, E2101, BMS-289948, BMS-299897, BMS-433796, LY-411575, GSI-136, etc.;
  beta-secretase inhibitors such as ATG-Z1, CTS-21166, etc.;
  alpha-secretase activators, such as NGX267, etc;
  amyloid-β aggregation and/or fibrillization inhibitors such as Alzhemed™ (3APS, Tramiprosate, 3-amino-1-propanesulfonic acid), AL-108, AL-208, AZD-103, PBT2, Cereact, ONO-2506PO, PPI-558, etc.;
  tau aggregation inhibitors such as methylene blue, etc.;
  microtubule stabilizers such as AL-108, AL-208, paclitaxel, etc.;
  RAGE inhibitors, such as TTP488, etc.;
  5-HT1a receptor antagonists, such as Xaliproden, Lecozotan, etc.;
  5-HT4 receptor antagonists, such as PRX-03410, etc.;
  kinase inhibitors such as SRN-003-556, amfurindamide, LiCl, AZD1080, NP031112, SAR-502250, etc.;
  humanized monoclonal anti-Aβ antibodies such as Bapineuzumab (AAB-001), LY2062430, RN1219, ACU-5A5, etc.;
  amyloid vaccines such as AN-1792, ACC-001, etc.;
  neuroprotective agents such as Cerebrolysin, AL-108, AL-208, Huperzine A, etc.;
  L-type calcium channel antagonists such as MEM-1003, etc.;
  nicotinic receptor antagonists, such as AZD3480, GTS-21, etc.;

nicotinic receptor agonists, such as MEM 3454, Nefiracetam, etc.;

peroxisome proliferator-activated receptor (PPAR) gamma agonists such as Avandia® (Rosglitazone), etc.;

phosphodiesterase IV (PDE4) inhibitors, such as MK-0952, etc.;

hormone replacement therapy such as estrogen (Premarin), etc.;

monoamine oxidase (MAO) inhibitors such as NS2330, Rasagiline (Azilect®), TVP-1012, etc.;

AMPA receptor modulators such as Ampalex (CX 516), etc.;

nerve growth factors or NGF potentiators, such as CERE-110 (AAV-NGF), T-588, T-817MA, etc.;

agents that prevent the release of luteinizing hormone (LH) by the pituitary gland, such as leuoprolide (VP-4896), etc.;

GABA receptor modulators such as AC-3933, NGD 97-1, CP-457920, etc.;

benzodiazepine receptor inverse agonists such as SB-737552 (S-8510), AC-3933, etc.;

noradrenaline-releasing agents such as T-588, T-817MA, etc.

It is to be understood that combination of compounds according to the invention, or for use according to the invention, with Alzheimer's agents is not limited to the examples described herein, but includes combination with any agent useful for the treatment of Alzheimer's disease. Combination of compounds according to the invention, or for use according to the invention, and other Alzheimer's agents may be administered separately or in conjunction. The administration of one agent may be prior to, concurrent to, or subsequent to the administration of other agent(s).

In alternative embodiments, a compound may be supplied as a "prodrug" or protected forms, which release the compound after administration to a subject. For example, a compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention where a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in one or more of the compounds of the invention and the like.

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987, all of which are incorporated in full by reference herein.

Suitable prodrug forms of one or more of the compounds of the invention include embodiments in which one or more $R^3$ as set forth in Formula (I) is (CO)R, where R is optionally substituted alkyl, alkenyl, alkynyl, aryl, or heteroaryl. In these cases the ester groups may be hydrolyzed in vivo (e.g. in bodily fluids), releasing the active compounds in which each $R^3$ is H. Preferred prodrug embodiments of the invention include compounds of Formula (I) where one or more $R^3$ is $C(O)CH_3$.

Compounds according to the invention, or for use according to the invention, can be provided alone or in combination with other compounds in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

A compound of the present invention may be administered in the form of a pharmaceutically acceptable salt. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising compounds of Formula I used in the form of a salt thereof, particularly where the salt form confers on the active ingredient improved pharmacokinetic properties as compared to the free form of the active ingredient or other previously disclosed salt form.

A "pharmaceutically acceptable salt" includes both acid and base addition salts. A "pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of a compound of the present invention can be used as a dosage for modifying solubility or hydrolysis characteristics, or can be used in sustained release or prodrug formulations. Also, pharmaceutically acceptable salts of a compound of this invention may include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations will typically include one or more carriers acceptable for the mode of administration of the preparation, be it by injection, inhalation, topical administration, lavage, or other modes suitable for the selected treatment. Suitable carriers are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy* by Alfonso Gennaro, $20^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of a compound. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

A compound or a pharmaceutical composition according to the present invention may be administered by oral or non-oral, e.g., intramuscular, intraperitoneal, intravenous, intracisternal injection or infusion, subcutaneous injection, transdermal or transmucosal routes. In some embodiments, a compound or pharmaceutical composition in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. A compound may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaryies. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

A compound of the invention may be used to treat animals, including mice, rats, horses, cattle, sheep, dogs, cats, and monkeys. However, a compound of the invention can also be used in other organisms, such as avian species (e.g., chickens). One or more of the compounds of the invention may also be effective for use in humans. The term "subject" or alternatively referred to herein as "patient" is intended to be referred to an animal, preferably a mammal, most preferably a human, who has been the object of treatment, observation or experiment. However, one or more of the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition requiring modulation of O-GlcNAcase activity.

An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as inhibition of an O-GlcNAcase, elevation of O-GlcNAc levels, inhibition of tau phosphorylation, or any condition described herein. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as inhibition of an O-GlcNAcase, elevation of O-GlcNAc levels, inhibition of tau phosphorylation, or any condition described herein. Typically, a prophylactic dose is used in subjects prior to or at an earlier stage of disease, so that a prophylactically effective amount may be less than a therapeutically effective amount. A suitable range for therapeutically or prophylactically effective amounts of a compound may be any integer from 0.1 nM-0.1 M, 0.1 nM-0.05 M, 0.05 nM-15 µM or 0.01 nM-10 µM.

In alternative embodiments, in the treatment or prevention of conditions which require modulation of O-GlcNAcase activity, an appropriate dosage level will generally be about 0.01 to 500 mg per kg subject body weight per day, and can be administered in singe or multiple doses. In some embodiments, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, one or more of the compounds exhibit a suitable safety profile for therapeutic use. Toxicity of a compound of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H), deuterium ($^2$H) and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the Schemes and Examples herein using appropriate isotopically-enriched reagents and/or intermediates.

Other Uses and Assays

A compound of Formula (I) may be used in screening assays for compounds which modulate the activity of glycosidase enzymes, preferably the O-GlcNAcase enzyme. The ability of a test compound to inhibit O-GlcNAcase-dependent cleavage of O-GlcNAc from a model substrate may be measured using any assays, as described herein or known to one of ordinary skill in the art. For example, a fluoresence or UV-based assay known in the art may be used. A "test compound" is any naturally-occurring or artificially-derived chemical compound. Test compounds may include, without limitation, peptides, polypeptides, synthesised organic molecules, naturally occurring organic molecules, and nucleic acid molecules. A test compound can "compete" with a known compound such as a compound of Formula (I) by, for example, interfering with inhibition of O-GlcNAcase-dependent cleavage of O-GlcNAc or by interfering with any biological response induced by a compound of Formula (I).

Generally, a test compound can exhibit any value between 10% and 200%, or over 500%, modulation when compared to a compound of Formula (I) or other reference compound. For example, a test compound may exhibit at least any positive or negative integer from 10% to 200% modulation, or at least any positive or negative integer from 30% to 150% modulation, or at least any positive or negative integer from 60% to 100% modulation, or any positive or negative integer over 100% modulation. A compound that is a negative modulator will in general decrease modulation relative to a known compound, while a compound that is a positive modulator will in general increase modulation relative to a known compound.

In general, test compounds are identified from large libraries of both natural products or synthetic (or semi-synthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, Mass., USA. In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

When a crude extract is found to modulate inhibition of O-GlcNAcase-dependent cleavage of O-GlcNAc, or any biological response induced by a compound of Formula (I), further fractionation of the positive lead extract is necessary to isolate chemical constituents responsible for the observed effect. Thus, the goal of the extraction, fractionation, and purification process is the careful characterization and identification of a chemical entity within the crude extract having O-GlcNAcase-inhibitory activities. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified according to methods known in the art. Compounds identified as being of therapeutic, prophylactic, diagnostic, or other value may be subsequently analyzed using a suitable animal model, as described herein on known in the art.

In some embodiments, one or more of the compounds are useful in the development of animal models for studying diseases or disorders related to deficiencies in O-GlcNAcase, over-expression of O-GlcNAcase, accumulation of O-GlcNAc, depletion of O-GlcNAc, and for studying treatment of diseases and disorders related to deficiency or over-expression of O-GlcNAcase, or accumulation or depletion of O-GlcNAc. Such diseases and disorders include neurodegenerative diseases, including Alzheimer's disease, and cancer.

Various alternative embodiments and examples of the invention are described herein. These embodiments and examples are illustrative and should not be construed as limiting the scope of the invention.

EXAMPLES

The following examples are intended to illustrate embodiments of the invention and are not intended to be construed in a limiting manner.
Abbreviations
ABCN=1,1'-azobis(cyclohexane-carbonitrile)
AcCl=acetyl chloride
AcOH=acetic acid
BCl$_3$=boron trichloride
BnBr=benzyl bromide
Boc$_2$O=di-tert-butyl dicarbonate
BzCl=benzoyl chloride
DAST=diethylaminosulfur trifluoride
DCM=dichloromethane
DIPEA=diisopropylethylamine
DMAP=4-dimethylaminopyridine
DMF=N,N-dimethylformamide
DMP=Dess-Martin periodinane
Et$_3$N=triethylamine
Et$_2$O=diethyl ether
TBDMSCl=tert-butyldimethylsilyl chloride
TBAF=tetra-n-butylammonium fluoride
TFA=2,2,2-trifluoroacetic acid
THF=tetrahydrofuran
thio-CDI=1,1'-thiocarbonyl diimidazole Example 1

(3aR,5R,6S,7R,7aR)-2-(ethylamino)-5-methyl-5,6,7,7a-tetrahydro-3aH-pyrano[3,2-d]thiazole-6,7-diol

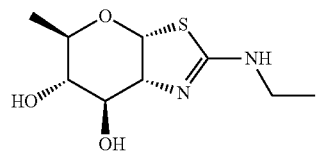

To a suspension of -(3aR,5R,6S,7R,7aR)-2-(ethylamino)-5-(hydroxymethyl)-5,6,7,7a-tetrahydro-3aH-pyrano[3,2-d]thiazole-6,7-diol (35.0 g, 141 mmol) in DMF (300 mL) cooled at 15° C., was added DIPEA (6.0 mL), Boc$_2$O (61.5 g, 282 mmol) and MeOH (6.0 mL). The mixture was stirred at room temperature for 16 h, and then MeOH (50 mL) was added. The reaction mixture was concentrated under reduced pressure at ~35° C. The residue was purified on silica gel by flash column chromatography (EtOAc/hexanes 1:1, then MeOH/DCM, 1:5), followed by recrystallization from EtOAc/hexanes, to afford tert-butyl (-(3aR,5R,6S,7R,7aR)-6,7-dihydroxy-5-(hydroxymethyl)-5,6,7,7a-tetrahydro-3aH-pyrano[3,2-d]thiazol-2-yl)(ethyl)carbamate as a white solid (31.5 g, 64% yield). $^1$H NMR (400 MHz, CDCl$_3$) δ 6.12 (d, J=6.8 Hz, 1H), 4.23-4.22 (m, 1H), 4.17-4.14 (m, 1H), 3.91-3.86 (m, 2H), 3.81-3.77 (m, 3H), 3.59-3.55 (m, 1H), 3.17-3.16 (m, 1H, OH), 1.53 (s, 9H), 1.16 (t, J=7.0 Hz, 3H).

To a solution of the above material (5.0 g, 14.4 mmol) in DMF (25 mL) was added imidazole (1.57 g, 23.1 mmol) and TBDMSCl (2.82 g, 18.7 mmol). The reaction mixture stirred at room temperature for 30 h was diluted with EtOAc (100 mL). Organics were washed with satd. NH$_4$Cl, brine, dried over anhydrous Na$_2$SO$_4$ and concentrated. The residue was purified on silica gel by flash column chromatography (EtOAc/hexanes, 1:1), affording tert-butyl (-(3aR,5R,6S,7R,7aR)-5-(((tert-butyldimethylsilyl)oxy)methyl)-6,7-dihydroxy-5,6,7,7a-tetrahydro-3aH-pyrano[3,2-d]thiazol-2-yl)(ethyl)carbamate as a white solid (5.08 g, 76%). $^1$H NMR (400 MHz, CDCl$_3$) δ 6.12 (d, J=6.7 Hz, 1H), 4.25 (t, J=6.2 Hz, 1H), 4.16 (t, J=6.4 Hz, 1H), 4.10-4.04 (m, 2H), 3.91-3.85 (m, 3H), 3.65-3.62 (m, 1H), 1.55 (s, 9H), 1.26 (t, J=7.0 Hz, 3H), 0.89 (s, 9H), 0.08 (s, 6H).

To a solution of the above material (1.15 g, 2.5 mmol), tetrabutyl ammonium iodide (0.092 g, 0.25 mmol) in DMF (25 mL) at 0° C. was added NaH (60%, 0.3 g, 7.5 mmol) followed by p-methoxybenzyl chloride (1.02 mL, 7.5 mmol). The reaction mixture was then stirred at room temperature for 6 h, diluted with Et₂O (50 mL) and quenched with water (5 mL). The ether layer was further washed with satd. NH₄Cl, brine, dried over anhydrous Na₂SO₄ and concentrated. A mixture of two products, tert-butyl (-(3aR,5R,6S,7R,7aR)-6-((tert-butyldimethylsilyfloxy)-7-((4-methoxybenzypoxy)-5-((4-methoxyphenoxy)methyl)-5,6,7,7a-tetrahydro-3aH-pyrano[3,2-d]thiazol-2-yl)(ethyl)carbamate and tert-butyl (-(3aR,5R,6S,7R,7aR)-5-(((tert-butyldimethylsilypoxy)methyl)-6,7-bis((4-methoxybenzyl)oxy)-5,6,7,7a-tetrahydro-3aH-pyrano[3,2-d]thiazol-2-yl)(ethyllearbamate was isolated (1.6 g, 66%) in a 1:2 ratio, respectively, as indicated by ¹H NMR.

To a solution of the above mixture (1.58 g, 2.26 mmol) in THF (15 mL) was added 1M TBAF solution (4.0 mL, 4 mmol) at 0° C. and the mixture was then stirred at room temperature for 2 h. Diluted with EtOAc (50 mL), the organic layer was washed with satd. NH₄Cl, dried over anhydrous Na₂SO₄ and concentrated. The crude residue was purified on silica gel by flash column chromatography (EtOAc/hexanes, 1:2), affording tert-butyl ethyl(-(3aR,5R,6S,7R,7aR)-5-(hydroxymethyl)-6,7-bis((4-methoxybenzypoxy)-5,6,7,7a-tetrahydro-3aH-pyrano[3,2-d]thiazol-2-yl)carbamate (0.75 g, 56%) as a gummy solid. ¹H NMR (400 MHz, CDCl₃): δ 7.30 (d, J=8.6, 2H), 7.15 (d, J=8.6, 2H), 6.88-6.80 (m, 4H), 6.01 (d, J=6.9 Hz, 1H), 4.64 (d, J=11.8 Hz, 1H), 4.59 (d, J=11.8 Hz, 1H), 4.48-4.45 (m, 1H), 4.37-4.34 (ddd, J=6.8, 3.6, 1.28 Hz, 1H), 4.27 (d, J=11.2 Hz, 1H), 4.24-4.23 (dd, J=1.8, 1.76 Hz, 1H), 3.87-3.80 (m, 2H), 3.78 (s, 3H), 3.77 (s, 3H), 3.70-3.65 (m, 1H), 3.59-3.56 (dt, J=9.0, 1.44 Hz, 1H), 3.55-3.49 (m, 1H), 3.41-3.37 (ddd, J=8.5, 5.3, 2.8 Hz, 1H), 1.78 (t, J=6.4 Hz, 1H), 1.50 (s, 9H), 1.18 (t, J=6.9 Hz, 3H).

To a solution of triphenyl phosphine (0.179 g, 0.68 mmol) in dry toluene (5 mL) was added iodine (0.145 g, 0.57 mmol), pyridine (0.1 mL, 1.2 mmol) and a solution of the above material (0.210 g, 0.357 mmol) pre-dissolved in toluene (3 mL). The reaction mixture was stirred at 65° C. for 3.5 h. Insoluble yellowish material was filtered off and filtrate diluted with EtOAc (50 mL) was washed with 1N HCl (20 mL), satd. NaHCO₃ (20 mL) and brine. EtOAc layer was separated, dried over Na₂SO₄ and concentrated to crude product which was purified on silica gel by flash column chromatography (EtOAc/hexanes, 3:7), affording tert-butyl ethyl(-(3aR,5S,6S,7R,7aR)-5-(iodomethyl)-6,7-bis((4-methoxybenzyl)oxy)-5,6,7,7a-tetrahydro-3aH-pyrano[3,2-d]thiazol-2-yl)carbamate as a white solid (0.23 g, 92.4%). ¹H NMR (400 MHz, CDCl₃) δ 7.33 (d, J=8.4, 2H), 7.18 (d, J=8.4, 2H), 6.89-6.82 (m, 4H), 6.07 (d, J=7 Hz, 1H), 4.67 (d, J=11.6 Hz, 1H), 4.61 (d, J=11.6 Hz, 1H), 4.54-4.51 (m, 1H), 4.36-4.31 (m, 2H), 4.19 (t, J=2.64 Hz, 1H), 3.87 (d, J=6.9 Hz, 1H), 3.83 (d, J=6.9 Hz, 1H), 3.77 (s, 6H), 3.50-3.48 (dd, J=6.8, 1.3 Hz, 1H), 3.37-3.34 (m, 1H), 3.23-3.20 (m, 2H), 1.51 (s, 9H), 1.10 (t, J=6.9 Hz, 3H).

To a solution of the above material (0.120 g, 0.172 mmol) in ethanol (4 mL) and Et₃N (0.1 mL) was added Pd/C (10% Wt, 0.060 g). The mixture was hydrogenated at 50 psi and at room temperature for 24 h. Catalyst was removed by filtration and solvents were evaporated under reduced pressure. The residue was purified by silica gel column chromatography, eluted with 3:7 EtOAc/hexanes to give tert-butyl (-(3aR,5R, 6R,7R,7aR)-6,7-bis((4-methoxybenzypoxy)-5-methyl-5,6, 7,7a-tetrahydro-3aH-pyrano[3,2-d]thiazol-2-yl)(ethyl)carbamate (0.077 g, 78.4%) as a white solid. ¹H NMR (400 MHz, CDCl₃) δ 7.31 (d, J=6.8, 2H), 7.17 (d, J=6.8, 2H), 6.87-6.81 (m, 4H), 6.07 (d, J=5.6 Hz, 1H), 4.67 (d, J=9.4 Hz, 1H), 4.58 (d, J=9.4 Hz, 1H), 4.50 (d, J=8.9 Hz, 1H), 4.34 (m, 1H), 4.27 (d, J=8.9 Hz, 1H), 4.23-4.17 (m, 1H), 3.87-3.84 (m, 2H), 3.78 (s, 3H), 3.77 (s, 3H), 3.44-3.39 (m, 1H), 3.30-3.28 (m, 1H), 1.50 (s, 9H), 1.18 (d, J=4.9 Hz, 3H), 1.10 (t, J=5.5 Hz, 3H).

The above material (0.075 g, 0.131 mmol) was dissolved in 30% TFA/DCM solution (10 mL) and stirred at room temperature for 2.5 h. The reaction mixture was concentrated and co-evaporated with Et₂O (20 mL). To the residue was added 2M NH₃/MeOH solution (3 mL) and concentrated under reduced pressure. The product obtained was purified on silica gel by flash column chromatography eluted with 5% MeOH in DCM and 94:4:2 DCM-MeOH—NH₄OH (28% aqueous) to give -(3aR,5R,6S,7R,7aR)-2-(ethylamino)-5-methyl-5,6, 7,7a-tetrahydro-3aH-pyrano[3,2-d]thiazole-6,7-diol as a white solid (0.021 g, 68.7%). ¹H NMR (400 MHz, CD₃OD) δ 6.60 (d, J=6.5 Hz, 1H), 4.08 (t, J=7.04 Hz, 1H), 3.77 (t. J=7.2 Hz, 1H), 3.75-3.72 (m, 1H), 3.44-3.38 (ddd, J=14.6, 7.28, 2.08 Hz, 2H), 3.25-3.20 (dd, J=7.7, 1.12 Hz, 1H), 1.33 (d, J=6.2 Hz, 3H), 1.28 (t, J=7.2 Hz, 3H); ¹³C NMR (100 MHz, CD₃OD) δ 160. 40, 90.08, 75.69, 75.66, 74.21, 66.27, 55.65, 18.91, 14.51; MS, m/z=233 (M+1).

Example 2

(3aR,5R,6S,7aR)-2-(ethylamino)-5-(hydroxymethyl)-5,6,7,7a-tetrahydro-3aH-pyrano[3,2-d]thiazol-6-ol

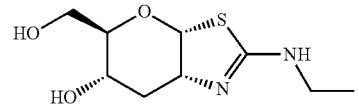

To a solution of tert-butyl ((3 aR,5R,6S,7R,7aR)-6,7-dihydroxy-5-(hydroxymethyl)-5,6,7,7a-tetrahydro-3aH-pyrano [3,2-d]thiazol-2-yl)(ethyl)carbamate (1.64 g, 4.73 mmol), DIPEA (1.34 g, 10.4 mmol) and DMAP (0.010 g, 0.082 mmol) in DCM (50 mL), at 0° C., was added BzCl (1.33 g, 9.50 mmol) slowly. After addition the mixture was stirred at room temperature overnight. Satd. aqueous NH₄Cl solution (50 mL) was added, and the organic layer was collected. The aqueous layer was further extracted with DCM (2×40 mL). The combined extract was dried over anhydrous Na₂SO₄. After filtration the solvent was evaporated under reduced pressure, and the residue was separated on silica gel by flash column chromatography (EtOAc/hexanes, 1:4 to 1:2), affording (-(3aR,5R,6S,7R,7aR)-6-(benzoyloxy)-2-((tert-butoxycarbonyl)(ethyl)amino)-7-hydroxy-5,6,7,7a-tetrahydro-3aH-pyrano[3,2-d]thiazol-5-yl)methyl benzoate as a white solid (0.67 g, 26%). ¹H NMR (400 MHz, CDCl₃) δ 8.08 (d, J=8.1 Hz, 4H), 7.57-7.35 (m, 6H), 6.19 (d, J=7.1 Hz, 1H), 5.21 (dd, J=2.8, 9.2 Hz, 1H), 4.56-4.51 (m, 2H), 4.47-4.42 (m, 2H), 4.14-4.10 (m, 1H), 3.99-3.92 (m, 2H), 1.55 (s, 9H), 1.19 (t, J=7.2 Hz, 3H).

A mixture of the above material (0.346 g, 0.623 mmol) and thio-CDI (90% tech, 0.20 g, 1.0 mmol) in anhydrous toluene (10 mL) was stirred at 95° C. for 4 h. After cooling the solvent was removed under reduced pressure, and the residue was purified on silica gel by flash column chromatography (EtOAc/hexanes, 2:3), affording -(3aR,5R,6S,7R,7aR)-7-((1H-Imidazole-1-carbonothioyl)oxy)-5-((benzoyloxy)methyl)-2-((tert-butoxycarbonyl)(ethyl)amino)-5,6,7,7a-tetrahydro-3aH-pyrano[3,2-d]thiazol-6-yl benzoate as a yellow solid (0.343 g, 83%). ¹H NMR (400 MHz, CDCl₃) δ 8.76 (s, 1H), 8.08-7.94 (m, 4H), 7.70 (s, 1H), 7.57-7.37 (m, 6H), 7.18

(s, 1H), 6.36 (dd, J=1.9, 3.7 Hz, 1H), 6.17 (d, J=7.1 Hz, 1H), 5.54 (td, J=1.2, 9.2 Hz, 1H), 4.70-4.67 (m, 1H), 4.60 (dd, J=3.2, 12.1 Hz, 1H), 4.42 (dd, J=5.1, 12.2 Hz, 1H), 4.11-4.08 (m, 1H), 4.05-3.97 (m, 2H), 1.56 (s, 9H), 1.22 (t, J=7.2 Hz, 3H).

A mixture of the above material (0.343 g, 0.515 mmol), Bu$_3$SnH (0.291 g, 1.00 mmol) and ABCN (8.0 mg, 0.033 mmol) in anhydrous toluene (10 mL) was stirred at 90° C. for 3 h. After cooling the solvent was removed under reduced pressure, and the residue was purified on silica gel by flash column chromatography (EtOAc/hexanes, 1:4), affording (-(3aR,5R,6S,7aR)-6-(benzoyloxy)-2-((tert-butoxycarbonyl)(ethyl)amino)-5,6,7,7a-tetrahydro-3aH-pyrano[3,2-d]thiazol-5-yl)methyl benzoate as a white solid (0.141 g, 51%). $^1$H NMR (400 MHz, CDCl$_3$) δ 8.03-7.94 (m, 4H), 7.57-7.52 (m, 2H), 7.44-7.35 (m, 4H), 6.07 (d, J=7.2 Hz, 1H), 5.44-5.40 (m, 1H), 4.52-4.41 (m, 3H), 4.06-3.96 (m, 3H), 2.70-2.64 (m, 1H), 2.47-2.40 (m, 1H), 1.56 (s, 9H), 1.18 (t, J=7.2 Hz, 3H).

A mixture of the above material (0.140 g, 0.260 mmol) and K$_2$CO$_3$ (0.030 g, 0.22 mmol) in anhydrous MeOH (6 mL) was stirred at room temperature for 3 h. The solvent was removed under reduced pressure, and the residue was purified on silica gel by flash column chromatography (EtOAc), affording a white solid. The solid was dissolved in MeOH (3 mL), into which HCl (g) was bubbled for 30 sec. The solution was then stirred at room temperature for 3 h. The solvent was removed, and the residue was neutralized with 1.0 M NH$_3$ in MeOH and subsequently purified on silica gel by flash column chromatography (1.0 M NH$_3$ in MeOH/DCM, 1:8), affording -(3aR, 5R,6S,7aR)-2-(ethylamino)-5-(hydroxymethyl)-5,6,7,7a-tetrahydro-3aH-pyrano[3,2-d]thiazol-6-ol as an off-white solid (0.044 g, 73%). $^1$H NMR (500 MHz, CD$_3$OD) δ 6.20 (d, J=7.1 Hz, 1H), 4.28-4.25 (m, 1H), 3.75 (dd, J=2.6, 14.4 Hz, 1H), 3.73-3.69 (m, 1H), 3.61 (dd, J=6.4, 14.4 Hz, 1H), 3.54-3.51 (m, 1H), 3.30-3.22 (m, 2H), 2.16-2.11 (m, 1H), 2.06-2.00 (m, 1H), 1.18 (t, J=7.2 Hz, 3H); $^{13}$C NMR (125 MHz, CD$_3$OD) δ 163.24, 91.35, 77.13, 69.15, 65.79, 63.36, 39.60, 34.75, 14.87; MS, m/z 233 (M+1).

Example 3

(3aR,5R,6S,7aR)-5-(hydroxymethyl)-2-(methylamino)-5,6,7,7a-tetrahydro-3aH-pyrano[3,2-d]thiazol-6-ol

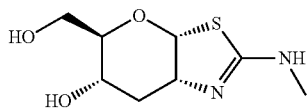

To a suspension of -(3aR,5R,6S,7R,7aR)-5-(hydroxymethyl)-2-(methylamino)-5,6,7,7a-tetrahydro-3aH-pyrano[3, 2-d]thiazole-6,7-diol (1.50 g, 6.40 mmol) and NaHCO$_3$ (1.01 g, 12.0 mmol) in THF/water (40 mL, 1:3) was added benzyl chloroformate (1.70 g, 10.0 mmol). The mixture was stirred at room temperature for 4 days. The organic solvent was removed under reduced pressure to result in a precipitate. The precipitated solid was collected by filtration, washed with Et$_2$O and dried under vacuum, affording benzyl (-(3aR,5R, 6S,7R,7aR)-6,7-dihydroxy-5-(hydroxymethyl)-5,6,7,7a-tetrahydro-3aH-pyrano[3,2-d]thiazol-2-yl)(methyl)carbamate as a white solid (1.72 g, 73%). $^1$H NMR (400 MHz, CD$_3$OD) δ 7.44-7.32 (m, 5H), 6.13 (d, J=6.9 Hz, 1H), 5.27-5.20 (m, 2H), 4.14 (t, J=6.1 Hz, 1H), 4.02 (t, J=4.9 Hz, 1H), 3.74 (dd, J=2.4, 12.0 Hz, 1H), 3.63 (dd, J=6.1, 12.0 Hz, 1H), 3.53 (dd, J=4.5, 9.2 Hz, 1H), 3.47-3.43 (m, 1H), 3.39 (s, 3H).

A mixture of the above material (1.50 g, 4.08 mmol), benzaldehyde dimethyl acetal (3 mL) and p-toluenesulfonic acid monohydrate (0.058 g, 0.30 mmol) in DMF (10 mL) was stirred at 50° C. under a slight vacuum overnight. After cooling the solution was neutralized with solid NaHCO$_3$, and then concentrated under reduced pressure. The residue was purified on silica gel by flash column chromatography (EtOAc/ DCM/hexanes, 2:4:1), affording benzyl (-(3aR,4aR,8aS,9R, 9aR)-9-hydroxy-7-phenyl-3a,4a,5,8a,9,9a-hexahydro-[1,3] dioxino[4',5$^1$:5,6]pyrano[3,2-d]thiazol-2-yl)(methypcarbamate as a white solid (0.91 g, 53%). $^1$H NMR (400 MHz, CDCl$_3$) δ 7.49-7.47 (m, 2H), 7.40-7.35 (m, 8H), 6.28 (d, J=7.5 Hz, 1H), 5.78 (s, 1H), 5.29-5.21 (m, 2H), 4.34 (dd, J=5.1, 10.4 Hz, 1H), 4.15-4.06 (m, 2H), 3.89-3.84 (m, 1H), 3.76 (t, J=10.4 Hz, 1H), 3.58 (t, J=9.4, 1H), 3.38 (s, 3H), 2.62 (d, J=2.4 Hz, 1H).

A mixture of the above material (0.700 g, 1.54 mmol) and thio-CDI (90% tech, 0.80 g, 4.04 mmol) in anhydrous DMF (20 mL) was stirred at 90° C. overnight. After cooling the solvent was removed under reduced pressure, and the residue was purified on silica gel by flash column chromatography (EtOAc/DCM, 2:1), affording 0-(-(3aR,4aR,8aS,9R,9aR)-2-(((benzyloxy)carbonyl)(methyl)amino)-7-phenyl-3a,4a,5, 8a,9,9a-hexahydro-[1,3]dioxino[4',5':5,6]pyrano[3,2-d]thiazol-9-yl) 1H-imidazole-1-carbothioate as a yellow solid (0.71 g, 81%). $^1$H NMR (400 MHz, CDCl$_3$) δ 8.36 (s, 1H), 7.66 (s, 1H), 7.42-7.37 (m, 7H), 7.35-7.32 (m, 3H), 7.03 (s, 1H), 6.28 (d, J=7.2 Hz, 1H), 6.20 (dd, J=7.1, 8.6 Hz, 1H), 5.56 (s, 1H), 5.26 (s, 2H), 4.43 (t, J=7.1 Hz, 1H), 4.39 (dd, J=5.1, 10.4 Hz, 1H), 4.19-4.13 (m, 1H), 3.93 (t, J=9.0 Hz, 1H), 3.79 (t, J=10.4 Hz, 1H), 3.32 (s, 3H).

A mixture of the above material (0.560 g, 1.00 mmol), Bu$_3$SnH (0.87 g, 3.0 mmol) and ABCN (24 mg, 0.10 mmol) in anhydrous THF (20 mL) was stirred at reflux for 3 h. After cooling the solvent was removed under reduced pressure, and the residue was purified on silica gel by flash column chromatography (EtOAc/hexanes/DCM, 1:3:1), affording benzyl methyl(-(3aR,4aR,8aS,9aR)-7-phenyl-3a,4a,5,8a,9,9a-hexahydro-[1,3]dioxino[4',':5,6]pyrano[3,2-d]thiazol-2-yl) carbamate as a white solid (0.32 g, 73%). $^1$H NMR (400 MHz, CDCl$_3$) δ 7.49-7.47 (m, 2H), 7.39-7.33 (m, 8H), 6.21 (d, J=6.5 Hz, 1H), 5.56 (s, 1H), 5.29-5.20 (m, 2H), 4.52-4.25 (m, 2H), 4.08-4.02 (m, 1H), 3.72 (t, J=10.3 Hz, 1H), 3.61-3.54 (m, 1H), 3.33 (s, 3H), 2.41-2.35 (m, 1H), 1.76-1.68 (m, 1H).

To a solution of the above material (0.20 g, 0.45 mmol) in anhydrous DCM (10 mL), cooled at −78° C. under N$_2$, was added boron trichloride in DCM (1.0 M, 2.0 mL, 2.0 mmol). The mixture was stirred for 3 h while the reaction temperature was gradually brought to ~0° C. The mixture was then cooled at −78° C. again, and MeOH (5 mL) was added carefully. After stirred at room temperature for 30 min the mixture was concentrated under reduced pressure. The residue was neutralized with 1.0 M NH$_3$ in MeOH, and subsequently purified on silica gel by flash column chromatography (1.0 M NH$_3$ in MeOH:DCM, 1:7), affording -(3aR,5R,6S,7aR)-5-(hydroxymethyl)-2-(methylamino)-5,6,7,7a-tetrahydro-3aH-pyrano[3,2-d]thiazol-6-ol as an off-white solid (0.070 g, 72%). $^1$H NMR (400 MHz, CD$_3$OD) δ 6.20 (d, J=6.4 Hz, 1H), 4.27-4.23 (m, 1H), 3.74 (dd, J=2.5, 12.0 Hz, 1H), 3.71-3.67 (m, 1H), 3.63 (dd, J=6.2, 12.0 Hz, 1H), 3.54-3.49 (m, 1H), 2.83 (s, 3H), 2.16-2.10 (m, 1H), 2.04-1.97 (m, 1H); $^{13}$C NMR (100 MHz, CD$_3$OD) δ 163.99, 91.81, 77.11, 69.31, 65.82, 63.32, 34.93, 30.49; MS, m/z=219 (M+1).

Example 4

(3aR,5R,6S,7aR)-5-(hydroxymethyl)-2-(dimethylamino)-5,6,7,7a-tetrahydro-3aH-pyrano[3,2-d]thiazol-6-ol

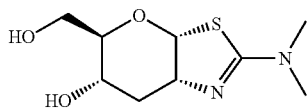

A suspension of -(3aR,5R,6S,7R,7aR)-2-(dimethylamino)-5-(hydroxymethyl)-5,6,7,7a-tetrahydro-3aH-pyrano[3,2-d]thiazole-6,7-diol (0.800 g, 3.23 mmol) and anhydrous ZnCl$_2$ (1.00 g, 7.35 mmol) in benzaldehyde (5 mL) was stirred at room temperature overnight. DCM (50 mL) and satd. aqueous NaHCO$_3$ (50 mL) was added, and mixture was stirred for 20 min. The solid was filtered off, and the organic layer was collected from the filtrate. The aqueous layer was extracted with DCM (2×50 mL), and the combined extract was dried over anhydrous Na$_2$SO$_4$. After filtration the solvent was evaporated under reduced pressure, and the residue was purified on silica gel by flash column chromatography (1.0 M NH$_3$ in MeOH/DCM, 3:100), affording -(3aR,4aR,8aS,9R,9aR)-2-(dimethylamino)-7-phenyl-3a,4a,5,8a,9,9a-hexahydro-[1,3]dioxino[4',5':5,6]pyrano[3,2-d]thiazol-9-ol as a pale yellow solid (0.76 g, 70%). $^1$H NMR (400 MHz, CDCl$_3$) δ 7.51-7.48 (m, 2H), 7.40-7.34 (m, 3H), 6.39 (d, J=6.6 Hz, 1H), 5.58 (s, 1H), 4.31 (dd, J=5.1, 10.4 Hz, 1H), 4.10-4.03 (m, 2H), 3.86 (dd, J=8.2, 9.5 Hz, 1H), 3.76 (t, J=10.4 Hz, 1H), 3.59 (t, J=9.5 Hz, 1H), 3.00 (s, 6H).

A mixture of the above material (0.67 g, 2.0 mmol) and thio-CDI (90% tech, 1.6 g, 8.0 mmol) in anhydrous DMF (20 mL) was stirred at 95° C. overnight. After cooling the solvent was removed under reduced pressure, and the residue was purified on silica gel by flash column chromatography (MeOH/DCM, 1:100 to 5:100), affording a mixture containing O-(-(3aR,4aR,8aS,9R,9aR)-2-(dimethylamino)-7-phenyl-3a,4a,5,8a,9,9a-hexahydro-[1,3]dioxino[4',5':5,6]pyrano[3,2-d]thiazol-9-yl) 1H-imidazole-1-carbothioate. This mixture was dissolved in anhydrous THF (30 mL), and Bu$_3$SnH (1.0 g, 3.4 mmol) and ABCN (0.060 mg, 0.24 mmol) was added, and the mixture was stirred at reflux overnight. The solvent was then removed under reduced pressure, and the residue was purified on silica gel by flash column chromatography (1.0 M NH$_3$ in MeOH:DCM, 3:100), affording an pale yellow solid containing -(3aR,4aR,8aS,9aR)-N,N-dimethyl-7-phenyl-3a,4a,5,8a,9,9a-hexahydro-[1,3]dioxino[4',5':5,6]pyrano[3,2-d]thiazol-2-amine (0.17 g, impure). The solid was treated with 2% HCl in MeOH (10 mL) at room temperature for 2 h, and then the solvent was removed under reduced pressure. The residue was neutralized with 1.0 M NH$_3$ in MeOH, and subsequently purified on silica gel by flash column chromatography (1.0 M NH$_3$ in MeOH:DCM, 1:10), affording pure -(3aR,5R,6S,7aR)-5-(hydroxymethyl)-2-(dimethylamino)-5,6,7,7a-tetrahydro-3aH-pyrano[3,2-d]thiazol-6-ol as an off-white solid (0.050 g, 11% overall yield). $^1$H NMR (400 MHz, CD$_3$OD) δ 6.23 (d, J=6.4 Hz, 1H), 4.28-4.24 (m, 1H), 3.74 (dd, J=2.5, 12.0 Hz, 1H), 3.70-3.65 (m, 1H), 3.59 (dd, J=6.2, 12.0 Hz, 1H), 3.53-3.48 (m, 1H), 2.99 (s, 6H), 2.14-2.08 (m, 1H), 2.02-1.95 (m, 1H); $^{13}$C NMR (100 MHz, CD$_3$OD) δ 165.60, 92.43, 77.19, 69.67, 65.79, 63.27, 40.15, 34.93; MS, m/z=255 (M+23).

The following examples were synthesized according to procedures analogous to the schemes and examples outlined above.

TABLE 2

| Example | Structure | Name |
| --- | --- | --- |
| 5 | 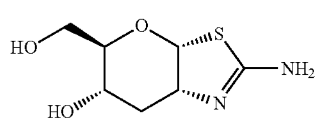 [SMILES: NC1=N[C@@H]2C[C@H](O)[C@@H](CO)O[C@@H]2S1] | (3aR,5R,6S,7aR)-2-amino-5-(hydroxymethyl)-5,6,7,7a-tetrahydro-3aH-pyrano[3,2-d]thiazol-6-ol |

$^1$H NMR (400 MHz, CD$_3$OD) δ 6.44 (d, J = 6.9 Hz, 1H), 4.56-4.52 (m, 1H), 3.90-3.85 (m, 1H), 3.77 (dd, J = 2.5, 12.1 Hz, 1H), 3.63 (dd, J = 6.4, 12.1 Hz, 1H), 3.54-3.50 (m, 1H), 2.18-2.10 (m, 2H); $^{13}$C NMR (100 MHz, CD$_3$OD) δ 172.80, 87.98, 77.53, 63.91, 63.25. 59.96, 32.33; MS, m/z = 205 (M + 1).

| 6 | | (3aR,5R,6S,7aR)-5-(hydroxymethyl)-2-(propylamino)-5,6,7,7a-tetrahydro-3aH-pyrano[3,2-d]thiazol-6-ol |

$^1$H NMR (400 MHz, CD$_3$OD) δ 6.18 (d, J = 6.3 Hz, 1H), 4.26-4.22 (m, 1H), 3.74 (dd, J = 2.1, 11.8 Hz, 1H), 3.71-3.66 (m, 1H), 3.59 (dd, J = 6.3, 11.8 Hz, 1H), 3.54-3.49 (m, 1H), 3.21-3.12 (m, 2H), 2.14-2.08 (m, 1H), 2.04-1.99 (m, 1H), 1.59-1.53 (m, 2H), 0.93 (t, J = 7.3 Hz, 3H); $^{13}$C NMR (100 MHz, CD$_3$OD) δ 163.32, 91.40, 77.17, 69.28, 65.94, 63.36, 46.81, 34.81, 23.67, 11.72; MS, m/z = 269 (M + 23).

Example 7

(3aR,5R,6R,7R,7aR)-2-(ethylamino)-7-fluoro-5-(hydroxymethyl)-5,6,7,7a-tetrahydro-3aH-pyrano[3,2-d]thiazol-6-ol

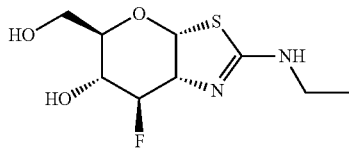 [SMILES: CCNC1=N[C@@H]2[C@@H](F)[C@H](O)[C@@H](CO)O[C@@H]2S1]

To a solution of (-(3aR,5R,6S,7R,7aR)-6-(benzoyloxy)-2-((tert-butoxycarbonyl)(ethyl)amino)-7-hydroxy-5,6,7,7a-tetrahydro-3aH-pyrano[3,2-d]thiazol-5-yl)methyl benzoate (0.49 g, 0.88 mmol) in anhydrous DCM (3 mL), at −40° C. under $N_2$, was added DAST (1.0 g, 6.2 mmol). After addition the mixture was stirred at room temperature overnight. After the reaction mixture was again cooled at −40° C., it was diluted with DCM (20 mL), and then quenched by adding satd. aqueous $NaHCO_3$ dropwise. The organic layer was collected, and the aqueous was extracted with DCM (2×15 mL). The combined extract was dried over anhydrous $Na_2SO_4$. After filtration the solvent was evaporated under reduced pressure, and the residue was purified on silica gel by flash column chromatography (EtOAc/hexanes, 1:5 to 2:7), affording (-(3aR,5R,6R,7R,7aR)-6-(benzoyloxy)-2-((tert-butoxycarbonyl)(ethyl)amino)-7-fluoro-5,6,7,7a-tetrahydro-3aH-pyrano[3,2-d]thiazol-5-yl)methyl benzoate as a white solid (0.14 g, impure, ~28%).

Conversion of the above material to the title compound was accomplished by removal of benzoate and Boc protection groups using $K_2CO_3$ in MeOH and satd. HCl in MeOH respectively, via procedures as described for Example 2. After purification on silica gel by flash column chromatography (1.0 M $NH_3$ in MeOH/DCM, 1:7), -(3aR,5R,6R,7R,7aR)-2-(ethylamino)-7-fluoro-5-(hydroxymethyl)-5,6,7,7a-tetrahydro-3aH-pyrano[3,2-d]thiazol-6-ol was obtained as an off-white solid (0.051 g, 23% overall). $^1$H NMR (400 MHz, $CD_3OD$) δ 6.33 (d, J=6.6 Hz, 1H), 4.77 (td, J=5.0, 48.2 Hz, 1H), 4.34-4.27 (m, 1H), 3.81 (dd, J=2.0, 12.0 Hz, 1H), 3.77-3.72 (m, 1H), 3.68 (dd, J=5.7, 12.0 Hz, 1H), 3.63-3.59 (m, 1H), 3.31-3.23 (m, 2H), 1.18 (t, J=7.2 Hz, 3H); $^{13}$C NMR (100 MHz, $CD_3OD$) δ 163.40, 96.25 (d, J=177.7 Hz), 90.55 (d, J=3.9 Hz), 75.26 (d, J=4.6 Hz), 73.58 (d, J=24.5 Hz), 68.91 (d, J=22.8 Hz), 62.85, 39.54, 14.82; MS, m/z=251 (M+1).

Example 8

(3aR,5R,6R,7R,7aR)-2-(dimethylamino)-7-fluoro-5-(hydroxymethyl)-5,6,7,7a-tetrahydro-3aH-pyrano[3,2-d]thiazol-6-ol

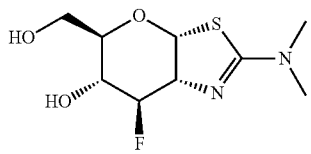

To a solution of -(3aR,5R,6S,7R,7aR)-2-(dimethylamino)-5-(hydroxymethyl)-5,6,7,7a-tetrahydro-3aH-pyrano[3,2-d]thiazole-6,7-diol (5.20 g, 21.0 mmol) and imidazole (12.0 g, 176 mmol) in DMF (60 mL) was added TBDMSCl (15.0 g, 99.5 mmol). The mixture was stirred at room temperature for 24 h, and then diluted with brine (200 mL). The mixture was extracted with $Et_2O$ ((3×100 mL). The combined extract was washed with brine (100 mL) and water (100 mL), and then dried over anhydrous $Na_2SO_4$. After filtration the solvent was evaporated under reduced pressure. The residue was purified on silica gel by flash column chromatography (EtOAc/hexanes, 1:4 to 1:1), affording -(3aR,5R,6R,7R,7aR)-7-((tert-butyldimethylsilyl)oxy)-5-(((tert-butyldimethylsilypoxy)methyl)-2-(dimethylamino)-5,6,7,7a-tetrahydro-3aH-pyrano[3,2-d]thiazol-6-ol as a white solid (5.95 g, 60%). $^1$H NMR (500 MHz, $CDCl_3$) δ 6.15 (d, J=5.8 Hz, 1H), 4.34-4.33 (m, 1H), 4.20 (t, J=5.0 Hz, 1H), 3.80-3.72 (m, 2H), 3.48 (s, br., 2H), 3.01 (s, 6H), 0.90 (s, 9H), 0.89 (s, 9H), 0.13 (s, 3H), 0.12 (s, 3H), 0.07 (s, 6H).

To a solution of the above material (5.95 g, 12.5 mmol) and DMAP (0.12 g, 0.98 mmol) in pyridine (50 mL), at 0° C., was added BzCl (3.00 g, 21.3 mmol) slowly. After addition the mixture was stirred at room temperature for 24 h. Satd. aqueous $NaHCO_3$ solution (100 mL) was added, and the mixture extracted with EtOAc (3×100 mL). The combined extract was dried over anhydrous $Na_2SO_4$. After filtration the solvent was evaporated under reduced pressure, and the residue was purified on silica gel by flash column chromatography (EtOAc/hexanes, 1:9 to 1:3), affording -(3aR,5R,6R,7R,7aR)-7-((tert-butyldimethylsilyl)oxy)-5-(((tert-butyldimethylsilypoxy)methyl)-2-(dimethylamino)-5,6,7,7a-tetrahydro-3aH-pyrano[3,2-d]thiazol-6-yl benzoate as a clear oil (6.85 g, 94%). $^1$H NMR (400 MHz, $CDCl_3$) δ 8.05-8.02 (m, 2H), 7.56-7.52 (m, 1H), 7.43-7.39 (m, 2H), 6.26 (d, J=6.4 Hz, 1H), 5.06-5.03 (m, 1H), 4.40 (dd, J=2.2, 3.8 Hz, 1H), 3.81-3.78 (m, 1H), 3.71-3.70 (m, 2H), 3.03 (s, 6H), 0.88 (s, 9H), 0.85 (s, 9H), 0.17 (s, 3H), 0.13 (s, 3H), 0.02 (s, 3H), 0.00 (3H).

To a solution of the above material (9.30 g, 16.8 mmol) in dry MeOH (100 mL), was bubbled HCl for 2 min, and the mixture was then stirred at room temperature for 2 h. After concentrated under reduced pressure the mixture was treated with satd. aqueous $NaHCO_3$ solution (150 mL), and then extracted with EtOAc (6×80 mL). The combined extract was dried over anhydrous $Na_2SO_4$. After filtration the solvent was evaporated under reduced pressure, affording -(3aR,5R,6S,7R,7aR)-2-(dimethylamino)-7-hydroxy-5-(hydroxymethyl)-5,6,7,7a-tetrahydro-3aH-pyrano[3,2-d]thiazol-6-yl benzoate as a white crystalline solid (5.40 g, 96%). $^1$H NMR (400 MHz, $CDCl_3$) δ 8.03-8.01 (m, 2H), 7.58-7.53 (m, 1H), 7.44-7.39 (m, 2H), 6.37 (d, J=4.5 Hz, 1H), 5.12-5.09 (m, 1H), 4.41-4.37 (m, 2H), 3.94-3.85 (m, 1H), 3.78-3.74 (m, 1H), 3.67 (dd, J=4.9, 12.5 Hz, 1H), 3.00 (s, 6H).

To a solution of the above material (5.35 g, 15.2 mmol) and DMAP (0.050 g, 0.41 mmol) in pyridine (50 mL), at 0° C., was added BzCl (2.22 g, 15.8 mmol) slowly. After addition the mixture was stirred at room temperature for 4 h. Satd. aqueous $NaHCO_3$ solution (100 mL) was added, and the mixture was extracted with EtOAc (2×50 mL). The combined extract was dried over anhydrous $Na_2SO_4$. After filtration the solvent was evaporated under reduced pressure, and the residue was purified on silica gel by flash column chromatography (EtOAc/hexanes, 1:1 to 10:1), affording (-(3aR,5R,6S,7R,7aR)-6-(benzoyloxy)-2-(dimethylamino)-7-hydroxy-5,6,7,7a-tetrahydro-3aH-pyrano[3,2-d]thiazol-5-yl)methyl benzoate as a white solid (4.45 g, 64%). $^1$H NMR (400 MHz, $CDCl_3$) δ 8.04-8.00 (m, 4H), 7.58-7.51 (m, 2H), 7.44-7.37

(m, 4H), 6.38 (d, J=6.6 Hz, 1H), 5.23-5.20 (m, 1H), 4.55 (dd, J=3.2, 12.0 Hz, 1H) 4.48-4.40 (m, 3H), 4.27-4.22 (m, 1H), 3.00 (s, 6H).

To a solution of the above material (0.410 g, 0.898 mmol) in anhydrous DCM (6 mL), at −78° C. under $N_2$, was added DAST (0.87 g, 5.4 mmol). After addition the mixture was stirred at room temperature for 16 h. The reaction mixture was then cooled at −78° C., diluted with DCM (20 mL), and quenched by adding satd. aqueous $NaHCO_3$ (20 mL). The organic layer was collected, and the aqueous was extracted with DCM (2×30 mL). The combined extract was dried over anhydrous $Na_2SO_4$. After filtration the solvent was evaporated under reduced pressure, and the residue was purified on silica gel by flash column chromatography (EtOAc/hexanes, 1:3 to 1:2), affording (-(3aR,5R,6R,7R,7aR)-6-(benzoyloxy)-2-(dimethylamino)-7-fluoro-5,6,7,7a-tetrahydro-3aH-pyrano[3,2-d]thiazol-5-yl)methyl benzoate) as a white solid (0.380 g, 92%). $^1$H NMR (400 MHz, $CDCl_3$) δ 8.03-8.00 (m, 4H), 7.58-7.55 (m, 1H), 7.54-7.51 (m, 1H), 7.44-7.41 (m, 2H), 7.39-7.36 (m, 2H), 6.35 (d, J=5.4 Hz, 1H), 5.47 (dd, J=7.3, 16.3 Hz, 1H), 5.23 (ddd, J=1.1, 2.8, 35.2 Hz, 1H), 4.70-4.66 (m, 1H), 4.52 (dd, J=2.8, 9.6 Hz, 1H), 4.40 (dd, J=4.7, 9.6 Hz, 1H), 4.14-4.10 (m, 1H), 3.05 (s, 6H).

A mixture of the above material (0.375 g, 0.818 mmol) and $K_2CO_3$ (0.113 g, 0.818 mmol) in anhydrous MeOH (8 mL) was stirred at room temperature for 2 h. The reaction mixture was neutralized with dry ice, and the solvent was then removed under reduced pressure. The residue was purified on silica gel by flash column chromatography (1.0 M $NH_3$ in MeOH/DCM, 1:12), affording -(3aR,5R,6R,7R,7aR)-2-(dimethylamino)-7-fluoro-5-(hydroxymethyl)-5,6,7,7a-tetrahydro-3aH-pyrano[3,2-d]thiazol-6-ol as a white solid (0.190 g, 93%). $^1$H NMR (400 MHz, $CD_3OD$) δ 6.35 (d, J=6.7 Hz, 1H), 4.74 (dt, J=48.1, 5.0 Hz, 1H), 4.31 (dt, J=13.8, 6.0 Hz, 1H), 3.79 (dd, J=2.0, 12.0 Hz, 1H), 3.76-3.69 (m, 1H), 3.66 (dd, J=5.8, 12.0 Hz), 3.61-3.57 (m, 1H), 3.01 (s, 6H); $^{13}$C NMR (100 MHz, $CD_3OD$) δ 166.25, 96.36 (d, J=176.8 Hz), 91.60 (d, J=3.9 Hz), 75.45 (d, J=4.6 Hz), 73.99 (d, J=24.7 Hz), 68.98 (d, J=22.9 Hz), 62.91, 40.33; MS, (ES, m/z) [M+H]$^+$ 251.1.

The following examples were synthesized according to procedures analogous to the schemes and examples outlined above.

TABLE 3

| Example | Structure | Name |
| --- | --- | --- |
| 9 | HO, HO, F, O, S, NH (structure) | (3aR,5R,6R,7R,7aR)-7-fluoro-5-(hydroxymethyl)-2-(methylamino)-5,6,7,7a-tetrahydro-3aH-pyrano[3,2-d]thiazol-6-ol |

$^1$HNMR (400 MHz,$CD_3OD$) δ 6.33 (d, J = 6.5 Hz, 1H), 4.75 (dt, J = 48.2, 5.1 Hz, 1H), 4.29 (dt, J = 13.9, 5.9 Hz, 1H), 3.81-3.64 (m, 3H), 3.62-3.57 (m, 1H), 2.84 (s, 3H); $^{13}$C NMR (100 MHz, $CD_3OD$) δ 164.66, 96.42 (d, J = 177.8 Hz), 91.17 (d, J = 4.0 Hz), 75.37 (d, J = 4.6 Hz), 73.68 (d, J = 24.5 Hz), 69.02 (d, J = 22.8 Hz), 62.92, 30.53. (ES, m/z) [M + H]$^+$: 237.1.

| Example | Structure | Name |
| --- | --- | --- |
| 10 | HO, HO, F, O, S, NH (structure) | (3aR,5R,6R,7R,7aR)-7-fluoro-5-(hydroxymethyl)-2-(propylamino)-5,6,7,7a-tetrahydro-3aH-pyrano[3,2-d]thiazol-6-ol |

$^1$H NMR (400 MHz, $CD_3OD$) δ 6.31 (d, J = 6.4 Hz, 1H), 4.74 (dt, J = 48.2, 4.9 Hz, 1H), 4.31-4.24 (m, 1H), 3.81-3.58 (m, 4H), 324-3.15 (m, 2H), 1.60-1.53 (m, 2H), 0.94 (t, J = 7.4 Hz, 3H); $^{13}$C NMR (100 MHz, $CD_3OD$) δ 163.93, 96.41 (d, J = 177.7 Hz), 90.64 (d, J = 4.0 Hz), 75.38 (d, J = 4.5 Hz), 73.63 (d, J = 24.4 Hz), 69.03 (d, J = 22.8 Hz), 62.96, 46.72, 23.66, 11.53, (ES, m/z) [M + H]$^+$: 265.2.

Example 11

(3aR,5R,6R,7S,7aR)-7-fluoro-5-(hydroxymethyl)-2-(methylamino)-5,6,7,7a-tetrahydro-3aH-pyrano[3,2-d]thiazol-6-ol

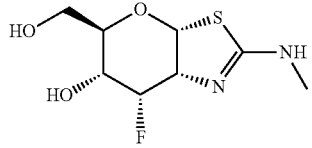

To a solution of tert-butyl (-(3aR,5R,6R,7S,7aR)-5-(((tert-butyldimethylsilyl)oxy)methyl)-7-fluoro-6-hydroxy-5,6,7,7a-tetrahydro-3aH-pyrano[3,2-d]thiazol-2-yl)(methyl)carbamate (0.200 g, 0.444 mmol) in dry MeOH (6 mL) was bubbled HCl gas for 30 sec. The mixture was stirred at room temperature for 5 h. After the solvent was evaporated under reduced pressure, the residue was neutralized with 1.0 M $NH_3$ in MeOH and purified on silica gel by flash column chromatography (1.0 M $NH_3$ in MeOH/DCM, 1:8) followed by recrystallization from MeOH/$Et_2O$, affording -(3aR,5R,6R,7S,7aR)-7-fluoro-5-(hydroxymethyl)-2-(methylamino)-5,6,7,7a-tetrahydro-3aH-pyrano[3,2-d]thiazol-6-ol as a white solid (0.093 g, 89%). $^1$H NMR (400 MHz, $CD_3OD$) δ 6.62 (d, J=6.5 Hz, 1H), 4.89 (td, J=3.5 Hz, 51.0 Hz, 1H), 4.54 (ddd, J=3.5, 6.5, 20.6, 1H), 3.98-3.94 (m, 1H), 3.90-3.84 (m, 1H), 3.83-3.81 (m, 1H), 3.75 (dd, J=5.4, 12.2 Hz, 1H), 2.99 (s, 3H); $^{13}$C NMR (100 MHz, $CD_3OD$) δ 90.63 (d, J=181.3 Hz), 88.53

(d, J=2.3 Hz), 73.60 (d, J=4.3 Hz), 66.02 (d, J=17.3 Hz), 64.80-64.50 (m), 62.44, 31.38; MS, (ES, m/z) [M+H]⁺ 237.1.

Example 12

(3aR,5S,6S,7R,7aR)-2-(ethylamino)-5-(fluoromethyl)-5,6,7,7a-tetrahydro-3aH-pyrano[3,2-d]thiazole-6,7-diol

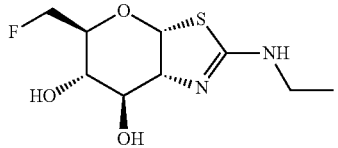 [SMILES: CCNC1=N[C@@H]2[C@@H](O)[C@H](O)[C@@H](CF)O[C@@H]2S1]

Methanesulfonyl chloride (0.038 mL, 0.495 mmol) was added in portions to a stirred solution of tert-butyl ethyl(-(3aR,5R,6S,7R,7aR)-5-(hydroxymethyl)-6,7-bis((4-methoxybenzyl)oxy)-5,6,7,7a-tetrahydro-3aH-pyrano[3,2-d]thiazol-2-yl)carbamate (0.190 g, 0.323 mmol) in dry pyridine (5 mL) at −20° C. After 3 h, the reaction mixture was diluted with DCM (20 mL) and the DCM extract was washed with satd. NaHCO₃, brine, dried over Na₂SO₄ and concentrated. Residual pyridine was removed by co-evaporation with hexanes. The crude product was purified by silica gel column chromatography (3:7 EtOAc/hexanes) to give (-(3aR,5R,6S,7R,7aR)-2-((tert-butoxycarbonyl)(ethyl)amino)-6,7-bis((4-methoxybenzyl)oxy)-5,6,7,7a-tetrahydro-3aH-pyrano[3,2-d]thiazol-5-yl)methyl methanesulfonate (0.215 g, 99.6%) as a white solid. ¹H NMR (400 MHz, CDCl₃) δ 7.32 (d, J=8.5 Hz, 2H), 7.17 (d, J=8.5 Hz, 2H), 6.91-6.83 (m, 4H), 6.01 (d, J=6.88 Hz, 1H), 4.66 (d, J=11.6 Hz, 1H), 4.60 (d, J=11.6 Hz, 1H), 4.52 (d, J=11.1 Hz, 1H), 4.42-4.36 (m, 2H), 4.27-4.23 (m, 3H), 3.96-3.84 (m, 2H), 3.8 (s, 3H), 3.79 (s, 3H), 3.55 (m, 2H), 2.98 (s, 3H), 1.52 (s, 9H), 1.20 (t, J=6.9 Hz, 3H).

To a solution of the above material (0.520 g, 0.78 mmol) in CH₃CN (6 mL) was added a solution of tetraethylammonium fluoride (0.640 g, 4.28 mmol) in CH₃CN (4 mL) and the mixture was heated to reflux for 2.5 h. After evaporation of the solvent, the residue was purified by silica gel column chromatography (1:1 EtOAc/hexanes) to provide tert-butyl ethyl (-(3aR,5S,6S,7R,7aR)-5-(fluoromethyl)-6,7-bis((4-methoxybenzyl)oxy)-5,6,7,7a-tetrahydro-3aH-pyrano[3,2-d]thiazol-2-yl)carbamate (0.335 g, 72.7%) as a foamy solid. 1H NMR (400 MHz, CDCl₃) δ 7.35 (d, J=8.5 Hz, 2H), 7.20 (d, J=8.5 Hz, 2H), 6.93-6.86 (m, 4H), 6.08 (d, J=6.88 Hz, 1H), 4.72 (d, J=11.7 Hz, 1H), 4.65 (d, J=11.7 Hz, 1H), 4.56 (d, J=11.6 Hz, 1H), 4.52-4.51 (m, 1H), 4.41-4.38 (m, 2H), 4.33 (d, J=11.6 Hz, 1H), 4.26 (t, J=2.88 Hz, 1H), 3.93-3.87 (m, 2H), 3.83 (s, 3H), 3.82 (s, 3H), 3.69-3.66 (m, 1H), 3.61-3.50 (m, 1H), 1.55 (s, 9H), 1.15 (t, J=6.9 Hz, 3H).

The above material (0.115 g, 0.195 mmol) dissolved in 30% TFA/DCM at 0° C. was stirred for 3 h at room temperature. TFA/DCM was then evaporated completely and the resulting residue suspended in 2M NH₃/MeOH (3 mL). Methanolic ammonia solution was again concentrated and crude residue was purified by silica gel column chromatography using 10% MeOH in DCM to give -(3aR,5S,6S,7R,7aR)-2-(ethylamino)-5-(fluoromethyl)-5,6,7,7a-tetrahydro-3aH-pyrano[3,2-d]thiazole-6,7-diol as a light yellowish solid (0.035 g, 72.8%). ¹H NMR (400 MHz, CD₃OD) 6.49 (d, J=6.48 Hz, 1H), 4.66-4.52 (dt, J=47.6, 10.5, 4.3 Hz, 2H), 4.12 (t, J=6.6 Hz, 1H), 3.90 (d, J=6.9 Hz, 1H), 3.80-3.73 (m, 2H), 3.55 (dd, J=6.3, 3.2 Hz, 1H), 3.4-3.3 (m, 2H), 1.23 (t, J=7.2 Hz, 3H). ¹³C NMR (100 MHz, MeOD) δ 163.78, 89.63, 83.90 (d, $J_{C6,F}$ 171.7 Hz, C-6), 76.83 (d, $J_{C5,F}$ 17.8 Hz, C-5), 75.43, 69.51 (d, $J_{C4,F}$ 7.0 Hz, C-4), 67.71, 42.13, 14.74. ES/MS: 251.0 [M+1].

Example 13

(3aR,5S,6S,7R,7aR)-2-(dimethylamino)-5-(fluoromethyl)-5,6,7,7a-tetrahydro-3a11-pyrano[3,2-d]thiazole-6,7-diol

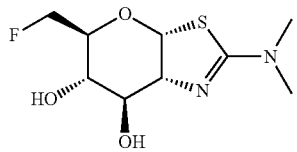 [SMILES: CN(C)C1=N[C@@H]2[C@@H](O)[C@H](O)[C@@H](CF)O[C@@H]2S1]

To a stirred solution of -(3aR,5R,6S,7R,7aR)-5-(((tert-butyldimethylsilyl)oxy)methyl)-2-(dimethylamino)-5,6,7,7a-tetrahydro-3aH-pyrano[3,2-d]thiazole-6,7-diol (1.19 g, 3.3 mmol) in DMF (18 mL) at 0° C. was added NaH (60%, 0.5 g, 13 mmol) in small portions. After 20 min, BnBr (1.17 mL, 9.9 mmol) was added and the reaction mixture was then stirred at room temperature overnight. Reaction was diluted with DCM (100 mL) and DCM extract was washed with satd. NaHCO₃, brine, dried over anhydrous Na₂SO₄ and concentrated. The crude product was purified on silica gel by flash column chromatography (EtOAc/hexanes, 1:1), affording -(3aR,5R,6S,7R,7aR)-6,7-bis(benzyloxy)-5-(((tert-butyldimethylsilyl)oxy)methyl)-N,N-dimethyl-5,6,7,7a-tetrahydro-3aH-pyrano[3,2-d]thiazol-2-amine methanol as a gummy solid (0.805 g, 45%). ¹H NMR (400 MHz, CDCl₃) δ 7.31-7.16 (m, 10H), 6.19 (d, J=6.7 Hz, 1H), 4.72 (d, J=12 Hz, 1H), 4.60 (d, J=12 Hz, 1H), 4.57 (d, J=11.4 Hz, 1H), 4.37-4.32 (m, 2H), 4.06-4.00 (m, 1H), 3.69-3.62 (m, 2H), 3.60-3.52 (m, 2H), 2.89 (s, 6H), 0.80 (s, 9H), 0.04 (s, 6H).

To a solution of the above material (0.80 g, 1.48 mmol) in THF (6 mL) was added 1M TBAF solution (2.25 mL, 2.25 mmol) at 0° C. and the mixture was then stirred at room temperature overnight. Diluted with EtOAc (50 mL), the organic layer was washed with satd. NH₄Cl, dried over anhydrous Na₂SO₄ and concentrated. The crude residue was purified on silica gel by flash column chromatography (100% EtOAc), affording ((3aR,5R,6S,7R,7aR)-6,7-bis(benzyloxy)-2-(dimethylamino)-5,6,7,7a-tetrahydro-3aH-pyrano[3,2-d]thiazol-5-yl)methanol (0.57 g, 90%) as a white solid. ¹H NMR (400 MHz, CDCl₃), δ 7.38-7.28 (m, 10H), 6.29 (d, J=6.9 Hz, 1H), 4.79 (d, J=12.1 Hz, 1H), 4.69 (d, J=12.0 Hz, 1H), 4.65 (d, J=11.7 Hz, 1H), 4.55-4.53 (m, 1H), 4.43 (d, J=11.5 Hz, 1H), 4.24 (m, 1H), 3.77 (d, J=12.1 Hz, 1H), 3.69-3.59 (m, 3H), 3.00 (s, 6H).

Methanesulfonyl chloride (0.180 mL, 2.32 mmol) was added in portions to a stirred solution of the above material (0.673 g, 1.57 mmol) in dry pyridine (8 mL) at −20° C. After 3 h, reaction mixture was diluted with DCM (20 mL) and DCM extract was washed with satd. NaHCO₃ (30 mL), brine, dried over Na₂SO₄ and concentrated. Residual pyridine was removed by co-evaporation with hexanes. The crude product was purified by silica gel column chromatography, eluted with 100% EtOAc to give ((3aR,5R,6S,7R,7aR)-6,7-bis(benzyloxy)-2-(dimethylamino)-5,6,7,7a-tetrahydro-3aH-pyrano[3,2-d]thiazol-5-yl)methyl methanesulfonate (0.610 g, 76.4%) as a white solid. ¹H NMR (400 MHz, CDCl₃) 7.32-7.18 (m, 10H), 6.15 (d, J=6.48 Hz, 1H), 4.68 (d, J=12 Hz, 1H), 4.57 (d, J=12 Hz, 1H), 4.53 (d, J=11.5 Hz, 1H), 4.48-4.45 (dd, J=3.8, 2.0 Hz, 1H), 4.29 (d, J=11.4 Hz, 1H), 4.24-4.16 (m, 3H), 3.73-3.69 (m, 1H), 3.53-3.50 (dt, J=8.9, 1.7 Hz, 1H), 2.91 (s, 6H), 2.90 (s, 3H).

To a solution of the above material (0.7 g, 1.38 mmol) in CH$_3$CN (15 mL) was added a solution of TBAF (1.13 g, 7.59 mmol) in CH$_3$CN (5 mL) and the mixture was heated to reflux for 2.5 h. After evaporation of the solvent, the residue was purified by silica gel column chromatography (7:3 EtOAc/hexanes) to provide -(3aR,5S,6S,7R,7aR)-6,7-bis(benzyloxy)-5-(fluoromethyl)-N,N-dimethyl-5,6,7,7a-tetrahydro-3aH-pyrano[3,2-d]thiazol-2-amine (0.567 g, 95%) as a foamy solid. $^1$H NMR (400 MHz, CDCl$_3$) 7.33-7.18 (m, 10H), 6.20 (d, J=6.5 Hz, 1H), 4.72 (d, J=12 Hz, 1H), 4.60 (d, J=12.6 Hz, 1H), 4.57 (d, J=11.9 Hz, 1H), 4.46-4.41 (m, 2H), 4.34-4.30 (m, 2H), 4.14 (t, J=3 Hz, 1H), 3.74-3.64 (m, 1H), 3.59-3.55 (m, 1H), 2.91 (s, 6H).

To a solution of the above material (0.56 g, 1.3 mmol) in dry DCM (8 mL) at −78° C. was added a solution of BCl$_3$ (1.0 M in DCM, 6.5 mL, 6.5 mmol) dropwise. The mixture was stirred at −78° C. to 0° C. for 3 h. The reaction was then quenched by adding a solution of 1:1 DCM-MeOH (5 mL) at −78° C. The mixture was slowly warmed to room temperature. Solvents were evaporated under reduced pressure. 1.3M NH$_3$/MeOH solution (10 mL) was added to the residue and evaporated. This was repeated for one more time. The residue was purified by silica gel column chromatography, eluted with 90:10 DCM-1.3M NH$_3$-MeOH soln. to give -(3aR,5S,6S,7R,7aR)-2-(dimethylamino)-5-(fluoromethyl)-5,6,7,7a-tetrahydro-3aH-pyrano[3,2-d]thiazole-6,7-diol as a white solid (0.25 g, 76.7%).$^1$H NMR (400 MHz, CD$_3$OD) 6.31 (d, J=6.44 Hz, 1H), 4.63-4.50 (dd, J=44.4, 3.4 Hz, 2H), 4.09 (t, J=6.0 Hz, 1H), 3.92 (t, J=6.9 Hz, 1H), 3.79-3.69 (m, 1H), 3.55-3.51 (dd, J=5.4, 4.04 Hz, 1H), 3.01 (s, 6H).$^{13}$C NMR (100 MHz, MeOD) δ 166.34, 92.58, 84.50 (d, J$_{C6,F}$ 171.2 Hz, C-6), 77.09, 76.56, 76.55, 75.72 (d, J$_{C5,F}$ 17.7 Hz, C-5), 70.73 (d, J$_{C4,F}$ 7.12 Hz, C-4), 40.97. ES/MS: 251.6 [M+1].

Example 14

(3aR,5S,6S,7R,7aR)-2-(allylamino)-5-(fluoromethyl)-5,6,7,7a-tetrahydro-3aH-pyrano[3,2-d]thiazole-6,7-diol

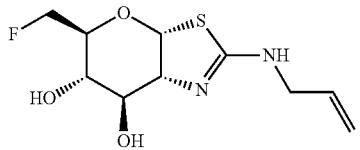 [SMILES: C=CCNC1=N[C@@H]2[C@@H](O)[C@H](O)[C@@H](CF)O[C@@H]2S1]

A solution of -(3aR,5R,6S,7R,7aR)-2-(allyl(tert-butoxycarbonyl)amino)-5-(hydroxymethyl)-5,6,7,7a-tetrahydro-3aH-pyrano[3,2-d]thiazole-6,7-diyldibenzoate (1.7 g, 3.0 mmol) in DCM (40 mL) was treated with DAST (2.5 g, 15.4 mmol) for 30 min at −78° C. After stirred overnight at room temperature, the reaction was quenched with satd. aqueous NaHCO$_3$ (30 mL). The organic layer was separated and the aqueous layer was extracted with DCM (3×20 mL). The combined organic layer was washed with brine (20 mL), dried over anhydrous Na$_2$SO$_4$ and concentrated under vacuum. The residue was purified by a silica gel column with 5%-10% EtOAc in petroleum ether to give -(3aR,5S,6S,7R,7aR)-2-(allyl(tert-butoxycarbonyl)amino)-5-(fluoromethyl)-5,6,7,7a-tetrahydro-3aH-pyrano[3,2-d]thiazole-6,7-diyldibenzoate as a white solid (580 mg, 32%). (ES, m/z): [M+H]$^+$ 571.0; $^1$H NMR (300 MHz, CDCl$_3$) δ 8.09 (d, J=7.5 Hz, 4H), 7.60 (t, J=7.8 Hz, 2H), 7.45 (t, J=7.8 Hz, 4H), 6.27 (d, J=6.3 Hz, 1H), 6.08 (s, 1H), 5.86-5.92 (m, 1H), 5.40 (d, J=9.6 Hz, 1H), 5.12 (d, J=9.3 Hz, 2H), 4.81-4.89 (dd, J=10.0, 2.8 Hz, 1H), 4.63-4.69 (m, 2H), 4.50-4.54 (m, 2H), 3.82-3.98 (m, 1H), 1.63 (s, 9H).

A solution of the above material (540 mg, 0.94 mmol) in MeOH (10 mL) was treated with K$_2$CO$_3$ (26 mg, 0.18 mmol) for 2 h at room temperature, then neutralized with AcOH. Volatiles were removed to give a residue, which was purified by a silica gel column, eluted with 5% MeOH in DCM to give tert-butyl allyl(-(3aR,5S,6S,7R,7aR)-5-(fluoromethyl)-6,7-dihydroxy-5,6,7,7a-tetrahydro-3aH-pyrano[3,2-d]thiazol-2-yl)carbamate as a white solid (310 mg, 86%). (ES, m/z): [M+H]$^+$ 363.0; $^1$H NMR (300 MHz, CDCl$_3$) δ 6.10 (d, J=6.9 Hz, 1H), 5.85-5.96 (m, 1H), 5.11-5.18 (m, 2H), 4.61 (d, J=2.4 Hz, 1H), 4.43-4.58 (m, 3H), 4.13-4.16 (m, 1H), 4.04-4.07 (m, 1H), 3.53-3.63 (m, 2H), 1.53 (s, 9H).

A solution of the above material (100 mg, 0.27 mmol) in MeOH (6 mL) was bubbled with dry HCl gas at room temperature until saturated. After additional 4 h, volatiles were removed to give a residue, which was re-dissolved into MeOH (5 mL) and neutralized with conc. NH$_4$OH, concentrated and purified by a silica gel column, eluted with 5%-10% MeOH in DCM to give -(3aR,5S,6S,7R,7aR)-2-(allylamino)-5-(fluoromethyl)-5,6,7,7a-tetrahydro-3aH-pyrano[3,2-d]thiazole-6,7-diol as white solid (42.7 mg, 58%). (ES, m/z): [M+H]$^+$ 263.0; $^1$H NMR (300 MHz, D$_2$O) δ 6.29 (d, J=6.3 Hz, 1H), 5.85-5.96 (m, 1H), 5.19-5.26 (m, 1H), 5.09-5.14 (m, 1H), 4.63 (d, J=3.3 Hz, 1H), 4.47 (d, J=3.6 Hz, 1H), 4.07-4.11 (m, 1H), 3.95-3.99 (m, 1H), 3.86-3.89 (m, 2H), 3.68-3.79 (m, 1H), 3.51-3.56 (m, 1H).

Example 15

(3aR,5S,6S,7R,7aR)-2-amino-5-(fluoromethyl)-5,6,7,7a-tetrahydro-3aH-pyrano[3,2-d]thiazole-6,7-diol

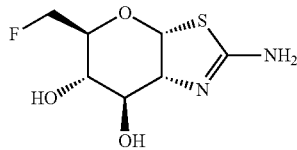 [SMILES: NC1=N[C@@H]2[C@@H](O)[C@H](O)[C@@H](CF)O[C@@H]2S1]

To a solution of -(3aR,5S,6S,7R,7aR)-2-(allyl(tert-butoxycarbonyl)amino)-5-(fluoromethyl)-5,6,7,7a-tetrahydro-3aH-pyrano[3,2-d]thiazole-6,7-diyldibenzoate (500 mg, 0.88 mmol) in 1,4-dioxane (30 mL) was added Pd(PPh$_3$)$_4$ (200 mg, 0.17 mmol), HCO$_2$H (84 mg, 1.76 mmol) and Et$_3$N (177 mg, 1.76 mmol) at room temperature under N$_2$ atmosphere. After 20 min at 60° C., additional HCO$_2$H (404 mg, 8.8 mmol) was added into the reaction mixture. The reaction was stirred for additional 2 h at 60° C., and then quenched by H$_2$O (40 mL), neutralized by NaHCO₃, extracted with DCM (3×50 mL). The combined organic layer was concentrated and purified by a silica gel column, eluted with 10% EtOAc in petroleum ether to give -(3aR,5S,6S,7R,7aR)-2-(tert-butoxycarbonylamino)-5-(fluoromethyl)-5,6,7,7a-tetrahydro-3aH-pyrano[3,2-d]thiazole-6,7-diyldibenzoate as white syrup (330 mg, 71%). (ES, m/z): [M+H]⁺ 531.0; ¹H NMR (300 MHz, CDCl₃) δ 8.30 (d, J=7.2 Hz, 2H), 8.06 (d, J=7.2 Hz, 2H), 7.46-7.66 (m, 5H), 6.46 (d, J=7.5 Hz, 1H), 5.85 (s, 1H), 5.53 (d, J=6.6 Hz, 1H), 4.71-4.79 (m, 2H), 4.62 (t, J=2.1 Hz, 1H), 3.95-4.03 (m, 1H), 1.57 (s, 9H).

A solution of the above material (330 mg, 0.62 mmol) in MeOH (10 mL) was treated with K₂CO₃ (24 mg, 0.17 mmol) for 2 h at room temperature, then neutralized by AcOH. Volatiles were removed to give a residue, which was purified by a silica gel column, eluted with 2%-5% MeOH in DCM to afford tert-butyl -(3aR,5S,6S,7R,7aR)-5-(fluoromethyl)-6,7-dihydroxy-5,6,7,7a-tetrahydro-3aH-pyrano[3,2-d]thiazol-2-ylcarbamate as white solid (170 mg, 85%). (ES, m/z): [M+H]⁺ 323.0; ¹H NMR (300 MHz, CDCl₃) δ 6.22 (d, J=6.6 Hz, 1H), 4.67-4.79 (m, 1H), 4.57-4.66 (m, 2H), 3.84-3.96 (m, 2H), 3.70 (t, J=8.4 Hz, 1H), 1.52 (s, 9H).

A solution of the above material (110 mg, 0.34 mmol) in MeOH (5 mL) was bubbled with dry HCl gas until saturated at room temperature. After additional 3 h, volatiles were removed to give a residue, which was neutralized with conc. NH₄OH and purified by a silica gel column, eluted with 10%-20% MeOH in DCM to give -(3aR,5S,6S,7R,7aR)-2-amino-5-(fluoromethyl)-5,6,7,7a-tetrahydro-3aH-pyrano[3,2-d]thiazole-6,7-diol as white solid (15 mg, 20%). (ES, m/z): [M+H]⁺ 222.9; ¹H NMR (300 MHz, D₂O) δ 6.31 (d, J=6.3 Hz, 1H), 4.63 (d, J=3.3 Hz, 1H), 4.47 (d, J=3.6 Hz, 1H), 4.07 (t, J=5.7 Hz, 1H), 3.93 (t, J=4.8 Hz, 1H), 3.66-3.80 (m, 2H), 3.51-3.58 (m, 1H).

Example 16

(3aR,5S,6S,7R,7aR)-2-(azetidin-1-yl)-5-(fluoromethyl)-5,6,7,7a-tetrahydro-3aH-pyrano[3,2-d]thiazole-6,7-diol

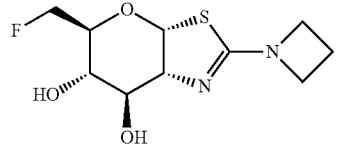 [SMILES: O[C@H]1[C@H](O)[C@@H](CF)O[C@@H]2SC(N3CCC3)=N[C@H]12]

A solution of -(3aR,5R,6S,7R,7aR)-2-(azetidin-1-yl)-5-(hydroxymethyl)-5,6,7,7a-tetrahydro-3aH-pyrano[3,2-d]thiazole-6,7-diyldibenzoate (100 mg, 0.2 mmol) in DCM (10 mL) was treated with DAST (137 mg, 0.8 mmol) for 30 min at −78° C. After stirring overnight at room temperature, the reaction was quenched with satd. aqueous NaHCO₃ (10 mL), extracted with DCM (3×10 mL), washed with brine (10 mL), dried over anhydrous Na₂SO₄ and concentrated under vacuum to give the crude product as a white syrup (80 mg), which was dissolved into MeOH (5 mL) and treated with K₂CO₃ (10 mg, 0.07 mmol) for 3 h at room temperature. The reaction mixture was neutralized by AcOH and concentrated. The residue was purified by a silica gel column, eluted with 5%-10% MeOH in DCM to give -(3aR,5S,6S,7R,7aR)-2-(azetidin-1-yl)-5-(fluoromethyl)-5,6,7,7a-tetrahydro-3aH-pyrano[3,2-d]thiazole-6,7-diol as white solid (10 mg, 17%, two steps). (ES, m/z): [M+H]⁺ 263.0; ¹H NMR (300 MHz, D₂O) δ 6.30 (d, J=6.3 Hz, 1H), 4.49-4.69 (dd, J=57, 3.3 Hz, 1H), 4.11-4.15 (m, 1H), 3.93-4.01 (m, 5H), 3.70-3.82 (m, 1H), 3.59-3.69 (m, 1H), 2.24-2.34 (m, 2H).

The following examples were synthesized according to procedures analogous to the schemes and examples outlined above.

TABLE 4

| Example | Structure | Name |
|---|---|---|
| 17 | 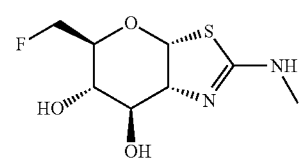 | (3aR,5S,6S,7R,7aR)-5-(fluoromethyl)-2-(methylamino)-5,6,7,7a-tetrahydro-3aH-pyrano[3,2-d]thiazole-6,7-diol |

¹H NMR (400 MHz, CD₃OD) 6.52 (d, J = 6.48 Hz, 1H), 4.66-4.52 (dt, J = 47.6, 10.4, 4.2 Hz, 2H), 4.15 (t, J = 6.5 Hz, 1H), 3.93 (t, J = 6.9 Hz, 1H), 3.87-3.76 (m, 1H), 3.59-3.55 (dd, J = 6.4, 3.12 Hz, 1H), 2.99 (s, 3H). ¹³C NMR (100 MHz, MeOD) δ 169.32, 90.48, 84.10 (d, $J_{C6,F}$ 171.5 Hz, C-6). 76.45 (d, $J_{C5,F}$ 17.8 Hz, C-5), 69.86 (d, $J_{C4,F}$ 6.6 Hz, C-4), 55.67, 46.07, 32.11. (ES, m/z): [M + H]⁺: 237.6.

| 18 | | (3aR,5S,6S,7R,7aR)-5-(fluoromethyl)-2-(propylamino)-5,6,7,7a-tetrahydro-3aH-pyrano[3,2-d]thiazole-6,7-diol |

¹H NMR (400 MHz, CD₃OD) 6.44 (d, J = 6.44 Hz, 1H), 4.67-4.49 (dt, J = 47.5, 10.4, 4.2 Hz, 2H), 4.11 (t, J = 6.4 Hz, 1H), 3.91 (t, J = 6.1 Hz, 1H), 3.82-3.72 (m, 1H), 3.52-3.55 (dd, J = 6.0, 3.4 Hz, 1H), 3.27-3.21 (m, 2H), 1.66-1.57 (m, 2H), 0.95 (t, J = 7.4 Hz, 3H). ¹³C NMR (100 MHz, MeOD) δ 167.82, 90.26, 84.10 (d, $J_{C6,F}$ 171.5 Hz, C-6), 76.34 (d, $J_{C5,F}$ 17.7 Hz, C-5), 75.80, 75.79, 70.05 (d, $J_{C4,F}$ 6.9 Hz, C-4), 55.67, 23.98, 12.38. (ES, m/z): [M + H]⁺: 265.4.

Example 19

(3aR,5S,6S,7R,7aR)-5-(difluoromethyl)-2-(ethylamino)-5,6,7,7a-tetrahydro-3aH-pyrano[3,2-d]thiazole-6,7-diol

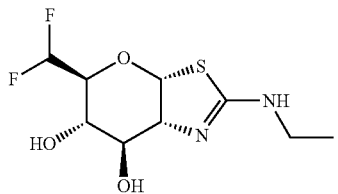 [SMILES: CCNC1=N[C@@H]2[C@@H](O)[C@H](O)[C@@H](C(F)F)O[C@@H]2S1]

To a solution of tert-butyl 43aR,5R,6S,7R,7aR)-6,7-dihydroxy-5-(hydroxymethyl)-5,6,7,7a-tetrahydro-3a14-pyrano[3,2-d]thiazol-2-yl)(ethyl)carbamate (5.01 g, 14.4 mmol) in DMF (25 mL) was added imidazole (1.57 g, 23.1 mmol) and TBDMSCl (2.82 g, 21.7 mmol). The reaction mixture stirred at room temperature for 30 h was diluted with EtOAc (100 mL). Organics were washed with satd. $NH_4Cl$, brine, dried over anhydrous $Na_2SO_4$ and concentrated. The residue was purified on silica gel by flash column chromatography (EtOAc/hexanes, 1:1), affording tert-butyl (-(3aR,5R,6S,7R,7aR)-5-(((tert-butyldimethylsily)oxy)methyl)-6,7-dihydroxy-5,6,7,7a-tetrahydro-3aH-pyrano[3,2-d]thiazol-2-yl)(ethyl)carbamate as a white solid (5.08 g, 76%). $^1$H NMR (400 MHz, $CDCl_3$) δ 6.12 (d, J=6.7 Hz, 1H), 4.25 (t, J=6.2 Hz, 1H), 4.16 (t, J=6.4 Hz, 1H), 4.10-4.04 (m, 2H), 3.91-3.85 (m, 3H), 3.65-3.62 (m, 1H), 1.55 (s, 9H), 1.26 (t, J=7 Hz, 3H), 0.89 (s, 9H), 0.08 (s, 6H).

To a solution of the above material (1.0 g, 2.2 mmol) in pyridine (20 mL), at 0° C. was added DMAP (0.024 g, 0.20 mmol) followed by BzCl (2.0 mL, 17.6 mmol) slowly. The mixture was warmed to room temperature and stirred overnight. The reaction was diluted with EtOAc (50 mL), washed with satd. $NaHCO_3$ solution and brine. The organic extract was dried over anhydrous $Na_2SO_4$ and concentrated under reduced pressure. The residual pyridine was co-evaporated with hexanes and the crude residue was separated on silica gel by flash column chromatography (EtOAc/hexanes, 1:5) to give -(3aR,5R,6S,7R,7aR)-2-((tert-butoxycarbonyl)(ethyl)amino)-5-(((tert-butyldimethylsilyl)oxy)methyl)-5,6,7,7a-tetrahydro-3aH-pyrano[3,2-d]thiazole-6,7-diyldibenzoate (1.05 g, 71.3%) as a white solid. $^1$H NMR (400 MHz, $CDCl_3$) δ 8.08 (m, 2H), 7.99 (m, 2H), 7.61-7.52 (m, 2H), 7.47-7.38 (m, 4H), 6.12 (d, J=5.6 Hz, 1H), 5.89 (dd, J=1.5, 1.4 Hz, 1H), 5.39 (m, 1H), 4.46 (ddd, J=5.5, 2.9, 0.96 Hz, 1H), 3.96 (m, 2H), 3.80 (m, 1H), 3.75-3.70 (m, 2H), 1.54 (s, 9H), 1.18 (t, J=5.5 Hz, 3H), 0.83 (s, 9H), 0.01 (s, 3H), 0.03 (s, 3H).

To a solution of the above material (3.2 g, 4.8 mmol) in dry MeOH (30 mL) was added AcCl (0.07 mL, 1.0 mmol) at 0° C. The reaction mixture was stirred at this temperature for 30 min and then at room temperature overnight. The reaction mixture was diluted with DCM (30 mL) and neutralized with 10% aq. $NaHCO_3$ solution. DCM layer was further washed with brine, dried over anhydrous $Na_2SO_4$ and concentrated. The crude residue was residue was purified by silica gel column chromatography (EtOAc/hexanes, 3:7) to provide -(3aR,5R,6S,7R,7aR)-2-((tert-butoxycarbonyl)(ethyl)amino)-5-(hydroxymethyl)-5,6,7,7a-tetrahydro-3aH-pyrano[3,2-d]thiazole-6,7-diyl dibenzoate (2.4 g, 90%) as a foamy solid. $^1$H NMR (400 MHz, $CDCl_3$) δ 8.06 (m, 2H), 8.01 (m, 2H), 7.58-7.53 (m, 2H), 7.47-7.39 (m, 4H), 6.14 (d, J=7.0 Hz, 1H), 5.93 (dd, J=1.9, 1.8 Hz, 1H), 5.34 (m, 1H), 4.49 (ddd, J=6.8, 3.6, 0.96 Hz, 1H), 4.03-3.92 (m, 2H), 3.80-3.65 (m, 3H), 1.53 (s, 9H), 1.19 (t, J=6.9 Hz, 3H).

To a solution of the above material (1.0 g, 1.8 mmol) in dry DCM (25 mL) at 0° C. was added dry pyridine (0.30 mL, 3.7 mmol), followed by DMP (1.14 g, 2.69 mmol). The reaction was stirred at 0° C. for 10 min and at room temperature for next 1.5 h. The reaction mixture was diluted with 1M $Na_2S_2O_3$/satd. $NaHCO_3$ (30 mL, 1:1) and stirred for 10 min. DCM layer was separated, dried over anhydrous $Na_2SO_4$ and concentrated to yield crude foamy solid -(3aR,5S,6S,7R,7aR)-2-((tert-butoxycarbonyl)(ethyl)amino)-5-formyl-5,6,7,7a-tetrahydro-3aH-pyrano[3,2-d]thiazole-6,7-diyldibenzoate (1.0 g crude). The product was carried forward for the next reaction without any further purification. $^1$H NMR (400 MHz, $CDCl_3$) δ 9.71 (s, 1H), 8.04 (m, 4H), 7.58 (m, 2H), 7.47-7.39 (m, 4H), 6.14 (d, J=6.24 Hz, 1H), 6.01 (dd, J=1.8, 1.3 Hz, 1H), 5.53-5.51 (m, 1H), 4.38 (ddd, J=6.2, 3.2, 1.2 Hz, 1H), 4.27 (d, J=7.3 Hz, 1H), 4.0-3.9 (m, 2H), 1.53 (s, 9H), 1.15 (t, J=6.8 Hz, 3H).

The above material (1.0 g, crude) was taken in DCM (30 mL) and cooled to −78° C. DAST (1 mL, 7.7 mmol) was added dropwise while stirring at −78° C. After the addition, cooling bath was removed and reaction mixture stirred at room temperature overnight. The reaction was diluted with satd. $NaHCO_3$ solution (15 mL). DCM layer was separated, dried over anhydrous $Na_2SO_4$ and concentrated. The crude residue was purified by silica gel column chromatography (EtOAc/hexanes, 1:4) to provide -(3aR,5S,6S,7R,7aR)-2-((tert-butoxycarbonyl)(ethyl)amino)-5-(difluoromethyl)-5,6,7,7a-tetrahydro-3aH-pyrano[3,2-d]thiazole-6,7-diyldibenzoate (0.413 g, 40%) as a foamy solid. $^1$H NMR (400 MHz, $CDCl_3$) δ 8.08 (m, 2H), 8.0 (m, 2H), 7.60-7.53 (m, 2H), 7.46-7.39 (m, 4H), 6.13 (d, J=7.0 Hz, 1H), 5.94 (m, 1H), 5.93 (td, J=54.08, 2.9 Hz, 1H), 5.59-5.56 (m, 1H), 4.55-4.52 (ddd, J=7.0, 3.4, 1.3 Hz, 1H), 3.98-3.86 (m, 3H), 1.55 (s, 9H), 1.17 (t, J=6.9 Hz, 3H).

To a stirred solution of the above material (0.41 g, 0.71 mmol) in dry MeOH (20 mL) was added $K_2CO_3$ (0.050 g, 0.36 mmol) at 0° C. The reaction mixture was warmed to room temperature and stirred 1.5 h. AcOH (0.5 mL) was added to the reaction mixture and contents were concentrated. The crude residue was purified by silica gel column chromatography (EtOAc/hexanes, 1:1) to provide tert-butyl (-(3aR,5S,6S,7R,7aR)-5-(difluoromethyl)-6,7-dihydroxy-5,6,7,7a-tetrahydro-3a14-pyrano[3,2-d]thiazol-2-yl)(ethyl)carbamate (0.24 g, 91.6%) as a foamy solid. $^1$H NMR (400 MHz, MeOD) δ 6.03 (d, J=6.6 Hz, 1H), 5.93 (td, J=54.5, 2.6 Hz, 1H), 4.19 (m, 1H), 4.11 (t, J=4.3 Hz, 1H), 3.96-3.87 (m, 2H), 3.82 (dd, J=4.7, 4.4 Hz, 1H), 3.56-3.47 (m, 1H), 1.53 (s, 9H), 1.16 (t, J=6.9 Hz, 3H).

The above material (0.24 g, 0.65 mmol) was taken in 30% TFA/DCM (10 mL) at 0° C. and stirred at this temperature for 1 h and slowly warming to room temperature for next 1 h. The reaction mixture was evaporated to dryness. The residue was neutralized with 2M $NH_3$/MeOH (5 mL) solution and purified by silica gel column chromatography (DCM/MeOH, 95:5) to provide -(3aR,5S,6S,7R,7aR)-5-(difluoromethyl)-2-(ethylamino)-5,6,7,7a-tetrahydro-3aH-pyrano[3,2-d]thiazole-6,7-diol as a white solid (0.166 g, 95.2%). $^1$H NMR (400 MHz, MeOD) δ 6.41 (d, J=6.4 Hz, 1H), 6.00 (td, J=54.4, 1.9 Hz, 1H), 4.22 (t, J=5.9 Hz, 1H), 4.01 (t, J=4.6 Hz, 1H), 3.76-3.70 (m, 2H), 3.37-3.33 (m, 2H), 1.21 (t, J=7.2 Hz, 3H).). $^{13}$C NMR (100 MHz, MeOD) δ 167.35, 116.25 (t, $J_{C6,F}$ 242.0 Hz, C-6), 89.10, 75.42 (t, J=21.0 Hz), 74.74, 71.24, 69.96 (t, J=4.0 Hz, C-4), 41.61, 15.09. ES/MS: 269.1 [M+1].

A sample of the above material (13.0 g, 48.5 mmol, 97% pure by LCMS with UV detection at 220 nm) was dissolved into boiling EtOAc (70 mL) then hexane (about 20 mL) was added dropwise until some solids appeared. The resulting solution was allowed to cool to room temperature. Solids were collected to give -(3aR,5S,6S,7R,7aR)-5-(difluoromethyl)-2-(ethylamino)-5,6,7,7a-tetrahydro-3aH-pyrano[3,2-d]thiazole-6,7-diol (10.6 g, 98.3% pure by LCMS with UV detection at 220 nm). This material exhibited spectral characteristics identical to those described above for this compound.

Example 20

(3aR,5S,6S,7R,7aR)-5-(difluoromethyl)-2-(dimethylamino)-5,6,7,7a-tetrahydro-3aH-pyrano[3,2-d]thiazole-6,7-diol

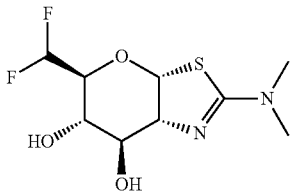

To a solution of -(3aR,5R,6S,7R,7aR)-2-(dimethylamino)-5-(hydroxymethyl)-5,6,7,7a-tetrahydro-3aH-pyrano[3,2-d]thiazole-6,7-diol (0.944 g, 3.8 mmol) in DMF (5 mL) was added imidazole (0.8 g, 12 mmol) and TBDMSCl (0.75 g, 4.97 mmol). The reaction mixture was stirred at room temperature for 18 h and concentrated using high vacuum. The crude residue was purified on silica gel by flash column chromatography (DCM/MeOH, 95:5), affording -(3aR,5R,6S,7R,7aR)-5-(((tert-butyldimethylsilypoxy)methyl)-2-(dimethylamino)-5,6,7,7a-tetrahydro-3aH-pyrano[3,2-d]thiazole-6,7-diol as a white solid (0.76 g, 55.2%). $^1$H NMR (400 MHz, MeOD) δ 6.31 (d, J=6.4 Hz, 1H), 4.06 (t, J=6.1 Hz, 1H), 3.92-3.88 (m, 2H), 3.81-3.76 (dd, J=11.4, 5.7 Hz, 1H), 3.62-3.58 (m, 1H), 3.52-3.48 (dd, J=9.3, 5.5 Hz, 1H), 3.02 (s, 6H), 0.93 (s, 9H), 0.10 (s, 6H).

To a solution of the above material (0.84 g, 2.31 mmol) in pyridine (10 mL), at 0° C. was added DMAP (0.028 g, 0.23 mmol) followed by BzCl (1.6 mL, 13.8 mmol) slowly. The mixture was warmed to room temperature and stirred overnight. The reaction was diluted with EtOAc (50 mL), washed with satd. NaHCO$_3$ solution and brine. The organic extract was dried over anhydrous Na$_2$SO$_4$ and concentrated under reduced pressure. The residual pyridine was co-evaporated with hexanes and the crude residue was separated on silica gel by flash column chromatography (EtOAc/hexanes, 2:3) to give (3aR,5R,6S,7R,7aR)-5-(((tert-butyldimethylsilypoxy)methyl)-2-(dimethylamino)-5,6,7,7a-tetrahydro-3aH-pyrano[3,2-d]thiazole-6,7-diyldibenzoate (0.9 g, 68.4%) as a foamy white solid. $^1$H NMR (400 MHz, CDCl$_3$) δ 8.04-8.01 (m, 4H), 7.53-7.47 (m, 2H), 7.40-7.32 (m, 4H), 6.36 (d, J=5.2 Hz, 1H), 5.81 (t, J=2.4 Hz, 1H), 5.35-5.33 (dd, J=7.1, 0.9 Hz, 1H), 4.59 (t, J=4.2 Hz, 1H), 3.92-3.89 (m, 1H), 3.80-3.73 (m, 2H), 3.05 (s, 6H), 0.83 (s, 9H), 0.01 (s, 6H).

To a solution of the above material (0.88 g, 1.54 mmol) in dry MeOH (6 mL) was added AcCl (0.054 mL, 0.77 mmol) at 0° C. The reaction mixture was stirred at this temperature for 30 min and then at room temperature overnight. The reaction mixture was diluted with DCM (30 mL) and neutralized with 10% aq. NaHCO$_3$ solution. DCM layer was further washed with brine, dried over anhydrous Na$_2$SO$_4$ and concentrated. The crude residue was residue was purified by silica gel column chromatography (EtOAc/hexanes, 1:1) to provide -(3aR,5R,6S,7R,7aR)-2-(dimethylamino)-5-(hydroxymethyl)-5,6,7,7a-tetrahydro-3aH-pyrano-[3,2-d]thiazole-6,7-diyldibenzoate (0.57 g, 81%) as a foamy solid. $^1$H NMR (400 MHz, CDCl$_3$) δ 8.03-8.01 (m, 4H), 7.55-7.49 (m, 2H), 7.41-7.37 (m, 4H), 6.36 (d, J=6.5 Hz, 1H), 5.84-5.83 (dd, J=4.3, 3.0 Hz, 1H), 5.32-5.28 (m, 1H), 4.57 (t, J=5.2 Hz, 1H), 3.92-3.88 (m, 1H), 3.78-3.75 (dd, J=12.4, 2.5 Hz, 1H), 3.70-3.65 (dd, J=12.4, 5.4 Hz, 1H), 3.03 (s, 6H).

To a solution of the above material (0.57 g, 1.25 mmol) in dry DCM (10 mL) at 0° C. was added DMP (0.8 g, 1.88 mmol). The reaction was stirred at 0° C. for 10 min and at room temperature for next 1.5 h when the starting material was completely consumed. The reaction mixture was diluted 1:1 1M Na$_2$S$_2$O$_3$: Satd. NaHCO$_3$ (30 mL) and stirred for 10 min. DCM layer was separated, dried over anhydrous Na$_2$SO$_4$ and concentrated to yield crude foamy solid containing -(3aR,5S,6S,7R,7aR)-2-(dimethylamino)-5-formyl-5,6,7,7a-tetrahydro-3aH-pyrano[3,2-d]thiazole-6,7-diyldibenzoate (0.56 g crude). The crude product was carried forward for the next reaction without any further purification.

The above material (0.56 g, crude) was taken in DCM (10 mL) and cooled to −78° C. DAST (0.72 mL, 5.5 mmol) was added dropwise while stirring at −78° C. After the addition, cooling bath was removed and reaction mixture stirred at room temperature overnight. The reaction was diluted with satd. NaHCO$_3$ solution (15 mL). DCM layer was separated, dried over anhydrous Na$_2$SO$_4$ and concentrated. The crude residue was purified by silica gel column chromatography (EtOAc/hexanes, 1:4) to provide -(3aR,5S,6S,7R,7aR)-5-(difluoromethyl)-2-(dimethylamino)-5,6,7,7a-tetrahydro-3aH-pyrano[3,2-d]thiazole-6,7-diyl dibenzoate (0.330 g, 55.2% over 2 steps) as a foamy solid. $^1$H NMR (400 MHz, CDCl$_3$) δ 8.06-8.01 (m, 4H), 7.57-7.53 (m, 2H), 7.44-7.39 (m, 4H), 6.38 (d, J=5.3 Hz, 1H), 5.99-5.77 (m, 1H), 5.85 (m, 1H), 5.54 (d, J=6.8 Hz, 1H), 4.66-4.64 (m, 1H), 4.06-4.01 (m, 1H), 3.06 (s, 6H).

To a stirred solution of the above material (0.33 g, 0.69 mmol) in dry MeOH (8 mL) was added K$_2$CO$_3$ (0.073 g, 0.53 mmol) at 0° C. The reaction mixture was warmed to room temperature and stirred 1.5 h. AcOH (0.5 mL) was added to the reaction mixture and contents were concentrated. The AcOH salt thus obtained was treated with 2M NH$_3$/MeOH solution (8 mL) and again concentrated. The residue was purified by silica gel column chromatography (DCM/MeOH, 9:1) to provide -(3aR,5S,6S,7R,7aR)-5-(difluoromethyl)-2-(dimethylamino)-5,6,7,7a-tetrahydro-3aH-pyrano[3,2-d]thiazole-6,7-diol as a foamy solid (0.1 g, 54%). $^1$H NMR (400 MHz, MeOD) δ 6.31 (d, J=6.4 Hz, 1H), 5.98 (td, J=54.1, 2.0 Hz, 1H), 4.20 (t, J=5.6 Hz, 1H), 4.04 (t, J=4.7 Hz, 1H), 3.78-3.66 (m, 2H), 3.03 (s, 6H). $^{13}$C NMR (100 MHz, MeOD) δ 166.20, 116.56 (t, $J_{C6,F}$ 241.2 Hz, C-6), 91.41, 77.21, 75.57, 75.04 (t, J=21.0 Hz), 70.68 (t, J=3.3 Hz, C-4), 41.17. ES/MS: 269.1 [M+1].

Example 21

(3aR,5S,6S,7R,7aR)-2-(allylamino)-5-(difluoromethyl)-5,6,7,7a-tetrahydro-3aH-pyrano[3,2-d]thiazole-6,7-diol

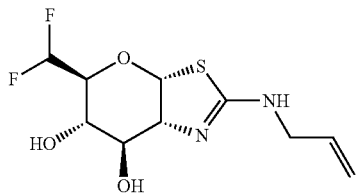 [SMILES: C=CCNC1=N[C@@H]2[C@@H](O)[C@H](O)[C@@H](C(F)F)O[C@@H]2S1]

A mixture of prop-2-en-1-amine (9.2 g, 0.16 mol) and (2S,3R,4R,5S,6R)-6-(acetoxymethyl)-β-isothiocyanatotetrahydro-2H-pyran-2,4,5-triyltriacetate (60 g, 0.154 mol) in DCM (300 mL) was stirred for 1 h at room temperature, followed by addition of TFA (88 g, 0.77 mol). The resulting solution was stirred overnight at room temperature, and was quenched with aqueous NaHCO$_3$ to pH at 8, and extracted with DCM (3×300 mL). The combined organic layer was dried over anhydrous Na$_2$SO$_4$, and condensed to give a residue, which was purified by a silica gel column with 1%~2% MeOH in DCM to give -(3aR,5R,6S,7R,7aR)-5-(acetoxymethyl)-2-(allylamino)-5,6,7,7a-tetrahydro-3aH-pyrano[3,2-d]thiazole-6,7-diyl diacetate as a yellow liquid (58 g, 84%). (ES, m/z): [M+H]$^+$ 387.0; $^1$H NMR (300 MHz, CDCl$_3$) δ 6.33 (d, J=6.6 Hz, 1H), 5.84-5.96 (m, 1H), 5.32-5.44 (m, 4H), 4.98-5.04 (m, 1H), 4.37 (t, J=5.7 Hz, 1H), 4.28-4.22 (m, 2H), 3.92-3.95 (m, 3H), 2.14 (s, 3H), 2.12 (s, 3H), 2.11 (s, 3H).

A solution of the above material (50 g, 0.13 mol) in MeOH (300 mL) was treated with K$_2$CO$_3$ (3.6 g, 0.26 mol) overnight at room temperature, and followed by addition of Boc$_2$O (56 g, 0.26 mol) and Et$_3$N (19.6 g, 0.19 mol). After additional 2 h, the resulting solution was concentrated to give a residue, which was purified by a silica gel column, eluted with 5% MeOH in DCM to give tert-butyl allyl(-(3aR,5R,6S,7R,7aR)-6,7-dihydroxy-5-(hydroxymethyl)-5,6,7,7a-tetrahydro-3aH-pyrano[3,2-d]thiazol-2-yl)carbamate as an oil (42 g, 90% in two steps). (ES, m/z): [M+H]$^+$ 361.0; $^1$H NMR (300 MHz, CDCl$_3$) δ 6.14 (d, J=6.9 Hz, 1H), 5.84-5.96 (m, 1H), 5.22-5.44 (m, 4H), 4.37-4.38 (m, 1H), 4.22-4.28 (m, 2H), 3.92-3.95 (m, 3H), 1.54 (s, 9H).

A mixture of TBDMSCl (26 g, 0.17 mmol), DMAP (1.4 g, 0.01 mol), Et$_3$N (23.5 g, 0.23 mmol) and the above material (42 g, 0.12 mol) in DCM (300 mL) was stirred overnight at 40° C. The reaction mixture was quenched by satd. aqueous NaHCO$_3$ (20 mL), and was condensed to give a residue, which was purified by a silica gel column, eluted with 1%-2% MeOH in DCM to give tert-butyl allyl(-(3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl)carbamate as a light yellow syrup (48 g, 87%). (ES, m/z): [M+H]$^+$ 474.9; $^1$H NMR (300 MHz, CDCl$_3$) δ 6.16 (d, J=6.6 Hz, 1H), 5.84-5.93 (m, 1H), 5.22-5.32 (m, 4H), 4.65-4.67 (m, 1H), 4.26-4.31 (m, 1H), 4.20-4.22 (m, 1H), 3.84-3.88 (m, 3H), 1.54 (s, 9H), 0.93 (s, 9H), 0.09 (s, 6H).

A mixture of BzCl (11.1 g, 79 mmol), DMAP (322 mg, 2.63 mmol), pyridine (20.8 g, 263 mmol) and the above material (12.5 g, 26.3 mmol) in DCM (150 mL) at 0° C. was stirred overnight at room temperature. The reaction mixture was quenched with satd. aqueous NaHCO$_3$ (200 mL), extracted with DCM (3×100 mL), washed with brine (3×50 mL), dried over anhydrous MgSO$_4$, and condensed to give a residue, which was purified by a silica gel column with 10% EtOAc in petroleum ether to afford -(3aR,5R,6S,7R,7aR)-2-(allyl(tert-butoxycarbonyl)amino)-5-((tert-butyl-dimethylsilyloxy)methyl)-5,6,7,7a-tetrahydro-3aH-pyrano[3,2-d]thiazole-6,7-diyldibenzoate as a white solid (16.5 g, 78%). (ES, m/z): [M+H]$^+$ 683.1; $^1$H NMR (300 MHz, CDCl$_3$) δ 8.05-8.10 (m, 4H), 7.56-7.61 (m, 2H), 7.42-7.47 (m, 4H), 6.27 (d, J=7.2 Hz, 1H), 5.99-6.02 (m, 2H), 5.86-5.92 (m, 1H), 5.43-5.46 (m, 1H), 5.10-5.18 (m, 2H), 4.81-4.89 (m, 1H), 4.56-4.62 (m, 2H), 3.76-3.87 (m, 3H), 1.56 (s, 9H), 0.88 (s, 9H), 0.04 (s, 6H).

A solution of the above material (7.0 g, 10.3 mmol) in MeOH (50 mL) was treated with AcCl (0.5 mL, 0.07 mmol) for 3 h at room temperature. The reaction mixture was quench with satd. aqueous NaHCO$_3$ (10 mL) and water (200 mL), extracted with DCM (3×50 mL), dried over anhydrous MgSO$_4$, and concentrated under vacuum to give a residue, which was purified by a silica gel column with 10% EtOAc in petroleum ether to give -(3aR,5R,6S,7R,7aR)-2-(allyl(tert-butoxycarbonyl)amino)-5-(hydroxymethyl)-5,6,7,7a-tetrahydro-3aH-pyrano[3,2-d]thiazole-6,7-diyl dibenzoate as a white syrup (1.7 g, 29%). (ES, m/z): [M+H]$^+$ 569.0; $^1$H NMR (300 MHz, CDCl$_3$) δ 8.06-8.09 (m, 4H), 7.60-7.63 (m, 2H), 7.43-7.58 (m, 4H), 6.26 (d, J=6.9 Hz, 1H), 6.06-6.27 (m, 2H), 5.37-5.41 (d, J=8.4 Hz, 1H), 5.11-5.28 (m, 2H), 4.82-4.84 (m, 1H), 4.56-4.62 (m, 2H), 3.71-3.86 (m, 3H), 1.56 (s, 9H).

A solution of the above material (1.5 g, 2.6 mmol) in DCM (30 mL) was treated with DMP (1.7 g, 4.0 mmol) for 2 h at room temperature. The resulting solution was quenched with satd. aqueous NaHCO$_3$ (10 mL) and satd. aqueous Na$_2$S$_2$O$_3$ (10 mL), extracted with DCM (3×50 mL), dried over Na$_2$SO$_4$, and concentrated under vacuum to give a residue, which was purified by a short silica gel column with 30% EtOAc in petroleum to afford the crude aldehyde (1.3 g), which was dissolved into DCM (20 mL) and treated with DAST (1.5 g, 9.3 mmol) at −78° C. After stirred overnight at room temperature, the resulting solution was quenched with satd. aqueous NaHCO$_3$ (50 mL), extracted with DCM (3×50 mL), dried over Na$_2$SO$_4$, and concentrated under vacuum to give a residue, which was purified by a silica gel column with 10% EtOAc in petroleum to give -(3aR,5S,6S,7R,7aR)-2-(allyl(tert-butoxycarbonyl)amino)-5-(difluoromethyl)-5,6,7,7a-tetrahydro-3aH-pyrano[3,2-d]thiazole-6,7-diyl dibenzoate as a white solid (650 mg, 43%). (ES, m/z): [M+H]$^+$ 589.0; $^1$H NMR (300 MHz, CDCl$_3$), δ 8.03-8.13 (m, 4H), 7.56-7.61 (m, 2H), 7.48-7.51 (m, 4H), 6.11-6.14 (d, J=8.7 Hz, 1H), 5.95-6.09 (td, J=54.3 Hz, 2.8 Hz, 1H), 5.19-5.25 (m, 2H), 4.44-4.45 (m, 2H), 4.31-4.36 (m, 2H), 4.10-4.18 (m, 2H), 1.53 (s, 9H).

A solution of the above material (200 mg, 0.34 mmol) in MeOH (15 mL) was treated with K$_2$CO$_3$ (10 mg, 0.07 mmol) for 3 h at room temperature. The reaction mixture was neutralized by acetate acid, and was condensed to give a residue, which was purified by a silica gel column, eluted with 1%-2% MeOH in DCM to give tert-butyl allyl(-(3aR,5S,6S,7R,7aR)-5-(difluoromethyl)-6,7-dihydroxy-5,6,7,7a-tetrahydro-3aH-pyrano[3,2-d]thiazol-2-yl)carbamate as a yellow oil (150 mg, 76%). (ES, m/z): [M+H]$^+$ 381.0; $^1$H NMR (300 MHz, CDCl$_3$) δ 6.13 (d, J=8.7 Hz, 1H), 5.95-6.09 (m, 1H), 5.19-5.25 (m, 2H), 4.44-4.45 (m, 2H), 4.31-4.36 (m, 2H), 4.10-4.18 (m, 2H), 1.53 (s, 9H).

A solution of the above material (150 mg, 0.39 mmol) in DCM (18 mL) was treated with TFA (1.8 mL) overnight at room temperature. The reaction mixture was condensed to give a residue, which was neutralized by NH$_4$OH (0.5 mL, 25%-28%, w/v) for purification by Prep-HPLC under the following conditions [(Agilent 1200 prep HPLC; Column: Sun Fire Prep C18, 19*50 mm Sum; mobile phase: Water with 0.03% NH$_4$OH and CH$_3$CN (10% CH$_3$CN up to 45% in 10 min; Detector: UV 220 nm) to give -(3aR,5S,6S,7R,7aR)-2-(allylamino)-5-(difluoromethyl)-5,6,7,7a-tetrahydro-3aH-pyrano[3,2-d]thiazole-6,7-diol as a white solid (16.6 mg, 15%). [M+H]$^+$ 281.0; $^1$H NMR (300 MHz, D$_2$O) δ 6.20 (d, J=6.3 Hz, 1H), 6.14-6.16 (m, 1H), 5.74-5.78 (t, J=2.7 Hz, 1H), 5.04-5.10 (m, 2H), 4.20-4.24 (t, J=6.0 Hz, 1H), 4.04-4.07 (t, J=4.2 Hz, 1H), 3.66-3.86 (m, 4H).

Example 22

3aR,5S,6S,7R,7aR)-2-amino-5-(difluoromethyl)-5,6,7,7a-tetrahydro-3aH-pyrano[3,2-d]thiazole-6,7-diol

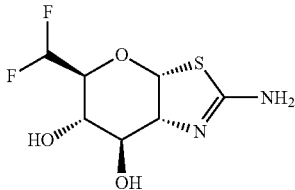 [SMILES: NC1=N[C@@H]2[C@@H](O)[C@H](O)[C@@H](C(F)F)O[C@@H]2S1]

To a solution of -(3aR,5S,6S,7R,7aR)-2-(allyl(tert-butoxycarbonyl)amino)-5-(difluoromethyl)-5,6,7,7a-tetrahydro-3aH-pyrano[3,2-d]thiazole-6,7-diyldibenzoate (900 mg, 1.53 mmol) in 1,4-dioxane (30 mL) was added Pd(PPh$_3$)$_4$ (347 mg, 0.30 mmol), HCO$_2$H (384 mg, 8.35 mmol) and Et$_3$N (846 mg, 8.38 mmol) under N$_2$ atmosphere at 10° C. After 20 min at 60° C., additional HCO$_2$H (1.4 g, 30.3 mmol) was added. After stirred overnight at 60° C., the reaction mixture was quenched with satd. aqueous NaHCO$_3$, extracted with DCM (3×30 mL), dried by anhydrous MgSO$_4$, and concentrated under reduced pressure to afford a residue, which was purified by a silica gel column, eluted with 10% EtOAc in hexane to give -(3aR,5S,6S,7R,7aR)-2-(tert-butoxycarbonylamino)-5-(difluoromethyl)-5,6,7,7a-tetrahydro-3aH-pyrano[3,2-d]thiazole-6,7-diyldibenzoate as a white syrup (600 mg, 72%). (ES, m/z): [M+H]$^+$ 549.0; $^1$H NMR (300 MHz, CDCl$_3$) δ 8.07-8.14 (m, 4H), 7.60-7.65 (m, 2H), 7.51-7.59 (m, 4H), 6.34 (d, J=8.7 Hz, 1H), 5.82-6.20 (td, J=54.0 Hz, 2.7 Hz, 1H), 5.83-5.85 (m, 1H), 5.61-5.64 (m, 1H), 4.59-4.63 (m, 1H), 4.05-4.18 (m, 1H), 1.53 (s, 9H).

A solution of the above material (600 mg, 1.1 mmol) in MeOH (50 mL) was treated with K$_2$CO$_3$ (45 mg, 0.33 mmol) for 3 h at room temperature. The reaction mixture was neutralized by addition of AcOH, and was condensed to give a residue, which was purified by a silica gel column eluted with 1% 5% MeOH in DCM to give tert-butyl -(3aR,5S,6S,7R,7aR)-5-(difluoromethyl)-6,7-dihydroxy-5,6,7,7a-tetrahydro-3aH-pyrano[3,2-d]thiazol-2-ylcarbamate as a solid (300 mg, 81%). (ES, m/z): [M+H]$^+$ 341.0; $^1$H NMR (300 MHz, CDCl$_3$) δ 6.17 (d, J=6.6 Hz, 1H), 5.85-6.21 (td, J=51.6 Hz, 2.7 Hz, 1H), 3.84-4.16 (m, 4H), 1.56 (s, 9H).

A solution of the above material (135 mg, 0.4 mmol) in DCM (10 mL) was treated with TFA (1 mL) overnight at room temperature. Removal of solvents gave a residue, which was dissolved into MeOH (5 mL) and neutralized by conc. NH$_4$OH (0.5 mL, 25%~28%, w/v). Concentration and purification by Prep-HPLC under the following conditions [(Agilent 1200): Column, X-Bridge C18; mobile phase, 50 mmol/L NH$_4$HCO$_3$ in water with 0.05% NH$_4$OH and CH$_3$CN (CH$_3$CN 5% up to 20% in 10 min); Detector, 220 nm UV] afforded -(3aR,5S,6S,7R,7aR)-2-amino-5-(difluoromethyl)-5,6,7,7a-tetrahydro-3aH-pyrano[3,2-d]thiazole-6,7-diol as a white solid (26.7 mg, 27%). (ES, m/z): [M+H]$^+$ 240.9; $^1$H NMR (CD$_3$OD, 300 MHz) δ 6.28 (d, J=6.3 Hz, 1H), 5.50-6.14 (td, J=54.3 Hz, 2.1 Hz, 1H), 4.16-4.20 (m, 1H), 4.02-4.05 (t, J=4.5 Hz, 1H), 3.74-3.80 (m, 1H), 3.63-3.71 (m, 1H).

Example 23

(3aR,5S,6S,7R,7aR)-5-(difluoromethyl)-2-(prop-2-ynylamino)-5,6,7,7a-tetrahydro-3aH-pyrano[3,2-d]thiazole-6,7-diol

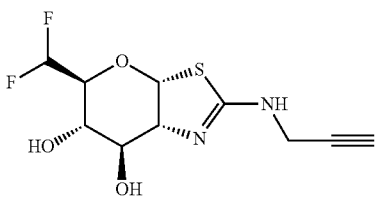

A solution of -(3aR,5S,6S,7R,7aR)-2-(tert-butoxycarbonylamino)-5-(difluoromethyl)-5,6,7,7a-tetrahydro-3aH-pyrano[3,2-d]thiazole-6,7-diyldibenzoate (800 mg, 1.46 mmol) and 3-bromoprop-1-yne (538 mg, 4.56 mmol) in DMF (15 mL) was treated with K$_2$CO$_3$ (125 mg, 0.91 mmol) overnight at room temperature. The reaction mixture was quenched with satd. aqueous NH$_4$Cl (30 mL), extracted with DCM (3×10 mL), washed with brine (3×10 mL), dried over anhydrous MgSO$_4$, and condensed to give a residue, which was purified by a silica gel column with 10% EtOAc in petroleum ether to give a mixture containing -(3aR,5S,6S,7R,7aR)-2-(tert-butoxycarbonyl(prop-2-ynyl)amino)-5-(difluoromethyl)-5,6,7,7a-tetrahydro-3aH-pyrano[3,2-d]thiazole-6,7-diyldibenzoate as a light yellow solid (210 mg), which was used in the next step without further purification. (ES, m/z): [M+H]$^+$ 587.0.

A solution of above mixture (210 mg, 0.36 mmol) in MeOH (10 mL) was treated with K$_2$CO$_3$ (14.8 mg, 0.11 mmol) for 2 h at 25° C., and followed by neutralization with AcOH. Removal of volatiles afforded a residue, which was purified by a silica gel column with 20% EtOAc in petroleum ether to give a mixture containing tert-butyl -(3aR,5S,6S,7R,7aR)-5-(difluoromethyl)-6,7-dihydroxy-5,6,7,7a-tetrahydro-3aH-pyrano[3,2-d]thiazol-2-yl(prop-2-ynyl)carbamate (125 mg). (ES, m/z): [M+H]$^+$ 379.0.

A solution of above mixture (50 mg, 0.1 mmol) in THF (10 mL) was treated with MeMgCl (0.3 mL, 1 mmol, 3 M in THF) overnight at 10° C. The reaction was quenched with satd. aqueous N$_{H4}$Cl (1 mL), and was condensed to give a residue, which was dissolved into 10% MeOH in DCM, and filtered through a short silica gel column. Concentration and purification by Prep-HPLC under the following conditions [(Agilent 1200 prep HPLC): Column, Sun Fire Prep C18*50 mm Sum; mobile phase, H$_2$O with CH$_3$CN (40% CH$_3$CN up to 60% in 5 min); Detector, UV, 220 nm] afforded -(3aR,5S,6S,7R,7aR)-5-(difluoromethyl)-2-(prop-2-ynylamino)-5,6,7,7a-tetrahydro-3aH-pyrano[3,2-d]thiazole-6,7-diol (22 mg, faster moving isomer by HPLC). (ES, m/z): [M+H]$^+$ 279.0; $^1$H NMR (300 MHz, DMSO) δ 7.37 (broad, 1H), 6.21 (d, J=6.3 Hz, 1H), 5.76-6.28 (td, J=53.7 Hz, 2.1 Hz, 1H), 5.27 (d, J=4.5 Hz, 1H), 4.96-4.98 (d, J=6.3 Hz, 1H), 4.05-4.09 (m, 1H), 3.85-3.99 (m, 3H), 3.51-3.60 (m, 2H), 3.13 (s, 1H).

Example 24

(3aR,5S,6S,7R,7aR)-2-(azetidin-1-yl)-5-(difluoromethyl)-5,6,7,7a-tetrahydro-3aH-pyrano[3,2-d]thiazole-6,7-diol

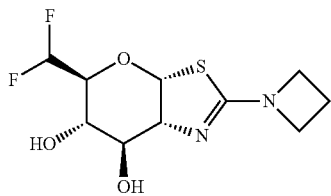 [SMILES: O[C@H]1[C@H](O)[C@@H](C(F)F)O[C@@H]2SC(N3CCC3)=N[C@H]12]

A mixture of Et₃N (18.7 g, 185 mmol), azetidine hydrochloride (12 g, 129 mmol) and (2S,3R,4R,5S,6R)-6-(acetoxymethyl)-β-isothiocyanatotetrahydro-2H-pyran-2,4,5-triyl triacetate (48 g, 123 mmol) in DCM (500 mL) was stirred for 2 h at room temperature, and followed by addition of TFA (56 g, 493 mmol). The resulting solution was stirred overnight at room temperature, neutralized by NaHCO₃, extracted with DCM (3×100 mL), dried over anhydrous Na₂SO₄, and condensed to give a residue, which was purified by a silica gel column, eluted with 30% EtOAc in petroleum to give -(3aR, 5R,6S,7R,7aR)-5-(acetoxymethyl)-2-(azetidin-1-yl)-5,6,7, 7a-tetrahydro-3aH-pyrano[3,2-d]thiazole-6,7-diyl diacetate as a light yellow syrup (36 g, 75%). (ES, m/z): [M+H]⁺ : 386.9; ¹H NMR (300 MHz, CDCl₃) δ 6.29 (d, J=6.6 Hz, 1H), 5.44-5.47 (m, 1H), 4.95-4.99 (m, 1H), 4.36 (t, J=5.4 Hz, 1H), 4.05-4.18 (m, 6H), 3.86-3.92 (m, 1H), 2.34-2.44 (m, 2H), 2.07-2.14 (m, 9H).

A solution of the above material (36 g, 93 mmol) in MeOH (200 mL) was treated with K₂CO₃ (5.14 g, 37 mmol) for 4 h at room temperature. The resulted solution was filtered through a short silica gel column to afford -(3aR,5R,6S,7R, 7aR)-2-(azetidin-1-yl)-5-(hydroxymethyl)-5,6,7,7a-tetrahydro-3aH-pyrano[3,2-d]thiazole-6,7-diol as light yellow syrup (21 g, 87%). (ES, m/z): [M+H]⁺ : 261.0; ¹H NMR (300 MHz, DMSO) δ 6.27 (d, J=6.3 Hz, 1H), 3.94 (t, J=6.3 Hz, 1H), 3.85 (t, J=7.5 Hz, 4H), 3.70 (t, J=4.8 Hz, 1H), 3.55-3.59 (m, 1H), 3.33-3.42 (m, 3H), 2.21-2.51 (m, 2H).

To a solution of the above material (34 g, 131 mmol), Et₃N (20.2 g, 0.2 mol) and DMAP (0.5 g, 4 mmol) in DCM (200 mL) was added TBDMSCl (21.6 g, 143 mmol). After stirred overnight at 15° C., the reaction mixture was quenched by addition of satd. aqueous NaHCO₃ (200 mL), extracted with DCM (3×100 mL), dried over anhydrous Na₂SO₄, and concentrated under vacuum to give a residue, which was purified on a silica gel column with 2% MeOH in DCM to afford -(3aR,5R,6S,7R,7aR)-2-(azetidin-1-yl)-5-((tert-butyldimethylsilyloxy)methyl)-5,6,7,7a-tetrahydro-3aH-pyrano[3,2-d]thiazole-6,7-diol as a solid (32 g, 65%). (ES, m/z): [M+H]⁺ : 375.0; ¹H NMR (300 MHz, CDCl₃) δ 6.38 (d, J=6.3 Hz, 1H), 4.24 (t, J=6.3 Hz, 1H), 4.04-4.09 (m, 5H), 3.85 (d, J=3.6 Hz, 2H), 3.70-3.78 (m, 1H), 3.66-3.69 (m, 1H), 2.33-2.43 (m, 2H), 0.91 (s, 9H), 0.09 (s, 6H).

A solution of the above material (3.0 g, 8.0 mmol) in DMF (40 mL) was treated with NaH (1.5 g, 37.50 mmol) at room temperature for 30 min, and followed by addition of BzCl (3.36 g, 24 mmol). The resulting solution was stirred overnight at 15° C., quenched with water/ice (100 mL), extracted with DCM (3×50 mL), washed with brine (3×20 mL), dried over anhydrous Na₂SO₄, and condensed to give a residue, which was purified by a silica gel column with 10% EtOAc in petroleum ether to afford -(3aR,5R,6S,7R,7aR)-2-(azetidin-1-yl)-5-((tert-butyldimethylsilyloxy)methyl)-5,6,7,7a-tetrahydro-3aH-pyrano[3,2-d]thiazole-6,7-diyl dibenzoate as light yellow oil (1.38 g, 30%). (ES, m/z): [M+H]⁺ : 583.0; ¹H NMR (300 MHz, CDCl₃) δ 8.05-8.09 (m, 4H), 7.54-7.59 (m, 2H), 7.28-7.39 (m, 4H), 6.43 (d, J=6.3 Hz, 1H), 5.84-5.96 (m, 1H), 5.37 (dd, J=2.1, 1.5 Hz, 1H), 4.59-4.61 (m, 1H), 4.04-4.09 (m, 5H), 3.78-3.93 (m, 2H), 2.38-2.43 (m, 2H), 0.91 (s, 9H), 0.09 (s, 6H).

A solution of the above material (1.3 g, 2.2 mmol) in MeOH (10 mL) was treated with AcCl (1 mL, 0.45 mmol) overnight at 15° C. The reaction was quenched with satd. aqueous NaHCO₃ (20 mL), extracted with DCM (3×40 mL), dried over anhydrous Na₂SO₄, and concentrated under vacuum to give a residue, which was purified by a silica gel column, eluted with 20% EtOAc in petroleum ether to afford -(3aR,5R,6S,7R,7aR)-2-(azetidin-1-yl)-5-(hydroxymethyl)-5,6,7,7a-tetrahydro-3aH-pyrano[3,2-d]thiazole-6,7-diyldibenzoate as a solid (0.42 g, 40%). (ES, m/z): [M+H]⁺ : 469.0; ¹H NMR (300 MHz, CDCl₃) δ 8.04-8.11 (m, 4H), 7.55-7.62 (m, 2H), 7.42-7.48 (m, 4H), 6.48 (d, J=6.6 Hz, 1H), 5.92 (t, J=3.6 Hz, 1H), 5.35 (dd, J=8.0, 3.6 Hz, 1H), 4.63 (t, J=5.4 Hz, 1H), 4.11-4.18 (m, 4H), 3.92-3.96 (m, 1H), 3.80-3.84 (m, 1H), 3.69-3.68 (m, 1H), 2.38-2.48 (m, 2H).

A solution of the above material (400 mg, 0.85 mmol) in DCM (20 mL) was treated with DMP (600 mg, 1.41 mmol) at 0° C. for 10 min, and additional 2 h at 25° C. The resulting solution was quenched with satd. aqueous NaHCO₃ (10 mL) and satd. aqueous Na₂S₂O₃ (10 mL), extracted with DCM (3×20 mL), dried over anhydrous Na₂SO₄, and concentrated under vacuum to afford a residue, which was dissolved into DCM (20 mL) and treated with DAST (5 mL, 4.48 mmol) at −78° C. The resulted solution was stirred overnight at 15° C., and was quenched with satd. aqueous NaHCO₃ (10 mL). The organic layer was separated and the resulted aqueous layer was extracted with DCM (2×20 mL). The combined organic layers was dried over anhydrous Na₂SO₄ and concentrated under vacuum. The residue was purified by a silica gel column with 20% EtOAc in petroleum ether to afford -(3aR,5S, 6S,7R,7aR)-2-(azetidin-1-yl)-5-(difluoromethyl)-5,6,7,7a-tetrahydro-3aH-pyrano[3,2-d]thiazole-6,7-diyl dibenzoate as light yellow oil (240 mg, 46%). (ES, m/z): [M+H]⁺ : 488.9; ¹H NMR (300 MHz, CDCl₃) δ 8.03-8.13 (m, 4H), 7.56-7.63 (m, 2H), 7.42-7.49 (m, 4H), 6.48 (d, J=6.6 Hz, 1H), 5.94-5.96 (m, 2H), 5.58 (d, J=8.7 Hz, 1H), 4.73 (s, 1H), 4.07-4.17 (m, 4H), 2.43-2.51 (m, 2H).

A solution of the above material (110 mg, 0.23 mmol) in MeOH (10 mL) was treated with K₂CO₃ (20 mg, 0.14 mmol) for 2 h at 25° C., and then neutralized by AcOH. Removal of volatiles gave a residue, which was purified by a silica gel column with 10% MeOH in DCM to afford -(3aR,5S,6S,7R, 7aR)-2-(azetidin-1-yl)-5-(difluoromethyl)-5,6,7,7a-tetrahydro-3aH-pyrano[3,2-d]thiazole-6,7-diol as a white solid (24 mg, 22%). (ES, m/z): [M+H]⁺ : 280.9; ¹H NMR (300 MHz, D₂O) δ 6.29 (d, J=6.3 Hz, 1H), 5.82-6.00 (td, J=54.0 Hz, 1.8 Hz, 1H), 4.24 (t, J=5.7 Hz, 1H), 3.97-4.04 (m, 5H), 3.82-3.87 (m, 1H), 3.69-3.80 (m, 1H), 2.29 (m, 2H).

The following examples were synthesized according to procedures analogous to the schemes and examples outlined above.

TABLE 5

| Example | Structure | Name |
|---|---|---|
| 25 | (structure) | (3aR,5S,6S,7R,7aR)-5-(difluoromethyl)-2-(methylamino)-5,6,7,7a-tetrahydro-3aH-pyrano[3,2-d]thiazole-6,7-diol |

¹H NMR (400 MHz, MeOD) δ 6.45 (d, J = 6.4 Hz, 1H), 6.01 (td, J = 54.2, 2.2 Hz, 1H), 4.23 (t, J = 6.0 Hz, 1H), 4.00 (t, J = 4.8 Hz, 1H), 3.82-3.73 (m, 2H), 2.95 (s, 3H). ¹³C NMR (100 MHz, MeOD) δ 168.82, 116.17 (t, $J_{C6,F}$ 241.5 Hz, C-6), 89.26, 75.42 (t, J = 21.2 Hz), 74.75, 69.87 (t, J = 3.3 Hz, C-4), 55.64, 32.20. (ES, m/z): [M + H]⁺: 255.0.

| Example | Structure | Name |
|---|---|---|
| 26 | (structure) | (3aR,5S,6S,7R,7aR)-5-(difluoromethyl)-2-(propylamino)-5,6,7,7a-tertahydro-3aH-pyrano[3,2-d]thiazole-6,7-diol |

¹H NMR (400 MHz, MeOD) δ 6.44 (d, J = 6.5 Hz, 1H), 6.01 (td, J = 54.2, 1.8 Hz, 1H), 4.23 (t, J = 5.9 Hz, 1H), 4.03 (t, J = 4.6 Hz, 1H), 3.79-3.72 (m, 2H), 3.32-3.23 (m, 2H), 1.69-1.60 (m, 2H), 0.98 (t, J = 7.3 Hz, 3H). ¹³C NMR (100 MHz, MeOD) δ 167.42, 116.25 (t, $J_{C6,F}$ 241.4 Hz, C-6), 89.12, 75.41 (t, J = 21.4 Hz), 74.78, 69.99 (t, J = 3.2 Hz, C-4), 55.64, 48.47, 23.98, 12.36. (ES, m/z): [M + H]⁺: 283.1.

Example 27

(3aR,5S,6S,7aR)-5-(difluoromethyl)-2-(methylamino)-5,6,7,7a-tetrahydro-3aH-pyrano[3,2-d]thiazol-6-ol

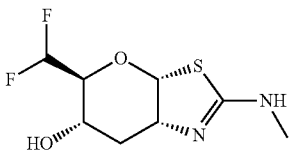

A mixture of ((3aR,5R,6S,7R,7aR)-6-(benzoyloxy)-2-(((tert-butoxycarbonyl)(methyl)amino)-7-hydroxy-5,6,7,7a-tetrahydro-3aH-pyrano[3,2-d]thiazol-5-yl)methyl benzoate (5.00 g, 9.24 mmol) and thio-CDI (90% tech, 3.40 g, 19.1 mmol) in anhydrous DMF (30 mL) was stirred at 95° C. for 4 h. After cooling the solvent was removed under reduced pressure, and the residue was purified on silica gel by flash column chromatography (EtOAc/hexanes, 1:10 to 2:3), affording -(3aR,5R,6S,7R,7aR)-7-((1H-imidazole-1-carbonothioyl)oxy)-5-((benzoyloxy)methyl)-2-((tert-butoxycarbonyl)(methyl)amino)-5,6,7,7a-tetrahydro-3aH-pyrano[3,2-d]thiazol-6-yl benzoate as a pale yellow solid (5.60 g, 93%). ¹H NMR (400 MHz, CDCl₃) δ 8.76 (s, 1H), 8.03-8.01 (m, 2H), 7.97-7.95 (m, 2H), 7.64-7.60 (m, 1H), 7.54-7.50 (m, 1H), 7.45 (t, J=7.7 Hz, 2H), 7.34 (t, J=7.7 Hz, 2H), 7.02 (s, 1H), 6.38-6.37 (m, 1H), 6.15 (d, J=7.1 Hz, 1H), 5.56 (td, J=1.2, 9.2 Hz, 1H), 4.70-4.67 (m, 1H), 4.58 (dd, J=3.2, 12.1 Hz, 1H), 4.42 (dd, J=5.1, 12.1 Hz, 1H), 4.08-4.03 (m, 1H), 3.43 (s, 3H), 1.56 (s, 9H).

A mixture of the above material (5.60 g, 8.59 mmol), Bu₃SnH (5.84 g, 17.0 mmol) and ABCN (0.15 g, 0.60 mmol) in mixed anhydrous toluene/THF (50/50 mL) was stirred at 90° C. for 16 h. After cooling the solvent was removed under reduced pressure, and the residue was purified on silica gel by flash column chromatography (EtOAc/hexanes, 1:10 to 1:2), affording (-(3aR,5R,6S,7aR)-6-(benzoyloxy)-2-((tert-butoxycarbonyl)(methyl)amino)-5,6,7,7a-tetrahydro-3aH-pyrano[3,2-d]thiazol-5-yl)methyl benzoate as a white solid (3.20 g, 70%). ¹H NMR (400 MHz, CDCl₃) δ 8.03-7.98 (m, 4H), 7.58-7.49 (m, 2H), 7.44-7.40 (m, 4H), 6.08 (d, J=7.3 Hz, 1H), 5.44-5.40 (m, 1H), 4.49-4.40 (m, 3H), 4.07-4.03 (m, 1H), 3.35 (s, 3H), 2.64-2.59 (m, 1H), 2.44-2.37 (m, 1H), 1.56 (s, 9H).

Following the procedure described for Example 32, the above material (3.20 g, 6.10 mmol) was benzoyl deprotected using K₂CO₃. After purification on silica gel by flash column chromatography (MeOH/DCM, 1:50 to 1:20), tert-butyl (-(3aR,5R,6S,7aR)-6-hydroxy-5-(hydroxymethyl)-5,6,7,7a-tetrahydro-3aH-pyrano[3,2-d]thiazol-2-yl)(methyl)carbamate was obtained as a white solid (1.82 g, 94%). ¹H NMR (400 MHz, CDCl₃) δ 5.91 (d, J=6.9 Hz, 1H), 4.36-4.32 (m, 1H), 3.89-3.85 (m, 1H), 3.81-3.75 (m, 1H), 3.65-3.59 (m, 1H), 3.38-3.34 (m, 1H), 3.33 (s, 3H), 2.48-2.43 (m, 1H), 2.32 (d, J=10.7 Hz, 1H), 2.17-2.11 (m, 1H), 1.84 (t, J=6.3 Hz, 1H), 1.54 (s, 9H).

Following the procedure described for Example 32, the above material (1.82 g, 5.74 mmol) was mono-TBDMS protected. After purification on silica gel by flash column chromatography (EtOAc/hexanes, 1:10 to 1:2), tert-butyl 43aR,5R,6S,7aR)-5-(((tert-butyldimethylsilyl)oxy)methyl)-6-hydroxy-5,6,7,7a-tetrahydro-3aH-pyrano[3,2-d]thiazol-2-yl)(methyl)carbamate was obtained as a colorless sticky oil (2.30 g, 93%). ¹H NMR (400 MHz, CDCl₃) δ 5.92 (d, J=6.8 Hz, 1H), 4.31-4.28 (m, 1H), 3.92-3.90 (m, 1H), 3.73 (d, J=4.6 Hz, 2H), 3.35-3.31 (m, 1H), 3.33 (s, 3H), 2.41 (d, J=9.4 Hz, 1H), 2.41-2.36 (m, 1H), 2.18-2.12 (m, 1H), 1.54 (s, 9H), 0.89 (s, 9H), 0.06 (s, 6H).

Following the procedure described for Example 32, the above material (2.78 g, 6.45 mmol) was benzyl protected using BnBr. After purification on silica gel by flash column chromatography (EtOAc/hexanes, 1:10 to 1:4), tert-butyl (-(3aR,5R,6S,7aR)-6-(benzyloxy)-5-(((tert-butyldimethylsilyl)oxy)methyl)-5,6,7,7a-tetrahydro-3aH-pyrano[3,2-d]thiazol-2-yl)(methyl)carbamate was obtained as a colorless sticky oil (2.7 g, 80%). $^1$H NMR (400 MHz, CDCl$_3$) δ 7.36-7.27 (m, 5H), 6.02 (d, J=7.1 Hz, 1H), 4.67 (d, J=11.6 Hz, 1H), 4.40 (d, J=11.6 Hz, 1H), 4.34-4.30 (m, 1H), 3.83-3.78 (m, 1H), 3.77-3.69 (m, 2H), 3.53-3.50 (m, 1H), 3.29 (s, 3H), 2.44-2.39 (m, 1H), 2.14-2.08 (m, 1H), 1.52 (s, 9H), 0.88 (s, 9H), 0.04 (s, 6H).

Following the procedure described for Example 32, the above material (2.70 g, 5.30 mmol) was silyl-deprotected using TBAF. After purification on silica gel by flash column chromatography (EtOAc/hexanes, 1:5 to 1:1), tert-butyl (-(3aR,5R,6S,7aR)-6-(benzyloxy)-5-(hydroxymethyl)-5,6,7,7a-tetrahydro-3aH-pyrano[3,2-d]thiazol-2-yl)(methyl)carbamate was obtained as a colorless sticky foam (2.0 g, 93%). $^1$H NMR (400 MHz, CDCl$_3$) δ 7.37-7.27 (m, 5H), 6.01 (d, J=7.2 Hz, 1H), 4.69 (d, J=11.6 Hz, 1H), 4.40 (d, J=11.6 Hz, 1H), 4.36-4.34 (m, 1H), 3.77-3.72 (m, 2H), 3.62-3.54 (m, 2H), 3.30 (s, 3H), 2.53-2.48 (m, 1H), 2.09-2.02 (m, 1H), 1.71 (t, J=6.3 Hz, 1H), 1.53 (s, 9H).

Following the procedure described for Example 32, the above material (0.663 g, 1.62 mmol) was oxidized to the aldehyde using DMP. After purification on silica gel by flash column chromatography (EtOAc/hexanes, 1:10 to 2:3), tert-butyl (-(3aR,5S,6S,7aR)-6-(benzyloxy)-5-formyl-5,6,7,7a-tetrahydro-3aH-pyrano[3,2-d]thiazol-2-yl)(methyl)carbamate was obtained as a white foam (0.57 g, 86%). $^1$H NMR (400 MHz, CDCl$_3$) δ 9.63 (s, 1H), 7.36-7.27 (m, 5H), 6.04 (d, J=4.3 Hz, 1H), 4.69 (d, J=9.2 Hz, 1H), 4.50 (d, J=9.2 Hz, 1H), 4.43-4.39 (m, 1H), 4.07 (d, J=6.4 Hz), 4.02-3.99 (m, 1H), 3.29 (s, 3H), 2.64-2.59 (m, 1H), 2.10-2.03 (m, 1H), 1.53 (s, 9H).

Following the procedure described for Example 32, the above material (0.550 g, 1.35 mmol) was treated with DAST. After purification on silica gel by flash column chromatography (EtOAc/hexanes, 1:10 to 1:3), tert-butyl (-(3aR,5S,6S,7aR)-6-(benzyloxy)-5-(difluoromethyl)-5,6,7,7a-tetrahydro-3aH-pyrano[3,2-d]thiazol-2-yl)(methyl)carbamate was obtained as a pale yellow sticky oil (0.48 g, 83%). $^1$H NMR (400 MHz, CDCl$_3$) δ 7.34-7.27 (m, 5H), 6.04 (d, J=7.4 Hz, 1H), 5.79 (dt, J=2.2, 54.7 Hz, 1H), 4.67 (d, J=11.4 Hz, 1H), 4.43 (d, J=11.4 Hz, 1H), 4.43-3.40 (m, 1H), 4.01-3.97 (m, 1H), 3.82-3.73 (m, 1H), 3.27 (s, 3H), 2.59-2.54 (m, 1H), 2.10-2.05 (m, 1H), 1.53 (s, 9H).

Following the procedure described for Example 32, the above material (0.480 g, 1.12 mmol was deprotected using BCl$_3$. After purification on silica gel by flash column chromatography (1.0 M NH$_3$ in MeOH/DCM, 1: 12), -(3aR,5S,6S,7aR)-5-(difluoromethyl)-2-(methylamino)-5,6,7,7a-tetrahydro-3aH-pyrano[3,2-d]thiazol-6-ol was obtained as a pale yellow sticky solid (0.24 g, 87%). $^1$H NMR (400 MHz, CD$_3$OD) δ 6.17 (d, J=6.4 Hz, 1H), 5.91 (dt, J=2.6, 54.4 Hz, 1H), 4.38-4.34 (m, 1H), 4.03-3.98 (m, 1H), 3.64-3.61 (m, 1H), 2.84 (s, 3H), 2.16-2.13 (m, 2H); $^{13}$C NMR (100 MHz, CD$_3$OD) δ 163.35, 116.00 (t, J=241.0 Hz), 91.12, 74.97 (t, J=42.7 Hz), 70.00, 64.54 (t, J=3.6 Hz), 34.19, 30.79; MS, m/z=239.0 (M+1).

Example 28

(3aR,5S,6S,7aR)-5-(difluoromethyl)-2-(dimethylamino)-5,6,7,7a-tetrahydro-3aH-pyrano[3,2-d]thiazol-6-ol

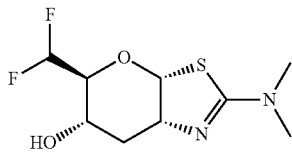 [SMILES: CN(C)C1=N[C@@H]2C[C@H](O)[C@@H](C(F)F)O[C@@H]2S1]

To a solution of -(3aR,5R,6R,7R,7aR)-7-((tert-butyldimethylsilyl)oxy)-5-(((tert-butyldimethylsilyl)oxy)methyl)-2-(dimethylamino)-5,6,7,7a-tetrahydro-3aH-pyrano[3,2-d]thiazol-6-ol (4.26 g, 8.95 mmol) in anhydrous DMF (30 mL) was added BnBr (1.68 g, 9.84 mmol) and tetrabutylammonium iodide (0.330 g, 0.895 mmol). At 0° C. NaH (60%, 0.430 g, 10.744 mmol) was added in portions and then the reaction was stirred at this temperature for 2 h. The mixture was diluted with water (200 mL), extracted with Et$_2$O (2×100 mL). The combined extract was washed with brine (100 mL) and dried over anhydrous Na$_2$SO$_4$. The solvent was evaporated under reduced pressure to give a mixture containing 80% -(3aR,5R,6R,7R,7aR)-6-(benzyloxy)-7-((tert-butyldimethylsilyl)oxy)-5-(((tert-butyldimethylsilyl)oxy)methyl)-N,N-dimethyl-5,6,7,7a-tetrahydro-3aH-pyrano[3,2-d]thiazol-2-amine (5.06 g, 100%) which was inseparable on silica gel column. This mixture was directly submitted to next reaction.

To a solution of the above material (9.89 g, 17.5 mmol) in MeOH (100 mL) at 0° C. was added AcCl (6.21 mL, 87.4 mmol). The mixture was stirred at room temperature for 16 h. Solvent was evaporated under reduced pressure. The residue was purified on silica gel column, eluted with 2%-5% 2M NH$_3$ MeOH solution in DCM to give -(3aR,5R,6S,7R,7aR)-6-(benzyloxy)-2-(dimethylamino)-5-(hydroxymethyl)-5,6,7,7a-tetrahydro-3aH-pyrano[3,2-d]thiazol-7-ol (4.58 g, 78%). MS m/z 339.1 (M+1, 100%).

To a solution of the above material (4.58 g, 13.6 mmol) and imidazole (2.76 g, 40.7 mmol) in anhydrous DMF (30 mL) at 0° C. was added TBDMSCl (2.45 g, 16.3 mmol). The mixture was stirred at room temperature for 21 h. The reaction was diluted with water (200 mL), extracted with Et$_2$O (2×100 mL). The combined extracts were washed with brine (100 mL) and dried over anhydrous Na$_2$SO$_4$. The solvent was evaporated under reduced pressure. The residue was purified on silica gel column, eluted with 1%-3% 2 M NH$_3$ MeOH solution in DCM to give -(3aR,5R,6S,7R,7aR)-6-(benzyloxy)-5-(((tert-butyldimethylsilyl)oxy)methyl)-2-(dimethylamino)-5,6,7,7a-tetrahydro-3aH-pyrano[3,2-d]thiazol-7-ol (5.80 g, 95%). MS m/z 453.2 (M+1, 100%); $^1$H NMR (400 MHz, CDCl$_3$) δ 7.27-7.37 (m, 5H), 6.37 (d, J=6.6 Hz, 1H), 4.88 (d, J=11.4 Hz, 1H), 4.63 (d, J=11.4 Hz, 1H), 4.22 (t, J=6.4 Hz, 1H), 4.09-4.13 (m, 1H), 3.80-3.82 (m, 2H), 3.74-3.78 (m, 1H), 3.64 (dd, J=8.7 Hz, 6.4 Hz, 1H), 2.98 (s, 6H), 0.897 (s, 9H), 0.90 (s, 9H), 0.052 (s, 3H), 0.056 (s, 3H).

A mixture of the above material (5.80 g, 12.8 mmol) and thio-CDI (90% tech, 4.57 g, 23.1 mmol) in anhydrous DMF (30 mL) was stirred at 90° C. for 2.5 h. After cooling, the mixture was diluted with water (200 mL), extracted with Et$_2$O (2×100 mL). The combined extracts were washed with brine (100 mL) and dried over anhydrous Na$_2$SO$_4$. The solvent was evaporated under reduced pressure. The residue was purified on silica gel column, eluted with 30%-100% EtOAc in hexanes to give 0-03aR,5R,6S,7R,7aR)-6-(benzyloxy)-5-(((tert-butyldimethylsilyl)oxy)methyl)-2-(dimethylamino)-5,6,7,7a-tetrahydro-3aH-pyrano[3,2-d]thiazol-7-yl) 1H-imidazole-1-carbothioate (6.51 g, 90%). MS m/z 563.2 (M+1, 100%); $^1$H NMR (400 MHz, CDCl$_3$) δ 8.30 (s, 1H), 7.59 (s, 1H), 7.23-7.34 (m, 5H), 7.03 (s, 1H), 6.36 (brs, 1H), 6.31 (d, J=6.7 Hz, 1H), 4.91 (d, J=11.6 Hz, 1H), 4.62 (m, 1H), 4.58 (d, J=11.6 Hz, 1H), 3.85 (d, J=8.7 Hz, 1H), 3.64-3.74 (m, 3H), 3.03 (s, 6H), 0.82 (s, 9H), 0.02 (s, 3H), 0.00 (s, 3H).

A mixture of the above material (6.51 g, 11.6 mmol), tributyltin hydride (7.47 g, 25.7 mmol) and ABCN (0.313 g, 1.28 mmol) in anhydrous THF (100 mL) was heated at reflux for 17 h. After cooling the solvent was evaporated under reduced pressure. The residue was purified by silica gel column chromatography, eluted with 50%-80% EtOAc in hexanes to give -(3aR,5R,6S,7aR)-6-(benzyloxy)-5-(((tert-butyldimethylsilyl)oxy)methyl)-N,N-dimethyl-5,6,7,7a-tetrahydro-3aH-pyrano[3,2-d]thiazol-2-amine as a white solid (4.07 g, 81%). MS m/z 437.2 (M+1, 100%); $^1$H NMR (400 MHz, CDCl$_3$) δ 7.24-7.37 (m, 5H), 6.25 (d, J=6.6 Hz, 1H), 4.71 (d, J=11.6 Hz, 1H), 4.42 (d, J=11.6 Hz, 1H), 4.34-4.39 (m, 1H), 3.65-3.80 (m, 4H), 2.99 (s, 6H), 2.25 (brs, 1H), 2.10-2.16 (m, 1H), 0.89 (s, 9H), 0.05 (s, 6H).

To a solution of the above material (4.07 g, 9.33 mmol) in MeOH (50 mL) at 0° C. was added AcCl (1.33 mL, 18.7 mmol). The mixture was stirred at room temperature for 16 h. Solvent was evaporated under reduced pressure. The residue was purified on silica gel column, eluted with 3%-5% 2 M NH$_3$ MeOH solution in DCM to give (-(3aR,5R,6S,7aR)-6-(benzyloxy)-2-(dimethylamino)-5,6,7,7a-tetrahydro-3aH-pyrano[3,2-d]thiazol-5-yl)methanol (2.78 g, 91%). MS m/z 323.1 (M+1, 100%); $^1$H NMR (400 MHz, CDCl$_3$) δ 7.25-7.36 (m, 5H), 6.22 (d, J=6.6 Hz, 1H), 4.70 (d, J=11.6 Hz, 1H), 4.42 (d, J=11.6 Hz, 1H), 4.32-4.37 (m, 1H), 3.71-3.79 (m, 2H), 3.60-3.67 (m, 2H), 2.97 (s, 6H), 2.19-2.25 (m, 1H), 2.09-2.15 (m, 1H), 1.86 (br s, 1H).

To a solution of DMSO (0.875 g, 11.2 mmol) in anhydrous DCM (15 mL) at –78° C. under N$_2$ was added oxalyl chloride (1.316 g, 10.36 mmol) dropwise. The mixture was stirred at ~–30° C. for 30 min and cooled to –78° C. again. A solution of the above material (1.39 g, 4.32 mmol) in anhydrous DCM (15 mL) was added dropwise. After stirred at ~–30° C. for 2 h the reaction mixture was cooled back to –78° C., and Et$_3$N (1.74 g, 17.3 mmol) was added. The mixture was stirred at ~–30° C. for another 30 min, and then quenched with water (50 mL). The organic layer was collected, and the aqueous was extracted with DCM (2×20 mL). The combined extracts were dried over anhydrous Na$_2$SO$_4$. The solvent was evaporated under reduced pressure to give the crude -(3aR,5S,6S,7aR)-6-(benzyloxy)-2-(dimethylamino)-5,6,7,7a-tetrahydro-3aH-pyrano[3,2-d]thiazole-5-carbaldehyde (1.24 g) as a yellow foam. MS m/z 353.1 (M+23, 100%).

To a solution of the above crude material (200 mg) in anhydrous DCM (5 mL) at 0° C. was added bis(2-methoxyethyl)aminosulfur trifluoride (0.553 g, 2.50 mmol). The mixture was stirred at room temperature for 27 h. The reaction was quenched with satd. aqueous NaHCO$_3$ (10 mL), and then extracted with EtOAc (2×10 mL). The combined extract was dried over anhydrous Na$_2$SO$_4$. The solvents were evaporated under reduced pressure, and the residue was purified by silica gel column chromatography (EtOAc/hexanes, 2:1 to 5:1) to afford -(3aR,5S,6R,7aR)-6-(benzyloxy)-5-(difluoromethyl)-N,N-dimethyl-5,6,7,7a-tetrahydro-3a1$^{-1}$-pyrano[3,2-d]thiazol-2-amine as a pale yellow foam (0.050 g, 23%, 2 steps). MS m/z 343.1 (M+1, 100%).

To a solution of the above material (0.049 g, 0.14 mmol) in DCM (2 mL) at –78° C. was added a solution of BCl$_3$ in DCM (1.0 M, 0.19 mL, 0.19 mmol). The mixture was slowly warmed up to room temperature and stirred for 18 h. The reaction was cooled to –78° C. again and a 1:1 mixture of MeOH-DCM (2 mL) was added dropwise to quench the reaction. Solvents were evaporated and the residue was treated with MeOH for three more times. The crude product was purified by silica gel column chromatography, eluted with 1%-2% 2 M NH$_3$ MeOH solution in DCM to give the product -(3aR,5S,6S,7aR)-5-(difluoromethyl)-2-(dimethylamino)-5,6,7,7a-tetrahydro-3aH-pyrano[3,2-d]thiazol-6-ol (0.0193 g, 53%) as a white solid. MS m/z 253.1 (M+1, 100%); $^1$H NMR (400 MHz, MeOD) δ 6.22 (d, J=6.5 Hz, 1H), 5.93 (td, J=54.4 Hz, 2.6 Hz, 1H), 4.36-4.40 (m, 1H), 3.99-4.03 (m, 1H), 3.59-3.68 (m, 1H), 3.03 (s, 6H), 2.12-2.16 (m, 2H); $^{13}$C NMR (100 MHz, MeOD) δ 165.06, 115.86 (t, J=192.8 Hz), 91.48, 74.91 (t, J=17.1 Hz), 70.02, 64.40 (t, J=2.8 Hz), 40.31, 34.09.

Example 29

(3aR,5S,6R,7R,7aR)-5-(difluoromethyl)-2-(ethylamino)-5,6,7,7a-tetrahydro-3aH-pyrano[3,2-d]thiazole-6,7-diol

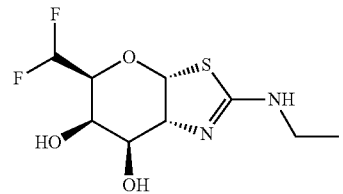 [SMILES: CCNC1=N[C@@H]2[C@@H](O)[C@@H](O)[C@@H](C(F)F)O[C@@H]2S1]

A solution of tert-butyl (-(3aR,5S,6S,7R,7aR)-5-(difluoromethyl)-6,7-dihydroxy-5,6,7,7a-tetrahydro-3aH-pyrano[3,2-d]thiazol-2-yl)(ethyl)carbamate (500 mg, 1.3 mmol) and imidazole (277 mg, 4 mmol) in DMF (20 mL) was treated with TBDMSCl (611 mg, 4 mmol) for 3 h at 40° C. The resulting solution was then cooled to room temperature, quenched by satd. aqueous NaHCO$_3$ (50 mL) solution, extracted with DCM (3×20 mL), washed with brine (3×10 mL), dried over anhydrous MgSO$_4$, and concentrated under vacuum to give a residue, which was purified by a silica gel column, eluted with 5%10% EtOAc in petroleum ether to afford tert-butyl(3 aR,5S,6R,7R,7aR)-7-(tert-butyldimethylsilyloxy)-5-(difluoromethyl)-6-hydroxy-5,6,7,7a-tetrahydro-3aH-pyrano[3,2-d]thiazol-2-yl(ethyl)carbamate as a light yellow syrup (420 mg, 64%). (ES, m/z): [M+1]$^+$ 483.0; $^1$H NMR (300 MHz, CDCl$_3$) δ 5.87 (d, J=5.4 Hz, 1H), 5.98 (td, J=55.2 Hz, 3.6 Hz, 1H), 4.10-3.91 (m, 5H), 3.77-3.70 (m, 1H), 1.56 (s, 9H), 1.21 (t, J=6.9 Hz, 3H), 0.94 (s, 9H), 0.19 (s, 3H), 0.15 (s, 3H).

A solution of the above material (440 mg, 0.9 mmol) in DCM (20 mL) was treated with DMP (587 mg, 1.4 mmol) for 1 h at room temperature. The reaction mixture was quenched by a mixture of satd. aqueous NaHCO$_3$ (5 mL) and sodium hyposulfite (5 mL). The organic layer was collected and the aqueous layer was extracted with DCM (3×20 ml). The combined organic layer was washed with brine (10 mL) and dried over anhydrous MgSO$_4$. After filtration, the filtrates were concentrated to give a residue, which was purified by a silica gel column, eluted with 5% EtOAc in petroleum ether to afford tert-butyl(3aR,5S,7R,7aR)-7-(tert-butyldimethylsilyloxy)-5-(difluoromethyl)-6-oxo-5,6,7,7a-tetrahydro-3aH-pyrano[3,2-d]thiazol-2-yl(ethyl)carbamate as white syrup (370 mg, 84%). (ES, m/z): [M+1]+ 481.0; $^1$H NMR (300 MHz, CDCl$_3$) δ 6.20 (d, J=6.9 Hz, 1H), 6.08 (td, J=52.8 Hz, 1.5 Hz, 1H), 4.69 (d, J=3.6 Hz, 1H), 4.63 (dd, J=6.9 Hz, 3.9 Hz, 1H), 4.16-4.09 (m, 1H), 3.98-3.89 (m, 2H), 1.57 (s, 9H), 1.14 (t, J=6.9 Hz, 3H), 0.93 (s, 9H), 0.20 (s, 3H), 0.13 (s, 3H).

A solution of the above material (400 mg, 0.8 mmol) in MeOH (5 mL) was treated with NaBH$_4$ (63 mg, 1.7 mmol) for 2 h at room temperature. The reaction mixture was quenched with water (20 mL) and extracted with DCM (3×10 mL). The combined organic layer was washed with brine (10 mL), dried over anhydrous MgSO$_4$, and concentrated under vacuum to give a residue, which was purified by a silica gel column, eluted with 10% EtOAc in petroleum ether to afford tert-butyl-(3aR,5S,6S,7R,7aR)-7-(tert-butyldimethylsilyloxy)-5-(difluoromethyl)-6-hydroxy-5,6,7,7a-tetrahydro-3aH-pyrano[3,2-d]thiazol-2-yl(ethyl)carbamate as white syrup (103 mg, 25%). (ES, m/z): [M+1]+ 483.0; $^1$H NMR (300 MHz, CDCl$_3$) δ 6.04 (d, J=6.3 Hz, 1H), 6.06 (td, J=70.2 Hz, 6.6 Hz, 1H), 4.37-4.31 (m, 1H), 4.25-4.20 (m, 1H), 4.12-4.06 (m, 1H), 4.01-3.92 (m, 2H), 3.87 (m, 1H), 3.85-3.76 (m, 1H), 1.56 (s, 9H), 1.21 (t, J=6.9 Hz, 3H), 0.96 (s, 9H), 0.22 (s, 3H), 0.18 (s, 3H).

To a solution of the above material (20 mg, 0.04 mmol) in MeOH (10 mL) was bubbled with dry HCl gas until it was saturated at 0° C. The resulting solution was stirred for 3 h at room temperature. Removal of volatiles gave a residue, which was dissolved into MeOH (2 mL) and neutralized with concentrated NH$_4$OH (1 mL). After concentrating under reduced pressure, the crude product was purified by a short silica gel column, eluted with 10% MeOH in DCM to afford -(3aR,5S,6R,7R,7aR)-5-(difluoromethyl)-2-(ethylamino)-5,6,7,7a-tetrahydro-3aH-pyrano[3,2-d]thiazole-6,7-diol as a white solid (10 mg, 90%). (ES, m/z): [M+1]+ 269.0; $^1$H NMR (300 MHz, CD$_3$OD) δ 6.31 (d, J=6.0 Hz, 1H), 5.97 (td, J=56.1, 6.3 Hz, 1H), 4.12 (t, J=6.3 Hz, 1H), 4.03 (t, J=3.0 Hz, 1H), 3.95-3.90 (m, 1H), 3.88-3.85 (m, 1H), 3.32-3.21 (m, 2H), 1.17 (t, J=7.5 Hz, 3H).

Example 30

(3aR,5R,6S,7R,7aR)-7-fluoro-5-(hydroxymethyl)-2-(methylamino)-5,6,7,7a-tetrahydro-3aH-pyrano[3,2-d]thiazol-6-ol

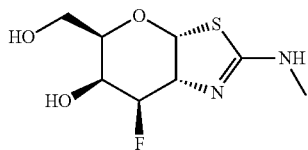

To a solution of tert-butyl (-(3aR,5R,7R,7aR)-5-(((tert-butyldimethylsilypoxy)methyl)-7-fluoro-6-oxo-5,6,7,7a-tetrahydro-3aH-pyrano[3,2-d]thiazol-2-yl)(methyl)carbamate (2.57 g, 5.72 mmol) in dry MeOH (50 mL), at 0° C., was added NaBH$_4$ (0.295 g, 7.80 mmol). After the mixture was stirred at 0° C. for 20 min a chip of dry ice was added, and the solvent was evaporated. The residue was dissolved in DCM (50 mL) and washed with satd. aqueous NaHCO$_3$ (50 mL). The organic layer was collected, and the aqueous was extracted with DCM (2×30 mL). The combined extract was dried over anhydrous Na$_2$SO$_4$. After filtration the solvent was evaporated under reduced pressure, and the residue was purified on silica gel by flash column chromatography (EtOAc/hexanes, 1:10 to 1:3), affording tert-butyl 43aR,5R,6S,7R,7aR)-5-(((tert-butyldimethylsilypoxy)methyl)-7-fluoro-6-hydroxy-5,6,7,7a-tetrahydro-3aH-pyrano[3,2-d]thiazol-2-yl)(methypcarbamate (0.95 g, 37%), as a sticky oil. $^1$H NMR (400 MHz, CDCl$_3$) δ 6.11 (d, J=6.7 Hz, 1H), 4.84 (ddd, J=3.2, 6.7, 48.2 Hz, 1H), 4.45 (td, J=6.7, 16.6 Hz, 1H), 4.32-4.29 (m, 1H), 4.00-3.93 (m, 2H), 3.90-3.86 (m, 1H), 3.36 (s, 3H), 3.19 (s, br., 1H, (OH)), 1.53 (s, 9H), 0.90 (s, 9H), 0.093 (s, 3H), 0.087 (s, 3H).

To a solution of the above material (0.110 g, 0.244 mmol) in dry MeOH (4 mL) was bubbled HCl gas for 30 sec. The mixture was stirred at room temperature for 2 h. After the solvent was evaporated under reduced pressure, the residue was neutralized with 1.0 M NH$_3$ in MeOH and purified on silica gel by flash column chromatography (1.0 M NH$_3$ in MeOH/DCM, 1:9) affording -(3aR,5R,6S,7R,7aR)-7-fluoro-5-(hydroxymethyl)-2-(methylamino)-5,6,7,7a-tetrahydro-3aH-pyrano[3,2-d]thiazol-6-ol as a white solid (0.043 g, 89%). $^1$H NMR (400 MHz, CD$_3$OD) δ 6.38 (dd, J=1.0, 6.7 Hz, 1H), 4.65 (ddd, J=3.3, 7.8, 48.2 Hz, 1H), 4.30-4.22 (m, 1H), 4.15-4.11 (m, 1H), 4.01-3.98 (m, 1H), 3.78-3.72 (m, 2H), 2.83 (s, 3H); $^{13}$C NMR (100 MHz, CD$_3$OD) δ 164.87, 94.77 (d, J=182.5 Hz), 91.73 (d, J=7.8 Hz), 75.66 (d, J=5.8 Hz), 69.89 (d, J=21.0 Hz), 67.01 (d, J=27.6 Hz), 61.81 (d, J=3.1 Hz), 30.30; MS, (ES, m/z) [M+H]+ 237.1.

Example 31

(3aR,5S,6R,7R,7aR)-7-fluoro-5-(fluoromethyl)-2-(methylamino)-5,6,7,7a-tetrahydro-3aH-pyrano[3,2-d]thiazol-6-ol

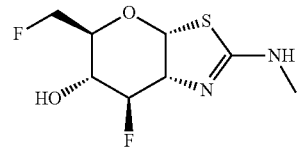

To a suspension of -(3aR,5R,6S,7R,7aR)-5-(hydroxymethyl)-2-(methylamino)-5,6,7,7a-tetrahydro-3aH-pyrano[3,2-d]thiazole-6,7-diol (80.00 g, 341.6 mmol) in DMF (500 mL) was added DIPEA (8 mL), MeOH (8 mL) and Boc$_2$O (100.0 g, 458.7 mmol) in sequence. The suspension was stirred at room temperature for 6 h, and became a clear solution. After the volume of the solution was reduced under reduced pressure at room temperature by around 100 mL to remove MeOH and tert-butanol, the solution was cooled with an ice cooling bath, and imidazole (92.9 g, 1.36 mol), and TBDMSCl (155 g, 1.03 mol) was added in sequence. After stirred at room temperature overnight the mixture was diluted with brine (1.5 L). Extraction was performed with Et$_2$O three times (500 mL and 2×300 mL). The combined ether extract was washed with brine (1 L) and dried over anhydrous Na$_2$SO$_4$. After filtration the solvent was evaporated under reduced pressure, and the residue of the two batches was combined and purified on silica gel by flash column chromatography (EtOAc/hexanes, 2:11) to afford tert-butyl ((3aR,5R,6R,7R,7aR)-7-((tert-butyldimethylsilypoxy)-5-(((tert-butyldimethylsilypoxy)methyl)-6-hydroxy-5,6,7,7a-tetrahydro-3aH-pyrano[3,2-d]thiazol-2-yl)(methyl) carbamate as a white crystalline solid (136 g, 71%). $^1$H NMR (500 MHz, CDCl$_3$) δ 6.15 (d, J=6.2 Hz, 1H), 4.29 (s, br. 1H), 4.06-4.05 (m, 1H), 3.81-3.75 (m, 2H), 3.71-3.68 (m, 1H), 3.47-3.43 (m, 1H), 3.36 (s, 3H), 1.54 (s, 9H), 0.915 (s, 9H), 0.893 (s, 9H), 0.161 (s, 3H), 0.149 (s, 3H), 0.068 (s, 6H).

At 0° C., to a solution of the above material (94.30 g, 167.5 mmol) and DMAP (0.50 g, 4.1 mmol) in pyridine (350 mL) was added BzCl (28.3 g, 201 mmol). The mixture was stirred at room temperature overnight, another portion of BzCl (6.90 g, 49.1 mmol) was added and the mixture was stirred at room temperature for another 3 h. MeOH (20 ml) was added and the mixture was stirred for another 30 min. The mixture was diluted with brine (1 L) and extracted with mixed EtOAc/hexanes three times (1:4; 600 mL, 200 mL and 100 mL). The combined extract was dried over anhydrous $Na_2SO_4$. After filtration the solvent was evaporated under reduced pressure, and the combined residue of all three batches was treated with 1.5 M HCl in MeOH (1.0 L) at room temperature for 16 h. The solvent was then removed at room temperature under reduced pressure to afford a white solid. To the white solid in DCM (1.6 h) was added DIPEA (100 mL) and $Boc_2O$ (109 g, 500 mmol) in sequence. The mixture was then stirred at room temperature for 4 days. The reaction mixture was washed with satd. aqueous $NH_4Cl$ (1 L) and brine (1 L), and dried over anhydrous $Na_2SO_4$. (The combined aqueous washing was basified to pH=9 with satd. aqueous $Na_2CO_3$ solution and extracted with DCM (5×150 mL). The combined DCM extracts were dried over anhydrous $Na_2SO_4$. After filtration the solution was treated with $Boc_2O$ (30 g) for 5 h. After washed with satd. aqueous $NH_4Cl$ (1 L) and brine (1 L), and dried over anhydrous $Na_2SO_4$). All DCM extracts were combined. After filtration the solvent was evaporated under reduced pressure, and the residue was purified on silica gel by flash column chromatography (EtOAc/hexanes, 1:4 to 3:2) to afford -(3aR,5R,6S,7R,7aR)-2-((tert-butoxycarbonyl)(methyl)amino)-7-hydroxy-5-(hydroxymethyl)-5,6,7,7a-tetrahydro-3aH-pyrano[3,2-d]thiazol-6-yl benzoate as a white solid (56.5 g, 77%). $^1$H NMR (400 MHz, $CDCl_3$) δ 8.00-7.98 (m, 2H), 7.59-7.54 (m, 1H), 7.44-7.40 (m, 2H), 6.20 (d, J=7.0 Hz, 1H), 5.15-5.12 (m, 1H), 4.55-4.50 (m, 1H), 4.41-4.39 (m, 1H), 3.80-3.76 (m, 1H), 3.70-3.66 (m, 1H), 3.49 (s, br., 1H), 3.34 (s, 3H), 1.56 (s, 9H).

To a solution of the above material (500 mg, 1.1 mmol) in DCM (15 mL) was added DAST (1.1 g, 6.8 mmol) at −78° C. under nitrogen atmosphere. After stirred overnight at room temperature, the reaction mixture was quenched with satd. aqueous $NaHCO_3$ (30 mL) solution, extracted with DCM (3×15 mL), dried over anhydrous $Na_2SO_4$, and condensed to give a residue, which was purified by a silica gel column, eluted with 10%-30% EtOAc in petroleum ether to afford -(3aR,5S,6R,7R,7aR)-2-(tert-butoxycarbonyl(methyl)amino)-7-fluoro-5-(fluoromethyl)-5,6,7,7a-tetrahydro-3aH-pyrano[3,2-d]thiazol-6-yl benzoate (370 mg, 73%) as light yellow oil. (ES, m/z): $[M+H]^+$ 443.0; $^1$H NMR (300 MHz, $CDCl_3$) δ 8.02-8.01 (m, 2H), 7.64-7.62 (m, 1H), 7.59-7.44 (m, 2H), 6.19 (d, J=7.2 Hz, 1H), 5.44-5.26 (m, 2H), 4.62-4.60 (m, 2H), 4.58-4.46 (m, 1H), 3.90-3.80 (m, 1H), 3.39 (s, 3H), 1.58 (s, 9H).

A solution of the above material (170 mg, 0.4 mmol) in THF (10 mL) was treated with MeMgCl (3 mmol, 1 ml, 3 M in THF) for 1 h at room temperature. The reaction mixture was quenched with satd. aqueous $NH_4Cl$ (30 mL) solution, extracted with EtOAc (3×20 mL), washed with brine (10 mL), dried over anhydrous $Na_2SO_4$, and condensed to give a residue, which was purified by a silica gel column, eluted with 2%-5% MeOH in DCM to afford -(3aR,5S,6R,7R,7aR)-7-fluoro-5-(fluoromethyl)-2-(methylamino)-5,6,7,7a-tetrahydro-aH-pyrano[3,2-d]thiazol-6-ol as a white solid (35 mg, 38%). (ES, m/z): $[M+H]^+$ 239.0; $^1$H NMR (300 MHz, $CDCl_3$) δ 6.27 (d, J=6.3 Hz, 1H), 5.14 (td, J=45.6 Hz, 2.1 Hz, 1H), 4.70-4.44 (m, 3H), 3.90-3.79 (m, 1H), 3.73-3.61 (m, 1H), 2.95 (s, 3H).

Example 32

(3aR,5S,6R,7R,7aR)-5-(difluoromethyl)-7-fluoro-2-(methylamino)-5,6,7,7a-tetrahydro-3aH-pyrano[3,2-c]ithiazol-6-ol

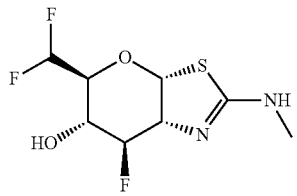

To a suspension of -(3aR,5R,6S,7R,7aR)-2-(methylamino)-5-(hydroxymethyl)-5,6,7,7a-tetrahydro-3aH-pyrano[3,2-d]thiazole-6,7-diol (8.50 g, 37.0 mmol) in DMF (60 mL) was added DIPEA (2.0 mL), $Boc_2O$ (23.0 g, 105 mmol) and MeOH (2.0 mL). The mixture was stirred at room temperature for 3 h, and then MeOH (50 mL) was added. The reaction mixture was concentrated under reduced pressure at −35° C. The residue was purified on silica gel by flash column chromatography (MeOH/DCM, 1:8), followed by recrystallization from EtOAc/hexanes, to afford tert-butyl (-(3aR,5R,6S,7R,7aR)-6,7-dihydroxy-5-(hydroxymethyl)-5,6,7,7a-tetrahydro-3aH-pyrano[3,2-d]thiazol-2-yl)(methypcarbamate as a white solid (11.8 g, 96%). $^1$H NMR (400 MHz, $CDCl_3$) δ 6.14 (d, J=6.9 Hz, 1H), 4.20 (d, J=6.4 Hz, 1H), 4.11 (d, J=5.6 Hz, 1H), 3.85-3.70 (m, 2H), 3.63-3.55 (m, 1H), 3.31 (s, 3H), 1.53 (s, 9H).

To a solution of the above material (11.7 g, 35.1 mmol), DIPEA (10.3 g, 80.0 mmol) and DMAP (0.040 g, 0.33 mmol) in DCM (180 mL), at 0° C., was added BzCl (10.1 g, 72.0 mmol) slowly. After addition the mixture was stirred at room temperature for 5 h. Satd. aqueous $NH_4Cl$ solution (100 mL) was added, and the organic layer was collected. The aqueous layer was further extracted with DCM (3×50 mL). The combined extract was dried over anhydrous $Na_2SO_4$. After filtration the solvent was evaporated under reduced pressure, and the residue was separated on silica gel by flash column chromatography (EtOAc/hexanes, 1:4 to 1:1), affording (-(3aR,5R,6S,7R,7aR)-6-(benzoyloxy)-2-((tert-butoxycarbonyl)(methyl)amino)-7-hydroxy-5,6,7,7a-tetrahydro-3aH-pyrano[3,2-d]thiazol-5-yl)methyl benzoate as a white solid (4.20 g, 22%). $^1$H NMR (400 MHz, $CDCl_3$) δ 8.01-7.99 (m, 4H), 7.60-7.55 (m, 1H), 7.54-7.50 (m, 1H), 7.45-7.41 (m, 2H), 7.37-7.35 (m, 2H), 6.21 (d, J=7.1 Hz, 1H), 5.23-5.20 (m, 1H), 4.55-4.51 (m, 2H), 4.48-4.42 (m, 2H), 4.15-4.07 (m, 2H), 3.36 (s, 3H), 1.56 (s, 9H).

To a solution of the above material (7.91 g, 14.6 mmol) in anhydrous DCM (100 mL) at −78° C. under $N_2$, was added DAST (11.8 g, 73.0 mmol). After addition the mixture was stirred at room temperature for 72 h. The reaction mixture was then cooled at −78° C., diluted with DCM (100 mL), and then quenched with satd. aqueous $NaHCO_3$ (150 mL). The organic layer was collected, and the aqueous was extracted with DCM (2×100 mL). The combined extract was dried over anhydrous $Na_2SO_4$. After filtration the solvent was evaporated under reduced pressure, and the residue was purified on silica gel by flash column chromatography (EtOAc/hexanes, 1:10 to 1:4), affording (-(3aR,5R,6R,7R,7aR)-6-(benzoyloxy)-2-((tert-butoxycarbonyl)(methyl)amino)-7-fluoro-5,6,7,7a-tetrahydro-3aH-pyrano[3,2-d]thiazol-5-yOmethyl benzoate as a white solid (6.10 g, 77%). $^1$H NMR (400 MHz, CDCl$_3$) δ 8.01-7.98 (m, 4H), 7.60-7.56 (m, 1H), 7.56-7.52 (m, 1H), 7.45-7.41 (m, 2H), 7.38-7.35 (m, 2H), 6.19 (d, J=7.2 Hz, 1H), 5.52-5.46 (m, 1H), 5.40-5.28 (m, 1H), 4.61-4.56 (m, 1H), 4.52 (dd, J=3.6, 12.0 Hz, 1H), 4.43 (dd, J=5.7, 12.0 Hz, 1H), 4.03-3.99 (m, 1H), 3.36 (s, 3H), 1.56 (s, 9H).

A mixture of the above material (6.10 g, 11.2 mmol) and K$_2$CO$_3$ (1.00 g, 7.25 mmol) in anhydrous MeOH (50 mL) was stirred at room temperature for 3 h. Dry ice was added, and the solvent was removed under reduced pressure. The residue was purified on silica gel by flash column chromatography (EtOAc/hexanes, 1:1 to 10:1), affording tert-butyl (-(3aR,5R, 6R,7R,7aR)-7-fluoro-6-hydroxy-5-(hydroxymethyl)-5,6,7, 7a-tetrahydro-3aH-pyrano[3,2-d]thiazol-2-yl)(methyl)carbamate as a white solid (3.25 g, 86%). $^1$H NMR (400 MHz, CDCl$_3$) δ 6.06 (d, J=6.8 Hz, 1H), 5.15 (ddd, J=2.4, 4.4, 45.7 Hz, 1H), 4.46-4.41 (m, 1H), 3.96-3.89 (m, 1H), 3.83 (dd, J=3.2, 11.8 Hz, 1H), 3.73 (dd, J=5.4, 11.8 Hz, 1H), 3.46-3.42 (m, 1H), 3.32 (s, 3H), 1.54 (s, 9H).

At 0° C., to a solution of the above material (0.880 g, 2.61 mmol) and imidazole (0.354 g, 5.20 mmol) in anhydrous DMF (15 mL) was added TBDMSCl (0.452 g, 3.00 mmol). The mixture was stirred at room temperature for 72 h and diluted with Et$_2$O (100 mL) and brine (100 mL). The organic layer was collected, and the aqueous was extracted with Et$_2$O (50 mL). The combined extract was washed with water (50 mL) and dried over anhydrous Na$_2$SO$_4$. After filtration the solvent was evaporated under reduced pressure, and the residue was purified on silica gel by flash column chromatography (EtOAc/hexanes, 1:10 to 1:3), affording tert-butyl (-(3aR,5R,6R,7R,7aR)-5-(((tert-butyldimethylsilyl)oxy)methyl)-7-fluoro-6-hydroxy-5,6,7,7a-tetrahydro-3aH-pyrano[3,2-d]thiazol-2-yl)(methyl)carbamate as a white foam (1.10 g, 93%). $^1$H NMR (400 MHz, CDCl$_3$) δ 6.06 (d, J=6.8 Hz, 1H), 5.19-5.02 (m, 1H), 4.43-4.38 (m, 1H), 3.98-3.93 (m, 1H), 3.85 (dd, J=5.0, 10.6 Hz, 1H), 3.73 (dd, J=5.2, 10.6 Hz, 1H), 3.45-3.43 (m, 1H), 3.34 (s, 3H), 1.54 (s, 9H), 0.89 (s, 9H), 0.08 (s, 6H).

At 0° C., to a solution of the above material (1.06 g, 2.35 mmol) and Bu$_4$NI (0.087 g, 0.24 mmol) in anhydrous DMF (15 mL) was added NaH (60% in mineral oil, 0.118 g, 2.94 mmol). After addition of NaH, to the reaction mixture was added BnBr (0.703 g, 4.11 mmol). The mixture was stirred at room temperature for 16 h and diluted with Et$_2$O (60 mL) and satd. NH$_4$Cl (50 mL). The organic layer was collected, and the aqueous was extracted with Et$_2$O (2×30 mL). The combined extract was washed with brine (40 mL) and dried over anhydrous Na$_2$SO$_4$. After filtration the solvent was evaporated under reduced pressure, and the residue was purified on silica gel by flash column chromatography (EtOAc/hexanes, 1:10 to 1:4), affording tert-butyl 43aR,5R,6R,7R,7aR)-6-(benzyloxy)-5-(((tert-butyldimethylsilypoxy)methyl)-7-fluoro-5,6,7,7a-tetrahydro-3aH-pyrano[3,2-d]thiazol-2-yl) (methypcarbamate as a sticky oil (1.22 g, 96%). $^1$H NMR (400 MHz, CDCl$_3$) δ 7.37-7.27 (m, 5H), 6.10 (d, J=7.0 Hz, 1H), 5.30-5.16 (m, 1H), 4.80 (d, J=11.0 Hz, 1H), 4.55 (d, J=11.0 Hz, 1H), 4.48-4.42 (m, 1H), 3.88-3.80 (m, 1H), 3.78-3.69 (m, 2H), 3.46-3.44 (m, 1H), 3.31 (s, 3H), 1.53 (s, 9H), 0.89 (s, 9H), 0.04 (s, 6H).

At 0° C., to a solution of the above material (1.22 g, 2.25 mmol) in THF (15 mL) was added TBAF (1.0 M in THF, 5.0 mL, 5.0 mmol). After addition the reaction mixture was stirred at room temperature for 2 h and diluted with EtOAc (20 mL) and brine (50 mL). The organic layer was collected, and the aqueous was extracted with EtOAc (2×50 mL). The combined extract was dried over anhydrous Na$_2$SO$_4$. After filtration the solvent was evaporated under reduced pressure, and the residue was purified on silica gel by flash column chromatography (EtOAc/hexanes, 1:5 to 1:2), affording tert-butyl (-(3aR,5R,6R,7R,7aR)-6-(benzyloxy)-7-fluoro-5-(hydroxymethyl)-5,6,7,7a-tetrahydro-3aH-pyrano[3,2-d]thiazol-2-yl)(methyl)carbamate as a white solid (0.96 g, 100%). $^1$H NMR (400 MHz, CDCl$_3$) δ 7.37-7.29 (m, 5H), 6.09 (d, J=6.7 Hz, 1H), 5.32 (ddd, J=1.8, 3.6, 45.4 Hz, 1H), 4.80 (d, J=11.6 Hz, 1H), 4.55 (d, J=11.6 Hz, 1H), 4.53-4.48 (m, 1H), 3.81-3.72 (m, 2H), 3.61-3.55 (m, 1H), 3.49-3.45 (m, 1H), 3.31 (s, 3H), 1.53 (s, 9H).

To a solution of the above material (L50 g, 3.52 mmol) in DCM (40 mL) was added DMP (2.20 g, 5.20 mmol). After stirred at room temperature for 1 h the reaction mixture was diluted with Et$_2$O (20 mL), and then concentrated to dryness. Satd. aqueous NaHCO$_3$ (30 mL) with Na$_2$S$_2$O$_3$ (2 g) was added, and the mixture was extracted with EtOAc (2×50 mL). The combined extract was dried over anhydrous Na$_2$SO$_4$. After filtration the solvent was evaporated under reduced pressure, and the residue was purified on silica gel by flash column chromatography (EtOAc/hexanes, 1:5 to 1:2), affording tert-butyl (-(3aR,5S,6R,7R,7aR)-6-(benzyloxy)-7-fluoro-5-formyl-5,6,7,7a-tetrahydro-3aH-pyrano[3,2-d]thiazol-2-yl)(methyl)carbamate as a white solid (1.02 g, 68%). $^1$H NMR (400 MHz, CDCl$_3$) δ 9.60 (s, 1H), 7.35-7.29 (m, 5H), 6.12 (d, J=7.0 Hz, 1H), 5.39-5.27 (m, 1H), 4.78 (d, J=11.4 Hz, 1H), 4.66 (d, J=11.4 Hz, 1H), 4.57-4.51 (m, 1H), 4.00-3.95 (m, 2H), 3.31 (s, 3H), 1.53 (s, 9H).

To a solution of the above material (0.156 g, 0.367 mmol) in anhydrous DCM (6 mL) at −78° C. under N$_2$, was added DAST (0.354 g, 2.20 mmol). After addition the mixture was stirred at room temperature for 16 h. The reaction mixture was then cooled at −78° C., diluted with DCM (10 mL), and then quenched with satd. aqueous NaHCO$_3$ (10 mL). The organic layer was collected, and the aqueous was extracted with DCM (2×15 mL). The combined extract was dried over anhydrous Na$_2$SO$_4$. After filtration the solvent was evaporated under reduced pressure, and the residue was purified on silica gel by flash column chromatography (EtOAc/hexanes, 1:10 to 1:4), affording tert-butyl (-(3aR,5S,6R,7R,7aR)-6-(benzyloxy)-5-(difluoromethyl)-7-fluoro-5,6,7,7a-tetrahydro-3aH-pyrano [3,2-d]thiazol-2-yl)(methyl)carbamate as a pale yellow oil (0.125 g, 76%). $^1$H NMR (400 MHz, CDCl$_3$) δ 7.38-7.29 (m, 5H), 6.11 (d, J=7.2 Hz, 1H), 5.79 (dt, J=2.4, 54.4 Hz, 1H), 5.37-5.25 (m, 1H), 4.78 (d, J=11.3 Hz, 1H), 4.59 (d, J=11.3 Hz, 1H), 4.58-4.53 (m, 1H), 4.00-3.92 (m, 1H), 3.72-3.63 (m, 1H), 3.29 (s, 3H), 1.53 (s, 9H).

To a solution of the above material (0.240 g, 0.537 mmol) and pentamethylbenzene (0.26 g, 1.7 mmol) in anhydrous DCM (10 mL) at −78° C. under N$_2$, was added BCl$_3$ (1.0 M in DCM, 1.6 mL, 1.6 mmol). The mixture was stirred at room temperature for 3 h while the temperature of the cooling trap reached at 0° C. The reaction mixture was cooled at −78° C., quenched with mixed MeOH/DCM, and then concentrated to dryness. The residue was purified on silica gel by flash column chromatography (1.0 M NH$_3$ in MeOH/DCM, 1: 15), affording -(3aR,5S,6R,7R,7aR)-5-(difluoromethyl)-7-fluoro-2-(methylamino)-5,6,7,7a-tetrahydro-3aH-pyrano[3, 2-d]thiazol-6-ol as an off-white solid (0.104 g, 76%). NMR (400 MHz, CD$_3$OD) δ 6.30 (d, J=6.6 Hz, 1H), 5.96 (dt, J=2.4, 54.1 Hz, 1H), 4.89 (td, J=3.9, 46.5 Hz, 1H), 4.48-4.42 (m, 1H), 4.02-3.94 (m, 1H), 3.72-3.63 (m, 1H), 2.85 (s, 3H); $^{13}$C NMR (100 MHz, CD$_3$OD) δ 164.08 (d, J=2.3 Hz), 115.63 (dt, J=7.9, 241.6 Hz), 94.73 (d, J=177.6 Hz), 89.90 (d, J=2.0 Hz),

Example 33

(3aR,5S,6R,7S,7aR)-5-(difluoromethyl)-7-fluoro-2-(methylamino)-5,6,7,7a-tetrahydro-3aH-pyrano[3,2-d]thiazol-6-ol

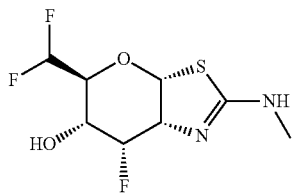

At 0° C., to a solution of tert-butyl (-(3aR,5R,6R,7R,7aR)-7-fluoro-6-hydroxy-5-(hydroxymethyl)-5,6,7,7a-tetrahydro-3aH-pyrano[3,2-d]thiazol-2-yl)(methyl)carbamate (18.7 g, 55.5 mmol) and imidazole (11.4 g, 167 mmol) in anhydrous DMF (150 mL) was added TBDMSCl (9.19 g, 61.0 mmol). The mixture was stirred at room temperature for 16 h, diluted with Et$_2$O (300 mL) and washed with brine (2×300 mL). The organic layer was collected, and the aqueous was extracted with Et$_2$O (2×150 mL). The combined extract was washed with brine (100 mL) and dried over anhydrous Na$_2$SO$_4$. After filtration the solvent was evaporated under reduced pressure, and the residue was purified on silica gel by flash column chromatography (EtOAc/hexanes, 1:10 to 1:3), affording tert-butyl (-(3aR,5R,6R,7R,7aR)-5-(((tert-butyldimethylsilyl)oxy)methyl)-7-fluoro-6-hydroxy-5,6,7,7a-tetrahydro-3aH-pyrano[3,2-d]thiazol-2-yl)(methyl)carbamate as a white foam (24.1 g, 96%). $^1$H NMR (400 MHz, CDCl$_3$) δ 6.06 (d, J=6.8 Hz, 1H), 5.19-5.02 (m, 1H), 4.43-4.38 (m, 1H), 3.98-3.93 (m, 1H), 3.85 (dd, J=5.0, 10.6 Hz, 1H), 3.73 (dd, J=5.2, 10.6 Hz, 1H), 3.45-3.43 (m, 1H), 3.34 (s, 3H), 1.54 (s, 9H), 0.89 (s, 9H), 0.08 (s, 6H).

To a solution of the above material (9.28 g, 20.6 mmol) in DCM (150 mL) was added DMP (13.1 g, 30.9 mmol). After stirred at room temperature for 1 h the reaction was diluted with Et$_2$O (400 mL). The resulting suspension was filtered through Celite cake, and the filtrate was concentrated to dryness at room temperature. The residue was loaded onto a layered NaHCO$_3$/silica gel plug, and the product was eluted with (EtOAc/hexanes, 1:4), affording tert-butyl (-(3aR,5R,7R,7aR)-5-(((tert-butyldimethylsilyl)oxy)methyl)-7-fluoro-6-oxo-5,6,7,7a-tetrahydro-3aH-pyrano[3,2-d]thiazol-2-yl)(methyl)carbamate as a white crystalline solid (8.96 g, 97%). $^1$H NMR (400 MHz, CDCl$_3$) δ 6.29 (d, J=7.0 Hz, 1H), 5.09 (dd, J=4.7, 48.4 Hz, 1H), 4.75-4.69 (m, 1H), 4.12-4.05 (m, 2H), 3.96-3.93 (m, 1H), 3.28 (s, 3H), 1.54 (s, 9H), 0.86 (s, 9H), 0.056 (s, 3H), 0.050 (s, 3H).

To a solution of the above material (8.96 g, 20.0 mmol) in dry MeOH (250 mL) was added NaH (60% in mineral oil, 0.158 g, 3.95 mmol), and the mixture was stirred at room temperature for 15 min. The reaction mixture was then cooled at 0° C., and NaBH$_4$ (1.32 g, 34.9 mmol) was added. After the mixture was stirred at 0° C. for 20 min a chip of dry ice was added and the solvent was evaporated. The above residue was dissolved in DCM (100 mL), and washed with satd. aqueous NH$_4$Cl (100 mL). The organic layer was collected, and the aqueous was extracted with DCM (2×50 mL). The combined extract was dried over anhydrous Na$_2$SO$_4$. After filtration the solvent was evaporated under reduced pressure, and the residue was purified on silica gel by flash column chromatography (EtOAc/hexanes, 1:10 to 2:5), affording tert-butyl (-(3aR,5R,6R,7S,7aR)-5-(((tert-butyldimethylsilyoxy)methyl)-7-fluoro-6-hydroxy-5,6,7,7a-tetrahydro-3aH-pyrano[3,2-d]thiazol-2-yl)(methyl)carbamate as a white foam (6.84 g, 76% over 2 steps). $^1$H NMR (400 MHz, CDCl$_3$) δ 6.06 (d, J=6.7 Hz, 1H), 5.01 (td, J=4.3, 46.8 Hz, 1H), 4.49-4.44 (m, 1H), 4.17-4.13 (m, 1H), 3.80-3.79 (m, 2H), 3.66-3.63 (m, 1H), 3.38 (s, 3H), 2.72 (s, br., 1H, (OH)), 1.54 (s, 9H), 0.89 (s, 9H), 0.062 (s, 3H), 0.057 (s, 3H).

At 0° C., to a solution of the above material (1.30 g, 2.89 mmol) and Bu$_4$NI (0.107 g, 0.290 mmol) in anhydrous DMF (12 mL) was added NaH (60% in mineral oil, 0.145 g, 3.63 mmol). After addition of NaH, BnBr (0.989 g, 5.78 mmol) was added. After stirred at 0° C. for 30 min and then at room temperature overnight the mixture was diluted with Et$_2$O (100 mL). The mixture was washed with satd. aqueous NH$_4$Cl (2×50 mL). The aqueous was extracted with Et$_2$O (2×40 mL). The combined extract was washed with brine (50 mL) and dried over anhydrous Na$_2$SO$_4$. After filtration the solvent was evaporated under reduced pressure, and the residue was purified on silica gel by flash column chromatography (EtOAc/hexanes, 1:20 to 1:4), affording tert-butyl (-(3aR,5R,6R,7S,7aR)-6-(benzyloxy)-5-(((tert-butyldimethylsilyl)oxy)methyl)-7-fluoro-5,6,7,7a-tetrahydro-3aH-pyrano[3,2-d]thiazol-2-yl)(methyl)carbamate as a sticky oil (1.44 g, 92%). $^1$H NMR (400 MHz, CDCl$_3$) δ 7.36-7.27 (m, 5H), 6.21 (d, J=7.2 Hz, 1H), 5.30-5.16 (m, 1H), 4.80 (d, J=11.4 Hz, 1H), 4.56 (d, J=11.4 Hz, 1H), 4.50-4.42 (m, 1H), 3.95-3.78 (m, 4H), 3.44 (s, 3H), 1.54 (s, 9H), 0.89 (s, 9H), 0.049 (s, 6H).

At 0° C., to a solution of the above material (1.44 g, 2.66 mmol) in THF (25 mL) was added TBAF (1.0 M in THF, 3.5 mL, 3.5 mmol). After addition the reaction mixture was stirred at room temperature for 2 h and diluted with brine (50 mL). The mixture was extracted with EtOAc (2×40 mL). The combined extract was dried over anhydrous Na$_2$SO$_4$. After filtration the solvent was evaporated under reduced pressure, and the residue was purified on silica gel by flash column chromatography (EtOAc/hexanes, 1:2 to 1:1), affording tert-butyl (-(3aR,5R,6R,7S,7aR)-6-(benzyloxy)-7-fluoro-5-(hydroxymethyl)-5,6,7,7a-tetrahydro-3aH-pyrano[3,2-d]thiazol-2-yl)(methyl)carbamate as a white solid (1.08 g, 95%). $^1$H NMR (400 MHz, CDCl$_3$) δ 7.37-7.27 (m, 5H), 6.18 (d, J=7.4 Hz, 1H), 5.17-5.04 (m, 1H), 4.84 (d, J=11.6 Hz, 1H), 4.55 (d, J=11.6 Hz, 1H), 4.50-4.43 (m, 1H), 3.95-3.91 (m, 1H), 3.88 3.82 (m, 1H), 3.79-3.75 (m, 1H), 3.71-3.67 (m, 1H), 3.37 (s, 3H), 1.53 (s, 9H).

To a solution of the above material (2.57 g, 6.03 mmol) in DCM (60 mL) at 0 t was added DMP (3.82 g, 9.00 mmol). After stirred at room temperature for 1 h the reaction mixture was diluted with Et$_2$O (100 mL). The resulting suspension was filtered through a Celite cake, and the filtrate was concentrated to dryness at room temperature. The residue was extracted with EtOAc (3×50 mL), and the solid was filtered off. The extract was washed mixed satd. aqueous NaHCO$_3$ (30 mL) and Na$_2$S$_2$O$_3$ (5 mL). The extract was collected and dried over anhydrous MgSO$_4$. After filtration the solvent was evaporated under reduced pressure to give the crude aldehyde tert-butyl (-(3aR,5S,6R,7S,7aR)-6-(benzyloxy)-7-fluoro-5-formyl-5,6,7,7a-tetrahydro-3aH-pyrano[3,2-d]thiazol-2-yl)(methyl)carbamate. This crude material was used in the next step without further purification. $^1$H NMR (400 MHz, CDCl$_3$) δ 9.65 (s, 1H), 7.39-7.29 (m, 5H), 6.04 (d, J=7.0 Hz, 1H), 5.08 (td, J=4.2, 46.7 Hz, 1H), 4.84 (d, J=11.4 Hz, 1H), 4.64 (d, J=11.4 Hz, 1H), 4.55-4.49 (m, 1H), 4.31 (d, J=7.5 Hz, 1H), 4.19-4.15 (m, 1H), 3.30 (s, 3H), 1.52 (s, 9H).)

To a solution of the above material (0.19 g, ~80% pure, ~0.36 mmol) in anhydrous DCM (6 mL) at −78° C. under $N_2$, was added DAST (0.37 g, 2.3 mmol). After addition the mixture was stirred at room temperature for 24 h. The reaction mixture was then cooled at 78° C., and quenched with satd. aqueous $NaHCO_3$ (10 mL). The organic layer was collected, and the aqueous was extracted with DCM (2×10 mL). The combined extract was dried over anhydrous $Na_2SO_4$. After filtration the solvent was evaporated under reduced pressure, and the residue was purified on silica gel by flash column chromatography (EtOAc/hexanes, 1:20 to 1:4), affording tert-butyl (-(3aR,5S,6R,7S,7aR)-6-(benzyloxy)-5-(difluoromethyl)-7-fluoro-5,6,7,7a-tetrahydro-3aH-pyrano[3,2-d]thiazol-2-yl)(methyl)carbamate as a white foam (0.097 g, 60%). $^1$H NMR (500 MHz, $CDCl_3$) δ 7.37-7.28 (m, 5H), 6.12 (d, J=6.9 Hz, 1H), 5.85 (dt, J=1.6, 54.5 Hz, 1H), 5.11 (td, J=4.0, 47.3 Hz, 1H), 4.83 (d, J=11.2 Hz, 1H), 4.57 (d, J=11.2 Hz, 1H), 4.55-4.50 (m, 1H), 4.12-4.04 (m, 2H), 3.28 (s, 3H), 1.52 (s, 9H).

To a solution of the above material (0.097 g, 0.22 mmol) and pentamethylbenzene (0.050 g, 0.34 mmol) in anhydrous DCM (3 mL) at −78° C. under $N_2$, was added $BCl_3$ (1.0 M in DCM, 1.0 mL, 1.0 mmol). The mixture was stirred at room temperature for ~5 h while the temperature of the cooling trap reached room temperature. The reaction mixture was cooled at −78° C., quenched with mixed MeOH/DCM, and then concentrated to dryness. The residue was purified on silica gel by flash column chromatography (1.0 M $NH_3$ in MeOH/$CH_2Cl_2$, 1: 12), affording -(3aR,5S,6R,7S,7aR)-5-(difluoromethyl)-7-fluoro-2-(methylamino)-5,6,7,7a-tetrahydro-3aH-pyrano[3,2-d]thiazol-6-ol as a white solid (0.041 g, 72%). $^1$H NMR (400 MHz, $CD_3OD$) δ 6.37 (d, J=6.6 Hz, 1H), 6.04 (dt, J=1.5, 54.0 Hz, 1H), 4.86 (td, J=3.3, 50.9 Hz, 1H), 4.39 (ddd, J=3.8, 6.6, 20.9 Hz, 1H), 4.05-3.95 (m, 2H), 2.86 (s, 3H); $^{13}$C NMR (100 MHz, $CD_3OD$) δ 165.00, 115.89 (t, J=242.6 Hz), 90.65 (d, J=185.7 Hz), 90.25 (d, J=3.5 Hz), 72.22-71.71 (m), 71.71 (d, J=16.1 Hz), 66.22-65.97 (m), 30.48; MS, m/z=257.1 (M+1).

The following examples may be synthesized according to procedures analogous to the schemes and examples outlined above.

TABLE 6

| Example | Structure | Name |
|---|---|---|
| 34 | 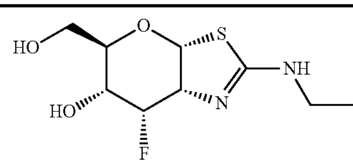 | (3aR,5R,6R,7S,7aR)-2-(ethylamino)-7-fluoro-5-(hydroxymethyl)-5,6,7,7a-tetrahydro-3aH-pyrano[3,2-d]thiazol-6-ol |
| 35 | 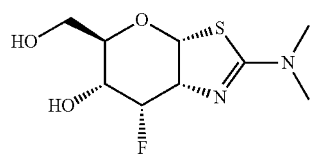 [SMILES: CN(C)C1=N[C@@H]2[C@H](F)[C@H](O)[C@@H](CO)O[C@@H]2S1] | (3aR,5R,6R,7S,7aR)-2-(dimethylamino)-7-fluoro-5-(hydroxymethyl)-5,6,7,7a-tetrahydro-3aH-pyrano[3,2-d]thiazol-6-ol |
| 36 | 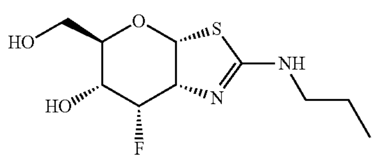 [SMILES: CCCNC1=N[C@@H]2[C@H](F)[C@H](O)[C@@H](CO)O[C@@H]2S1] | (3aR,5R,6R,7S,7aR)-7-fluoro-5-(hydroxymethyl)-2-(propylamino)-5,6,7,7a-tetrahydro-3aH-pyrano[3,2-d]thiazol-6-ol |
| 37 | 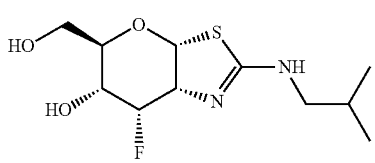 [SMILES: CC(C)CNC1=N[C@@H]2[C@H](F)[C@H](O)[C@@H](CO)O[C@@H]2S1] | (3aR,5R,6R,7S,7aR)-7-fluoro-5-(hydroxymethyl)-2-(isobutylamino)-5,6,7,7a-tetrahydro-3aH-pyrano[3,2-d]thiazol-6-ol |
| 38 | 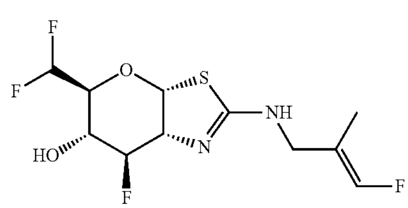 [SMILES: C/C(=C\F)CNC1=N[C@@H]2[C@@H](F)[C@H](O)[C@@H](C(F)F)O[C@@H]2S1] | (3aR,5S,6R,7R,7aR)-5-(difluoromethyl)-7-fluoro-2-(((E)-3-fluoro-2-methylallyl)amino)-5,6,7,7a-tetrahydro-3aH-pyrano[3,2-d]thiazol-6-ol |
| 39 | 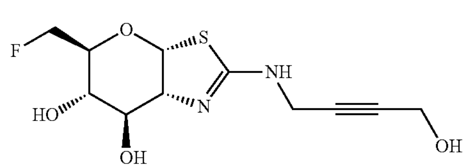 [SMILES: OCC#CCNC1=N[C@@H]2[C@@H](O)[C@H](O)[C@@H](CF)O[C@@H]2S1] | (3aR,5S,6S,7R,7aR)-5-(fluoromethyl)-2-((4-hydroxybut-2-yn-1-yl)amino)-5,6,7,7a-tetrahydro-3aH-pyrano[3,2-d]thiazole-6,7-diol |

TABLE 6-continued

| Example | Structure | Name |
|---|---|---|
| 40 | 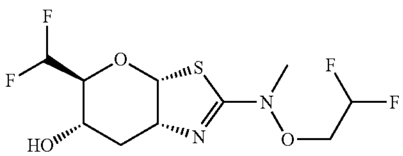 [SMILES: CN(OCC(F)F)C1=N[C@@H]2C[C@H](O)[C@@H](C(F)F)O[C@@H]2S1] | (3aR,5S,6S,7aR)-2-((2,2-difluoroethoxy)(methyl)amino)-5-(difluoromethyl)-5,6,7,7a-tetrahydro-3aH-pyrano[3,2-d]thiazol-6-ol |
| 41 | 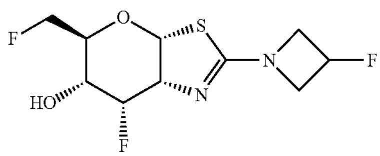 [SMILES: O[C@H]1[C@@H](F)[C@H]2N=C(N3CC(F)C3)S[C@H]2O[C@@H]1CF] | (3aR,5S,6R,7S,7aR)-7-fluoro-2-(3-fluoroazetidin-1-yl)-5-(fluoromethyl)-5,6,7,7a-tetrahydro-3aH-pyrano[3,2-d]thiazol-6-ol |
| 42 | 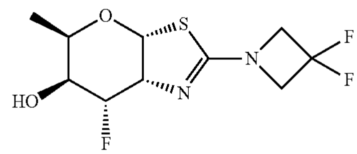 [SMILES: C[C@H]1O[C@@H]2SC(N3CC(F)(F)C3)=N[C@@H]2[C@H](F)[C@H]1O] | (3aR,5R,6S,7S,7aR)-2-(3,3-difluoroazetidin-1-yl)-7-fluoro-5-methyl-5,6,7,7a-tetrahydro-3aH-pyrano[3,2-d]thiazol-6-ol |

Biological Activity

Assay for Determination of $K_1$ Values for Inhibition of O-GlcNAcase Activity Experimental procedure for kinetic analyses: Enzymatic reactions were carried out in a reaction containing 50 mM $NaH_2PO_4$, 100 mM NaCl and 0.1% BSA (pH 7.0) using 2 mM 4-Methylumbelliferyl N-acetyl-β-D-glucosaminide dihydrate (Sigma M2133) dissolved in $ddH_2O$, as a substrate. The amount of purified human O-GlcNAcase enzyme used in the reaction was 0.7 nM. Test compound of varying concentrations was added to the enzyme prior to initiation of the reaction. The reaction was performed at room temperature in a 96-well plate and was initiated with the addition of substrate. The production of fluorescent product was measured every 60 sec for 45 min with a Tecan Infinite M200 plate-reader with excitation at 355 nM and emission detected at 460 nM, with 4-Methylumbelliferone (Sigma M1381) used to produce a standard curve. The slope of product production was determined for each concentration of compound tested and plotted, using standard curve fitting algorithms for sigmoidal dose response curves. The values for a four parameter logistic curve fit of the data were determined.

$K_1$ values were determined using the Cheng-Prusoff equation; the $K_m$ of O-GlcNAcase for substrate was 0.2 mM.

Examples 1 to 33 were tested in the above described assay and exhibited $K_1$ values for inhibition of O-GlcNAcase in the range 0.1 nM-10 pt,M.

Assay for Determination of $K_1$ Values for Inhibition of β-Hexosaminidase Activity Experimental procedure for kinetic analyses: Enzymatic reactions were carried out in a reaction containing 50 mM $NaH_2PO_4$, 100 mM NaCl and 0.1% BSA (pH 7.0) using 2 mM 4-Methylumbelliferyl N-acetyl-β-D-glucosaminide dihydrate (Sigma M2133) dissolved in $ddH_2O$, as a substrate. The amount of purified human β-hexosaminidase enzyme used in the reaction was 24 nM. Test compound of varying concentrations was added to the enzyme prior to initiation of the reaction. The reaction was performed at room temperature in a 96-well plate and was initiated with the addition of substrate. The production of fluorescent product was measured every 60 sec for 45 min with a Tecan Infinite M200 plate-reader with excitation at 355 nM and emission detected at 460 nM, with 4-Methylumbelliferone (Sigma M1381) used to produce a standard curve. The slope of product production was determined for each concentration of compound tested and plotted, using standard curve fitting algorithms for sigmoidal dose response curves. The values for a four parameter logistic curve fit of the data were determined.

$K_1$ values were determined using the Cheng-Prusoff equation.

When tested in this assay, many of the compounds described herein exhibit $K_1$ values for inhibition of β-hexosaminidase in the range 10 nM to greater than 100 uM.

The selectivity ratio for inhibition of O-GlcNAcase over β-hexosaminidase is defined here as:

$K_1$(β-hexosamimidase)/$K_1$(O-GlcNAcase)

In general, the compounds described herein exhibited a selectivity ratio in the range of about 10 to 100000. Thus, many compounds of the invention exhibit high selectivity for inhibition of O-GlcNAcase over β-hexosaminidase.

Assay for Determination of Cellular Activity for Compounds that Inhibit O-GlcNAcase Activity Inhibition of O-GlcNAcase, which removes O-GlcNAc from cellular proteins, results in an increase in the level of O-GlcNAcylated protein in cells. An increase in O-GlcNAcylated protein can be measured by an antibody, such as RL-2, that binds to O-GlcNAcylated protein. The amount of O-GleNAcylated protein:RL2 antibody interaction can be measured by enzyme linked immunosorbant assay (ELISA) procedures.

A variety of tissue culture cell lines, expressing endogenous levels of O-GlcNAcase, can be utilized; examples include rat PC-12, and human U-87, or SK-N-SH cells. In this assay,rat PC-12 cells were plated in 96-well plates with approximately 10,000 cells/well. Compounds to be tested were dissolved in DMSO, either 2 or 10 mM stock solution, and then diluted with DMSO and water in a two-step process using a Tecan workstation. Cells were treated with diluted compounds for 24 h (5.4 μL into 200 μL I well volume) to reach a final concentration of inhibitor desired to measure a compound concentration dependent response, typically, ten 3 fold dilution steps, starting at 10 µM were used to determine a concentration response curve. To prepare a cell lysate, the media from compound treated cells was removed, the cells were washed once with phosphate buffered saline (PBS) and then lysed for 5 minutes at room temperature in 50 µL of Phosphosafe reagent (Novagen Inc, Madison, Wis.) with protease inhibitors and PMSF. The cell lysate was collected and transferred to a new plate, which was then either coated to assay plates directly or frozen −80° C. until used in the ELISA procedure. If desired, the total protein concentration of samples was determined using 20 µL of the sample using the BCA method.

The ELISA portion of the assay was performed in a black Maxisorp 96-well plate that was coated overnight at 4° C. with 100 µL/well of the cell lysate (1:10 dilution of the lysate with PBS containing protease inhibitors, phosphatase inhibitors, and PMSF). The following day the wells were washed 3 times with 300 µL/well of Wash buffer (Tris-buffered saline with 0.1% Tween 20). The wells were blocked with 100 µl/well Blocking buffer (Tris buffered saline w/0.05% Tween 20 and 2.5% Bovine serum albumin). Each well was then washed two times with 300 µL/well of wash buffer. The anti O-GlcNAc antibody RL-2 (Abcam, Cambridge, Mass.), diluted 1:1000 in blocking buffer, was added at 100 µL/well. The plate was sealed and incubated at 37° C. for 2 h with gentle shaking. The wells were then washed 3-times with 300 µL/well wash buffer. To detect the amount of RL-2 bound horse-radish peroxidase (HRP) conjugated goat anti-mouse secondary antibody (diluted 1:3000 in blocking buffer) was added at 100 µL/well. The plate was incubated for 60 min at 37° C. with gentle shaking. Each well was then washed 3-times with 300 µL/well wash buffer. The detection reagent was added, 100 µL/well of Amplex Ultra RED reagent (prepared by adding 30 µL of 10 mM Amplex Ultra Red stock solution to 10 mL PBS with 18 µL 3% hydrogen peroxide, $H_2O_2$). The detection reaction was incubated for 15 minutes at room temperature and then read with excitation at 530 nm and emission at 590 nm.

The amount of O-GlcNAcylated protein, as detected by the ELISA assay, was plotted for each concentration of test compound using standard curve fitting algorithms for sigmoidal dose response curves. The values for a four parameter logistic curve fit of the data were determined, with the inflection point of the curve being the potency value for the test compound.

Assay for Determination of Apparent Permeability ($P_{app}$)

Bi-directional transport was evaluated in LLC-PK1 cells in order to determine apparent permeability ($P_{app}$). LLC-PK1 cells can form a tight monolayer and therefore can be used to assess vectorial transport of compounds from basolateral to apical (B→A) and from apical to basolateral (A→B).

To determine $P_{app}$, LLC-PK1 cells were cultured in 96-well transwell culture plates (Millipore). Solutions containing the test compounds (1 µM) were prepared in Hank's Balanced Salt Solution with 10 mM HEPES. Substrate solution (150 µL) was added to either the apical (A) or the basolateral (B) compartment of the culture plate, and buffer (150 µL) was added to the compartment opposite to that containing the compound. At t=3 h, 50 µL samples were removed from both sides of monolayers dosed with test compound and placed in 96 well plates, scintillant (200 µL) or internal standard (100 µL labetolol 104) was added to the samples and concentration was determined by liquid scintillation counting in a MicroBeta Wallac Trilux scintillation counter (Perkin Elmer Life Sciences, Boston, Mass.) or by LCMS/MS (Applied Biosystems SCIEX API 5000 triple quadruple mass spectrometer). [$^3$H]Verapamil (1 µM) was used as the positive control. The experiment was performed in triplicate.

The apparent permeability, $P_{app}$, was calculated by the following formula for samples taken at t=3 h:

$$P_{app} = \frac{\text{Volume of Receptor Chamber (mL)}}{[\text{Area of membrane (cm}^2)][\text{Initial Concentration }(\mu M)]} \times \frac{\Delta \text{ in Concentration } (\mu M)}{\Delta \text{ in Time(s)}}$$

Where: Volume of Receptor Chamber was 0.15 mL; Area of membrane was 0.11 cm$^2$; the Initial Concentration is the sum of the concentration measured in the donor plus concentration measured in receiver compartments at t=3 h; Δ in Concentration is concentration in the receiver compartment at 3 h; and Δ in Time is the incubation time (3×60×60=10800 s). $P_{app}$ was expressed as 10$^{-6}$ cm/s. The $P_{app}$ (LLC-PK1 cells) are the average of the $P_{app}$ for transport from A to B and $P_{app}$ for transport from B to A at t=3 h:

$$P_{app}(LLC-PK1 \text{ Cells}) = \frac{P_{app}(A \to B) + P_{app}(B \to A)}{2}$$

Representative data from the binding, cell-based, and permeability assays described above are shown in the following table. Certain compounds of the invention exhibited superior potency or permeability in one or more of these assays as compared to compounds disclosed in WO 2006/092049 and WO 2008/025170. For comparison, the first two table entries show data for compounds -(3aR,5R,6S,7R,7aR)-2-(ethylamino)-5-(hydroxymethyl)-5,6,7,7a-tetrahydro-3aH-pyrano[3,2-d]thiazole-6,7-diol and -(3aR,5R,6S,7R,7aR)-2-(dimethylamino)-5-(hydroxymethyl)-5,6,7,7a-tetrahydro-3aH-pyrano[3,2-d]thiazole-6,7-diol, disclosed in WO 2008/025170.

| Example | Structure | Cell-based ELISA $EC_{50}$ (nM) | Fluorescence-based hOGA Ki (nM) | Papp LLC-PK-1 cells ($10^{-6}$ cm/s) |
|---|---|---|---|---|
| N/A | 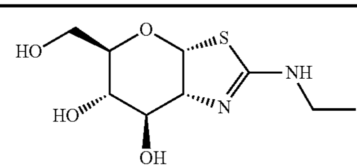 | 13 | 0.4 | <1.0 |

-continued
| Example | Structure | Cell-based ELISA $EC_{50}$ (nM) | Fluorescence-based hOGA $K_i$ (nM) | Papp LLC-PK-1 cells ($10^{-6}$ cm/s) |
|---|---|---|---|---|
| N/A | 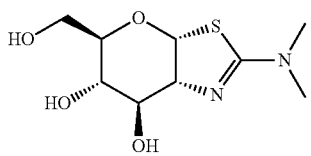 [SMILES: CN(C)C1=N[C@@H]2[C@@H](O)[C@H](O)[C@@H](CO)O[C@@H]2S1] | 10 | 0.3 | <1.0 |
| 1 | 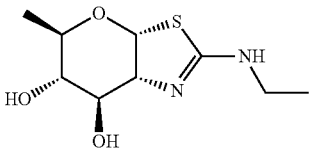 | ND | 70 | ND |
| 2 | 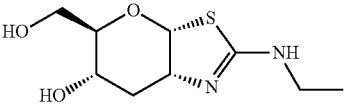 | 365 | 44 | 3.8 |
| 4 | 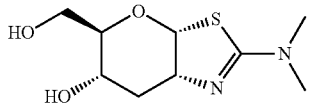 | 358 | 13 | ND |
| 9 | 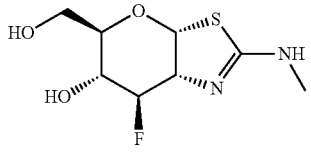 | 307 | 1.3 | ND |
| 17 | 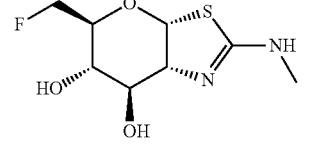 | 34 | 0.5 | 7.1 |
| 19 | 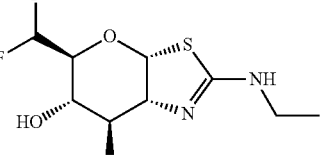 | 53 | 5.7 | 6.0 |
| 20 | 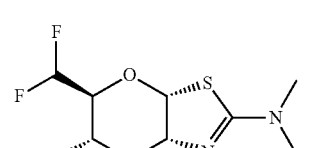 | 6.0 | 1.4 | 13.7 |
| 27 | 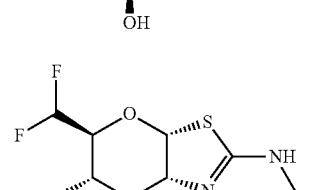 | ND | 28 | 24.0 |

| Example | Structure | Cell-based ELISA EC$_{50}$ (nM) | Fluorescence-based hOGA Ki (nM) | Papp LLC-PK-1 cells (10$^{-6}$ cm/s) |
|---|---|---|---|---|
| 29 | 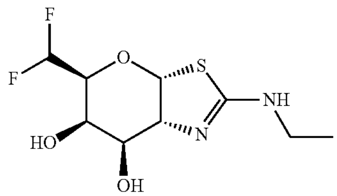 [SMILES: CCNC1=N[C@@H]2[C@@H](O)[C@@H](O)[C@@H](C(F)F)O[C@@H]2S1] | ND | 164 | ND |
| 33 | 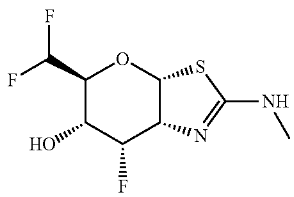 [SMILES: CNC1=N[C@@H]2[C@H](F)[C@H](O)[C@@H](C(F)F)O[C@@H]2S1] | ND | 13 | 20.1 |

The present invention has been described with regard to one or more embodiments. However, it will be apparent to persons skilled in the art that a number of variations and modifications can be made without departing from the scope of the invention as defined in the claims.

REFERENCES

1. C. R. Torres, G. W. Hart, *J Biol Chem* 1984, 259, 3308.
2. R. S. Haltiwanger, G. D. Holt, G. W. Hart, *J Biol Chem* 1990, 265, 2563.
3. L. K. Kreppel, M. A. Blomberg, G. W. Hart, *J Biol Chem* 1997, 272, 9308.
4. W. A. Lubas, D. W. Frank, M. Krause, J. A. Hanover, *J Biol Chem* 1997, 272, 9316.
5. W. A. Lubas, J. A. Hanover, *J Biol Chem* 2000, 275, 10983.
6. D. L. Dong, G. W. Hart, *J Biol Chem* 1994, 269, 19321.
7. Y. Gao, L. Wells, F. I. Comer, G. J. Parker, G. W. Hart, *J Biol Chem* 2001, 276, 9838.
8. E. P. Roquemore, M. R. Chevrier, R. J. Cotter, G. W. Hart, *Biochemistry* 1996, 35, 3578.
9. S. P. Jackson, R. Tjian, *Cell* 1988, 55, 125.
10. W. G. Kelly, M. E. Dahmus, G. W. Hart, *J Biol Chem* 1993, 268, 10416.
11. M. D. Roos, K. Su, J. R. Baker, J. E. Kudlow, *Mol Cell Biol* 1997, 17, 6472.
12. N. Lamarre-Vincent, L. C. Hsieh-Wilson, *J Am Chem Soc* 2003, 125, 6612.
13. F. Zhang, K. Su, X. Yang, D. B. Bowe, A. J. Paterson, J. E. Kudlow, *Cell* 2003, 115, 715.
14. K. Vosseller, L. Wells, M. D. Lane, G. W. Hart, *Proc Natl Acad Sci USA* 2002, 99, 5313.
15. W. A. Lubas, M. Smith, C. M. Starr, J. A. Hanover, *Biochemistry* 1995, 34, 1686.
16. L. S. Griffith, B. Schmitz, *Biochem Biophys Res Commun* 1995, 213, 424.
17. R. N. Cole, G. W. Hart, *J Neurochem* 1999, 73, 418.
18I. Braidman, M. Carroll, N. Dance, D. Robinson, *Biochem J* 1974, 143, 295.
19. R. Ueno, C. S. Yuan, *Biochim Biophys Acta* 1991, 1074, 79.
20. C. Toleman, A. J. Paterson, T. R. Whisenhunt, J. E. Kudlow, *J Biol Chem* 2004.
21. F. Liu, K. Iqbal, I. Grundke-Iqbal, G. W. Hart, C. X. Gong, *Proc Natl Acad Sci USA* 2004, 101, 10804.
22. T. Y. Chou, G. W. Hart, *Adv Exp Med Biol* 2001, 491, 413.
23. M. Goedert, M. G. Spillantini, N.J. Cairns, R. A. Crowther, *Neuron* 1992, 8, 159.
24. M. Goedert, M. G. Spillantini, R. Jakes, D. Rutherford, R. A. Crowther, *Neuron* 1989, 3, 519.
25. E. Kopke, Y. C. Tung, S. Shaikh, A. C. Alonso, K. Iqbal, I. Grundke-Iqbal, *J Biol Chem* 1993, 268, 24374.
26. H. Ksiezak-Reding, W. K. Liu, S. H. Yen, *Brain Res* 1992, 597, 209.
27. B. Henrissat, A. Bairoch, *Biochem J* 1996, 316 (Pt 2), 695.
28. B. Henrissat, A. Bairoch, *Biochem J* 1993, 293 (Pt 3), 781.
29. C. X. Gong, F. Liu, I. Grundke-Iqbal, K. Iqbal, *J Neural Transm* 2005, 112, 813.
30. K. Iqbal, C. Alonso Adel, E. El-Akkad, C. X. Gong, N. Hague, S. Khatoon, I. Tsujio, I. Grundke-Iqbal, *J Neural Transm Suppl* 2002, 309.
31. K. Iqbal, C. Alonso Adel, E. El-Akkad, C. X. Gong, N. Hague, S. Khatoon, J. J. Pei, H. Tanimukai, I. Tsujio, et al., *J Mol Neurosci* 2003, 20, 425.
32. W. Noble, E. Planel, C. Zehr, V. Olm, J. Meyerson, F. Suleman, K. Gaynor, L. Wang, J. LaFrancois, et al., *Proc Natl Acad Sci USA* 2005, 102, 6990.
33. S. Le Corre, H. W. Klafki, N. Plesnila, G. Hubinger, A. Obermeier, H. Sahagun, B. Monse, P. Seneci, J. Lewis, et al., *Proc Natl Acad Sci USA* 2006, 103, 9673.
34. S. J. Liu, J. Y. Zhang, H. L. Li, Z. Y. Fang, Q. Wang, H. M. Deng, C. X. Gong, I. Grundke-Iqbal, K. Iqbal, et al., *J Biol Chem* 2004, 279, 50078.
35. G. Li, H. Yin, J. Kuret, *J Biol Chem* 2004, 279, 15938.
36. T. Y. Chou, G. W. Hart, C. V. Dang, *J Biol Chem* 1995, 270, 18961.
37. X. Cheng, G. W. Hart, *J Biol Chem* 2001, 276, 10570.
38. X. Cheng, R. N. Cole, J. Zaia, G. W. Hart, *Biochemistry* 2000, 39, 11609.
39. L. S. Griffith, B. Schmitz, *Eur J Biochem* 1999, 262, 824.
40. K. Kamemura, G. W. Hart, *Prog Nucleic Acid Res Mol Biol* 2003, 73, 107.
41. L. Wells, L. K. Kreppel, F. I. Comer, B. E. Wadzinski, G. W. Hart, *J Biol Chem* 2004, 279, 38466.
42. L. Bertram, D. Blacker, K. Mullin, D. Keeney, J. Jones, S. Basu, S. Yhu, M. G. McInnis, R. C. Go, et al., *Science* 2000, 290, 2302.

43. S. Hoyer, D. Blum-Degen, H. G. Bernstein, S. Engelsberger, J. Humrich, S. Laufer, D. Muschner, A. Thalheimer, A. Turk, et al., *Journal of Neural Transmission* 1998, 105, 423.
44. C. X. Gong, F. Liu, I. Grundke-Iqbal, K. Iqbal, *Journal of Alzheimers Disease* 2006, 9, 1
45. W. J. Jagust, J. P. Seab, R. H. Huesman, P. E. Valk, C. A. Mathis, B. R. Reed, P. G. Coxson, T. F. Budinger, *Journal of Cerebral Blood Flow and Metabolism* 1991, 11, 323
46. S. Hoyer, *Experimental Gerontology* 2000, 35, 1363.
47. S. Hoyer, in *Frontiers in Clinical Neuroscience: Neurodegeneration and Neuroprotection*, Vol. 541, 2004, pp. 135.
48. R. N. Kalaria, S. I. Harik, *Journal of Neurochemistry* 1989, 53, 1083.
49. I. A. Simpson, K. R. Chundu, T. Davieshill, W. G. Honer, P. Davies, *Annals of Neurology* 1994, 35, 546.
50. S. M. de la Monte, J. R. Wands, *Journal of Alzheimers Disease* 2005, 7, 45.
51. X. W. Zhu, G. Perry, M. A. Smith, *Journal of Alzheimers Disease* 2005, 7, 81.
52. J. C. de la Torre, *Neurological Research* 2004, 26, 517.
53. S. Marshall, W. T. Garvey, R. R. Traxinger, *Faseb J* 1991, 5, 3031.
54. S. P. Iyer, Y. Akimoto, G. W. Hart, *J Biol Chem* 2003, 278, 5399.
55. K. Brickley, M. J. Smith, M. Beck, F. A. Stephenson, *J Biol Chem* 2005, 280, 14723.
56. S. Knapp, C. H. Yang, T. Haimowitz, *Tetrahedron Letters* 2002, 43, 7101.
57. S. P. Iyer, G. W. Hart, *J Biol Chem* 2003, 278, 24608.
58. M. Jinek, J. Rehwinkel, B. D. Lazarus, E. Izaurralde, J. A. Hanover, E. Conti, *Nat Struct Mol Biol* 2004, 11, 1001.
59. K. Kamemura, B. K. Hayes, F. I. Corner, G. W. Hart, *J Biol Chem* 2002, 277, 19229.
60. Y. Deng, B. Li, F. Liu, K. Iqbal, I. Grundke-Iqbal, R. Brandt, C.-X. Gong, *FASEB J.* 2007, fj.07.
61. L. F. Lau, J. B. Schachter, P. A. Seymour, M. A. Sanner, *Curr Top Med Chem* 2002, 2, 395.
62. M. P. Mazanetz, P. M. Fischer, *Nature Reviews Drug Discovery* 2007, 6, 464.
63. S. A. Yuzwa, M. S. Macauley, J. E. Heinonen, X. Shan, R. J. Dennis, Y. He, G. E. Whitworth, K. A. Stubbs, E. J. McEachern, et al., *Nat Chem Biol* 2008, 4, 483.
64. P. Bounelis, J. Liu, Y. Pang, J. C. Chatham, R. B. Marchase, *Shock* 2004, 21 170 *Suppl. 2*, 58.
65. N. Fulop, V. Champattanachal, R. B. Marchase, J. C. Chatham, *Circulation Research* 2005, 97, E28.
66. J. Liu, R. B. Marchase, J. C. Chatham, *Faseb Journal* 2006, 20, A317.
67. R. Marchase, P. Bounelis, J. Chatham, I. Chaudry, Y. Pang, *PCT Int. Appl.* WO 2006016904 2006.
68. N. Fulop, P. P. Wang, R. B. Marchase, J. C. Chatham, *Journal of Molecular and Cellular Cardiology* 2004, 37, 286.
69. N. Fulop, P. P. Wang, R. B. Marchase, J. C. Chatham, *Faseb Journal* 2005, 19, A689.
70. J. Liu, R. B. Marchase, J. C. Chatham, *Journal of Molecular and Cellular Cardiology* 2007, 42, 177.
71. L. G. Not, C. A. Brocks, N. Fulop, R. B. Marchase, J. C. Chatham, *Faseb Journal* 2006, 20, A1471.
72. S. L. Yang, L. Y. Zou, P. Bounelis, I. Chaudry, J. C. Chatham, R. B. Marchase, *Shock* 2006, 25, 600.
73. L. Y. Zou, S. L. Yang, P. Bounelis, I. H. Chaudry, J. C. Chatham, R. B. Marchase, *Faseb Journal* 2005, 19, A1224.
74. R. B. Marchase, J. Liu, L. Y. Zou, V. Champattanachai, Y. Pang, N. Fulop, P. P. Wang, S. L. Yang, P. Bounelis, et al., *Circulation* 2004, 110, 1099.
75. J. Liu, Y. Pang, T. Chang, P. Bounelis, J. C. Chatham, R. B. Marchase, *Journal of Molecular and Cellular Cardiology* 2006, 40, 303.
76. J. Liu, J. C. Chatham, R. B. Marchase, *Faseb Journal* 2005, 19, A691.
77. T. Nagy, V. Champattanachai, R. B. Marchase, J. C. Chatham, American *Journal of Physiology-Cell Physiology* 2006, 290, C57.
78. N. Fulop, R. B. Marchase, J. C. Chatham, *Cardiovascular Research* 2007, 73, 288.
79. T. Lefebvre, C. Guinez, V. Dehennaut, O. Beseme-Dekeyser, W. Morelle, J. C. Michalski, *Expert Review of Proteomics* 2005, 2, 265.
80. L. Wells, K. Vosseller, G. W. Hart, *Science* 2001, 291, 2376.
81. J. A. Hanover, *FASEB J* 2001, 15, 1865.
82. D. A. McClain, W. A. Lubas, R. C. Cooksey, M. Hazel, G. J. Parker, D.C. Love, J. A. Hanover, *Proc Natl Acad Sci USA* 2002, 99, 10695.
83. P. J. Yao, P. D. Coleman, *J Neurosci* 1998, 18, 2399.
84. W. H. Yang, J. E. Kim, H. W. Nam, J. W. Ju, H. S. Kim, Y. S. Kim, J. W. Cho, *Nature Cell Biology* 2006, 8, 1074.
85. B. Triggs-Raine, D. J. Mahuran, R. A. Gravel, *Adv Genet.* 2001, 44, 199.
86. D. Zhou, J. Mattner, C. Cantu Iii, N. Schrantz, N. Yin, Y. Gao, Y. Sagiv, K. Hudspeth, Y. Wu, et al., *Science* 2004.
87. G. Legler, E. Lullau, E. Kappes, F. Kastenholz, *Biochim Biophys Acta* 1991, 1080, 89.
88. M. Horsch, L. Hoesch, A. Vasella, D. M. Rast, *Eur J Biochem* 1991, 197, 815.
89. J. Liu, A. R. Shikhman, M. K. Lotz, C. H. Wong, *Chem Biol* 2001, 8, 701.
90. S. Knapp, D. J. Vocadlo, Z. N. Gao, B. Kirk, J. P. Lou, S. G. Withers, *J. Am. Chem. Soc.* 1996, 118, 6804.
91. V. H. Lillelund, H. H. Jensen, X. Liang, M. Bols, *Chem Rev* 2002, 102, 515.
92. R. J. Konrad, I. Mikolaenko, J. F. Tolar, K. Liu, J. E. Kudlow, *Biochem J* 2001, 356, 31.
93. K. Liu, A. J. Paterson, F. Zhang, J. McAndrew, K. Fukuchi, J. M. Wyss, L. Peng, Y. Hu, J. E. Kudlow, *J Neurochem* 2004, 89, 1044.
94. G. Parker, R. Taylor, D. Jones, D. McClain, *J Biol Chem* 2004, 279, 20636.
95. E. B. Arias, J. Kim, G. D. Cartee, *Diabetes* 2004, 53, 921.
96. A. Junod, A. E. Lambert, L. Orci, R. Pictet, A. E. Gonet, A. E. Renold, *Proc Soc Exp Biol Med* 1967, 126, 201.
97. R. A. Bennett, A. E. Pegg, *Cancer Res* 1981, 41, 2786.
98. K. D. Kroncke, K. Fehsel, A. Sommer, M. L. Rodriguez, V. Kolb-Bachofen, *Biol Chem Hoppe Seyler* 1995, 376, 179.
99. H. Yamamoto, Y. Uchigata, H. Okamoto, *Nature* 1981, 294, 284.
100. K. Yamada, K. Nonaka, T. Hanafusa, A. Miyazaki, H. Toyoshima, S. Tarui, *Diabetes* 1982, 31, 749.
101. V. Burkart, Z. Q. Wang, J. Radons, B. Heller, Z. Herceg, L. Stingl, E. F. Wagner, H. Kolb, *Nat Med* 1999, 5, 314.
102. M. D. Roos, W. Xie, K. Su, J. A. Clark, X. Yang, E. Chin, A. J. Paterson, J. E. Kudlow, *Proc Assoc Am Physicians* 1998, 110, 422.
103. Y. Gao, G. J. Parker, G. W. Hart, *Arch Biochem Biophys* 2000, 383, 296.
104. R. Okuyama, M. Yachi, *Biochem Biophys Res Commun* 2001, 287, 366.

105. N. E. Zachara, N. O'Donnell, W. D. Cheung, J. J. Mercer, J. D. Marth, G. W. Hart, *J Biol Chem* 2004, 279, 30133.
106. J. A. Hanover, Z. Lai, G. Lee, W. A. Lubas, S. M. Sato, *Arch Biochem Biophys* 1999, 362, 38.
107. K. Liu, A. J. Paterson, R. J. Konrad, A. F. Parlow, S. Jimi, M. Roh, E. Chin, Jr., J. E. Kudlow, *Mol Cell Endocrinol* 2002, 194, 135.
108. M. S. Macauley, G. E. Whitworth, A. W. Debowski, D. Chin, D. J. Vocadlo, *J Biol Chem* 2005, 280, 25313.
109. B. L. Mark, D. J. Vocadlo, S. Knapp, B. L. Triggs-Raine, S. G. Withers, M. N. James, *Biol Chem* 2001, 276, 10330.
110. R. S. Haltiwanger, K. Grove, G. A. Philipsberg, *J Biol Chem* 1998, 273, 3611.
111. D. J. Miller, X. Gong, B. D. Shur, *Development* 1993, 118, 1279.
112. L. Y. Zou, S. L. Yang, S. H. Hu, I. H. Chaudry, R. B. Marchase, J. C. Chatham, *Shock* 2007, 27, 402.
113. J. B. Huang, A. J. Clark, H. R. Petty, *Cellular Immunology* 2007, 245, 1.
114. U. J. G. Conference, in *US/Japan Glyco* 2004 *Conference, Honolulu, Hi.,* 2004.
115. L. Y. Zou, S. L. Yang, S. H. Hu, I. H. Chaudry, R. B. Marchase, J. C. Chatham, *Faseb Journal* 2006, 20, A1471.
116. V. Champattanachai, R. B. Marchase, J. C. Chatham, *American Journal of Physiology-Cell Physiology* 2007, 292, C 178.
117. V. Champattanachai, R. B. Marchase, J. C. Chatham, *American Journal of Physiology-Cell Physiology* 2008, 294, C1509.
118. I. Khlistunova, M. Pickhardt, J. Biernat, Y. P. Wang, E. M. Mandelkow, E. Mandelkow, *Current Alzheimer Research* 2007, 4, 544.
119. P. Friedhoff, A. Schneider, E. M. Mandelkow, E. Mandelkow, *Biochemistry* 1998, 37, 10223.
120. M. Pickhardt, Z. Gazova, M. von Bergen, I. Khlistunova, Y. P. Wang, A. Hascher, E. M. Mandelkow, J. Biernat, E. Mandelkow, *Journal of Biological Chemistry* 2005, 280, 3628.

What is claimed is:

1. A compound which is

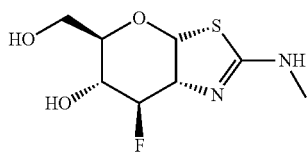

or a pharmaceutically acceptable salt thereof.

2. A compound which is

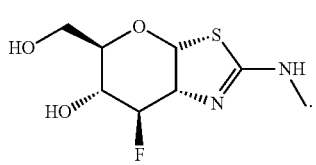

3. A compound which is

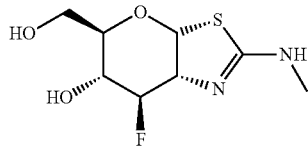

in the form of a pharmaceutically acceptable salt thereof.

4. A compound which is

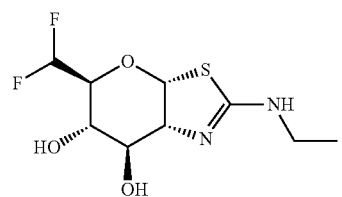

or a pharmaceutically acceptable salt thereof.

5. A compound which is

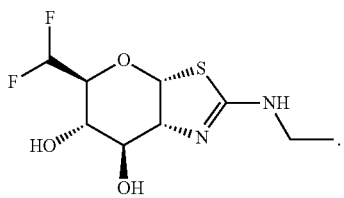 [SMILES: CCNC1=N[C@@H]2[C@@H](O)[C@H](O)[C@@H](C(F)F)O[C@@H]2S1]

6. A compound which is

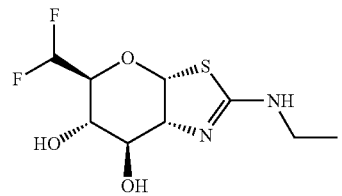 [SMILES: CCNC1=N[C@@H]2[C@@H](O)[C@H](O)[C@@H](C(F)F)O[C@@H]2S1]

in the form of a pharmaceutically acceptable salt thereof.

7. A compound which is

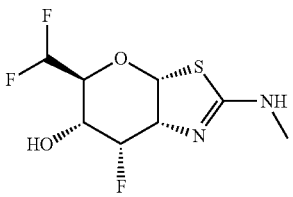 [SMILES: CNC1=N[C@@H]2[C@H](F)[C@H](O)[C@@H](C(F)F)O[C@@H]2S1]

or a pharmaceutically acceptable salt thereof.

8. A compound which is

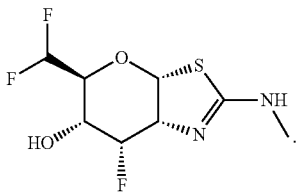 [SMILES: CNC1=N[C@@H]2[C@H](F)[C@H](O)[C@@H](C(F)F)O[C@@H]2S1]

9. A compound which is

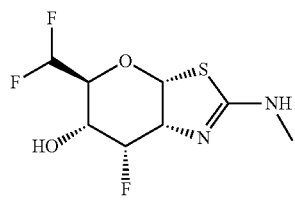

in the form of a pharmaceutically acceptable salt thereof.

10. A pharmaceutical composition comprising a compound which is

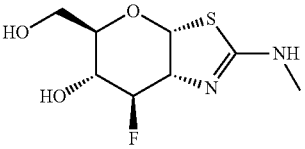

or a pharmaceutically acceptable salt thereof and a pharmaceutically acceptable carrier.

11. The pharmaceutical composition of claim 10 wherein the compound is

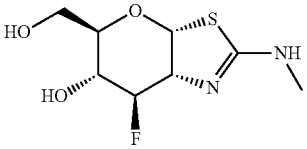

12. The pharmaceutical composition of claim 10 wherein the compound is

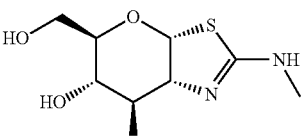

in the form of a pharmaceutically acceptable salt thereof.

13. A pharmaceutical composition comprising a compound which is

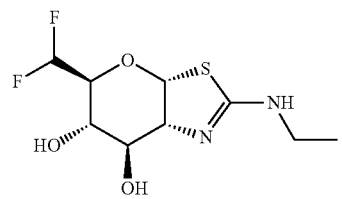 [SMILES: CCNC1=N[C@@H]2[C@@H](O)[C@H](O)[C@@H](C(F)F)O[C@@H]2S1]

or a pharmaceutically acceptable salt thereof and a pharmaceutically acceptable carrier.

14. The pharmaceutical composition of claim 13 wherein the compound is

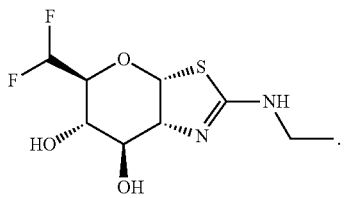

15. The pharmaceutical composition of claim 13 wherein the compound is

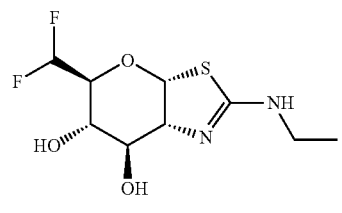

in the form of a pharmaceutically acceptable salt thereof.

16. A pharmaceutical composition comprising a compound which is

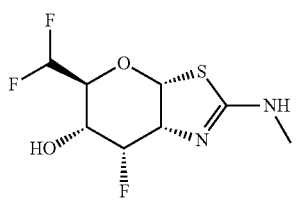 [SMILES: CNC1=N[C@@H]2[C@H](F)[C@H](O)[C@@H](C(F)F)O[C@@H]2S1]

or a pharmaceutically acceptable salt thereof and a pharmaceutically acceptable carrier.

17. The pharmaceutical composition of claim 16 wherein the compound is

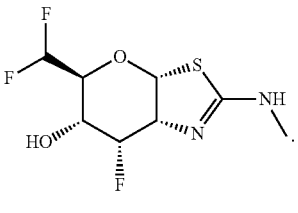 [SMILES: CNC1=N[C@@H]2[C@H](F)[C@H](O)[C@@H](C(F)F)O[C@@H]2S1]

18. The pharmaceutical composition of claim 16 wherein the compound is in the form of a pharmaceutically acceptable salt thereof.

19. A method of treating Alzheimer's disease in a human patient in need thereof which comprises administering to the patient a therapeutically effective amount of the compound of claim 1 or a pharmaceutically acceptable salt thereof.

20. A method of treating Alzheimer's disease in a human patient in need thereof which comprises administering to the patient a therapeutically effective amount of the compound of claim 2.

21. A method of treating Alzheimer's disease in a human patient in need thereof which comprises administering to the patient a therapeutically effective amount of the compound of claim 3 in the form of a pharmaceutically acceptable salt thereof.

22. A method of treating Alzheimer's disease in a human patient in need thereof which comprises administering to the patient a therapeutically effective amount of the compound of claim 4 or a pharmaceutically acceptable salt thereof.

23. A method of treating Alzheimer's disease in a human patient in need thereof which comprises administering to the patient a therapeutically effective amount of the compound of claim 5.

24. A method of treating Alzheimer's disease in a human patient in need thereof which comprises administering to the patient a therapeutically effective amount of the compound of claim 6 in the form of a pharmaceutically acceptable salt thereof.

25. A method of treating Alzheimer's disease in a human patient in need thereof which comprises administering to the patient a therapeutically effective amount of the compound of claim 7 or a pharmaceutically acceptable salt thereof.

26. A method of treating Alzheimer's disease in a human patient in need thereof which comprises administering to the patient a therapeutically effective amount of the compound of claim 8.

27. A method of treating Alzheimer's disease in a human patient in need thereof which comprises administering to the patient a therapeutically effective amount of the compound of claim 8 in the form of pharmaceutically acceptable salt thereof.

28. A method of treating Parkinson's disease in a human patient in need thereof which comprises administering to the patient a therapeutically effective amount of the compound of claim 1 or a pharmaceutically acceptable salt thereof.

29. A method of treating Parkinson's disease in a human patient in need thereof which comprises administering to the patient a therapeutically effective amount of the compound of claim 2.

30. A method of treating Parkinson's disease in a human patient in need thereof which comprises administering to the patient a therapeutically effective amount of the compound of claim 3 in the form of a pharmaceutically acceptable salt thereof.

31. A method of treating Parkinson's disease in a human patient in need thereof which comprises administering to the patient a therapeutically effective amount of the compound of claim 4 or a pharmaceutically acceptable salt thereof.

32. A method of treating Parkinson's disease in a human patient in need thereof which comprises administering to the patient a therapeutically effective amount of the compound of claim 5.

33. A method of treating Parkinson's disease in a human patient in need thereof which comprises administering to the patient a therapeutically effective amount of the compound of claim 6 in the form of a pharmaceutically acceptable salt thereof.

34. A method of treating Parkinson's disease in a human patient in need thereof which comprises administering to the patient a therapeutically effective amount of the compound of claim 7 or a pharmaceutically acceptable salt thereof.

35. A method of treating Parkinson's disease in a human patient in need thereof which comprises administering to the patient a therapeutically effective amount of the compound of claim 8.

36. A method of treating Parkinson's disease in a human patient in need thereof which comprises administering to the patient a therapeutically effective amount of the compound of claim 9 in the form of pharmaceutically acceptable salt thereof.

37. A method of treating Progressive supranuclear palsy in a human patient in need thereof which comprises administering to the patient a therapeutically effective amount of the compound of claim 1 or a pharmaceutically acceptable salt thereof.

38. A method of treating Progressive supranuclear palsy in a human patient in need thereof which comprises administering to the patient a therapeutically effective amount of the compound of claim 2.

39. A method of treating Progressive supranuclear palsy in a human patient in need thereof which comprises administering to the patient a therapeutically effective amount of the compound of claim 3 in the form of a pharmaceutically acceptable salt thereof.

40. A method of treating Progressive supranuclear palsy in a human patient in need thereof which comprises administering to the patient a therapeutically effective amount of the compound of claim 4 or a pharmaceutically acceptable salt thereof.

41. A method of treating Progressive supranuclear palsy in a human patient in need thereof which comprises administering to the patient a therapeutically effective amount of the compound of claim 5.

42. A method of treating Progressive supranuclear palsy in a human patient in need thereof which comprises administering to the patient a therapeutically effective amount of the compound of claim 6 in the form of a pharmaceutically acceptable salt thereof.

43. A method of treating Progressive supranuclear palsy in a human patient in need thereof which comprises administering to the patient a therapeutically effective amount of the compound of claim 7 or a pharmaceutically acceptable salt thereof.

44. A method of treating Progressive supranuclear palsy in a human patient in need thereof which comprises administering to the patient a therapeutically effective amount of the compound of claim 8.

45. A method of treating Progressive supranuclear palsy in a human patient in need thereof which comprises administering to the patient a therapeutically effective amount of the compound of claim 9 in the form of pharmaceutically acceptable salt thereof.

* * * * *